(12) United States Patent
Wogulis et al.

(10) Patent No.: US 11,965,189 B2
(45) Date of Patent: Apr. 23, 2024

US011965189B2

(54) CELLOBIOHYDROLASE VARIANTS AND POLYNUCLEOTIDES ENCODING SAME

(71) Applicant: Novozymes A/S, Bagsvaerd (DK)

(72) Inventors: Mark Wogulis, Davis, CA (US); Leslie DeMars, Roseville, CA (US); David Osborn, Sacramento, CA (US)

(73) Assignee: Novozymes A/S, Bagsvaerd (DK)

( * ) Notice: Subject to any disclaimer, the term of this patent is extended or adjusted under 35 U.S.C. 154(b) by 320 days.

(21) Appl. No.: 16/088,038

(22) PCT Filed: Mar. 24, 2017

(86) PCT No.: PCT/US2017/024005
§ 371 (c)(1),
(2) Date: Sep. 24, 2018

(87) PCT Pub. No.: WO2017/165760
PCT Pub. Date: Sep. 28, 2017

(65) Prior Publication Data
US 2020/0299664 A1     Sep. 24, 2020

Related U.S. Application Data

(60) Provisional application No. 62/312,806, filed on Mar. 24, 2016.

(51) Int. Cl.
*C12N 9/42* (2006.01)
*C12P 7/10* (2006.01)
*C12P 19/02* (2006.01)
*C12P 19/14* (2006.01)

(52) U.S. Cl.
CPC .............. *C12N 9/2437* (2013.01); *C12P 7/10* (2013.01); *C12P 19/02* (2013.01); *C12P 19/14* (2013.01); *C12Y 302/01* (2013.01)

(58) Field of Classification Search
None
See application file for complete search history.

(56) References Cited

U.S. PATENT DOCUMENTS

| 7,375,197 B2 | 5/2008 | Adney et al. | |
|---|---|---|---|
| 2005/0048619 A1* | 3/2005 | Teter | C11D 3/38645 435/69.1 |
| 2009/0162916 A1* | 6/2009 | Adney | C12Y 302/01091 435/209 |
| 2014/0248663 A1 | 9/2014 | Tang et al. | |
| 2014/0342410 A1* | 11/2014 | Spodsberg | C12P 19/02 435/252.31 |
| 2015/0315560 A1 | 11/2015 | Bott et al. | |
| 2016/0201104 A1* | 7/2016 | Bott | C12N 9/2434 435/254.2 |
| 2017/0152497 A1 | 6/2017 | Persillon et al. | |
| 2018/0044652 A1* | 2/2018 | McBrayer | C13K 1/02 |

FOREIGN PATENT DOCUMENTS

| WO | 2004016760 A2 | 2/2004 | |
|---|---|---|---|
| WO | 2005001065 A2 | 1/2005 | |
| WO | 2005028636 A2 | 3/2005 | |
| WO | 2011050037 A1 | 4/2011 | |
| WO | 2012048171 A2 | 4/2012 | |
| WO | WO-2014093275 A1 * | 6/2014 | ........... C12N 9/2434 |
| WO | 2014138672 A1 | 9/2014 | |
| WO | WO-2014138672 A1 * | 9/2014 | ........... C12N 9/2437 |
| WO | 2015193587 A1 | 12/2015 | |

OTHER PUBLICATIONS

Bhiri et al., Molecular cloning, gene expression analysis and structural modelling of the cellobiohydrolase I from Penicillium occitanis, Enz. Microbiol. Technol. 46, 2010, 74-81. (Year: 2010).*
Uniprot, Accession No. B0Y8K2, 2014, www.uniprot.org. (Year: 2014).*
Uniprot, Accession No. A0A2H3I4G6, 2021, www.uniprot.org. (Year: 2021).*
Dana et al., Biased Clique Shuffling Reveals Stabilizing Mutations in Cellulase Cel7A, Biotechnol Bioeng. 109, 2012, 2710-19. (Year: 2012).*
Uniprot, Accession No. Q87FL9, 2011, www.uniprot.org. (Year: 2011).*
Uniprot, Accession No. A0A1Q5UH86, 2021, www.uniprot.org. (Year: 2021).*
Uniprot, Accession No. Q8TFL9, 2011, www.uniprot.org . . . (Year: 2011).*
Lopes et al, 2013, Appl Biochem Biotechnol 171(3), 616-625.

* cited by examiner

*Primary Examiner* — Todd M Epstein
(74) *Attorney, Agent, or Firm* — David A. Fazzolare

(57) ABSTRACT

The present invention relates to cellobiohydrolase variants having increased thermal activity or thermostability, polynucleotides encoding the variants; nucleic acid constructs, vectors, and host cells comprising the polynucleotides; and methods of using the variants.

45 Claims, 2 Drawing Sheets

Specification includes a Sequence Listing.

```
              *        20         *        40         *        60
1 : QQVGTLTTETHPSLTWSQCTAGGSCSTVTGSVVIDSNWRWVHSTSGSTNCYTGNTWDATL :  60
2 : QSACTLQSETHPPLTWQKCSSGGTCTQQTGSVVIDANWRWTHATNSSTNCYDGNTWSSTL :  60
3 : QQAGTATAENHPPLTWQECTAPGSCTTQNGAVVLDANWRWVHDVNGYTNCYTGNTWNPTY :  60
4 : QQIGTYTAETHPSLSWSTCKSGGSCTTNSGAITLDANWRWVHGVNTSTNCYTGNTWNSAI :  60
5 : QQIGTYQTETHPPLTWQTCTSGGSCTTNQGSIVLDANWRWVHEVGSTTNCYTGNTWDTSI :  60
6 : QQVGTSQAEVHPSMTWQSCTAGGSCTTNNGKVVIDANWRWVHKVGDYTNCYTGNTWDTTI :  60

*        80         *       100         *       120
1 : CPDDVTCAANCALDGASYSSTYGVTTSGNSLRLNFVT-TASQKNIGSRLYLLENDTTYQK : 119
2 : CPDNETCAKNCCLDGAAYASTYGVTTSGNSLSIGFVT-QSAQKNVGARLYLMASDTTYQE : 119
3 : CPDDETCAQNCALDGADYEGTYGVTSSGSSLKLNFVT----GSNVGSRLYLLQDDSTYQI : 116
4 : CDTDASCAQDCALDGADYSGTYGITTSGNSLRLNFVT----GSNVGSRTYLMADNTHYQI : 116
5 : CSTDTTCAQQCAVDGADYEGTYGITTSGSQVRINFVTNNSNGKNVGARVYMMADNTHYQI : 120
6 : CPDDATCASNCALEGANYESTYGVTASGNSLRLNFVT-TSQQKNIGSRLYMMKDDSTYEM : 119

*       140         *       160         *       180
1 : FNLLNQEFTFDVDVSNLPCGLNGALYFVDMDADGGMAKYSTNKAGAKYGTGYCDSQCPRD : 179
2 : FTLLGNEFSFDVDVSQLPCGLNGALYFVSMDADGGVSKYPTNTAGAKYGTGYCDSQCPRD : 179
3 : FKLLNREFTFDVDVSNLPCGLNGALYFVAMDADGGVSKYPNNKAGAKYGTGYCDSQCPRD : 176
4 : FDLLNQEFTFTVDVSHLPCGLNGALYFVTMDADGGVSKYPNNKAGAQYGVGYCDSQCPRD : 176
5 : YQLLNQEFTFDVDVSNLPCGLNGALYFVVMDADGGVSKYPNNKAGAQYGVGYCDSQCPRD : 180
6 : FKLLNQEFTFDVDVSNLPCGLNGALYFVAMDADGGMSKYPTNKAGAKYGTGYCDSQCPRD : 179

*       200         *       220         *       240
1 : LKFIDGQANVEGWTPSTNDVNSGIGNHGSCCAEMDIWEANSISNAVTPHPCDTPSQTMCT : 239
2 : LKFINGQANVEGWEPSSNNANTGIGGHGSCCSEMDIWEANSISEALTPHPCTTVGQEICE : 239
3 : LKFIDGEANVEGWQPSSNNANTGIGDHGSCCAEMDVWEANSISNAVTPHPCDTPGQTMCS : 236
4 : LKFIAGQANVEGWTPSANNANTGIGNHGACCAELDIWEANSISEALTPHPCDTPGLSVCT : 236
5 : LKFIQGQANVEGWQPSSNNANTGLGNHGSCCAELDVWESNSISQALTPHPCDTPTNTLCT : 240
6 : LKFINGQANVEGWQPSSNDANAGTGNHGSCCAEMDIWEANSISTAFTPHPCDTPGQVMCT : 239

*       260         *       280         *       300
1 : EDACGGTYSTSRYAGTCDPDGCDFNPYRMGDTSFFGPGL--TVDTKSPFTVVTQFITNDG : 297
2 : GDGCGGTYSDNRYGGTCDPDGCDWNPYRLGNTSFYGPGSSFTLDTTKKLTVVTQFETSGA : 299
3 : GDDCGGTYSNDRYAGTCDPDGCDFNPYRMGNTSFYGPGK--IIDTTKPFTVVTQFLTDDG : 294
4 : TDACGGTYSSDRYAGTCDPDGCDFNPYRLGVTDFYGSGK--TVDTTKPFTVVTQFVTNDG : 294
5 : GDSCGGTYSSNRYAGTCDPDGCDFNPYRLGNTTFYGPGK--TIDTTKPFTVVTQFITDDG : 298
6 : GDACGGTYSSDRYGGTCDPDGCDFNSFRQGNKTFYGPGM--TVDTKSKFTVVTQFITDDG : 297

*       320         *       340         *       360
1 : TSSGTLSEIKRFYVQNGKVIGQPQSTITGVTGNSITDTFCNAQKTAFGDTNDFTKHGGMA : 357
2 : --------INRYYVQNGVTFQQPNAELGSYSGNELNDDYCTAEEAEFGGS-SFSDKGGLT : 350
3 : TDTGTLSEIKRFYVQNGNVIPQPNSDISGVTGNSITTEFCTAQKQAFGDTDDFSQHGGLA : 354
4 : TSTGSLSEIRRYYVQNGVVIPQPSSKISGISGNVINSDYCAAEISTFGGTASFNKHGGLT : 354
5 : TSSGTLSEIRRFYVQNGVTYAQPNSDVSGISGNAINSAYCTAENTVFNGAGTFAQHGGLA : 358
6 : TSSGTLKEIKRFYVQNGKVIPNSESTWTGVSGNSITTEYCTAQKSLFQDQNVFEKHGGLE : 357
```

FIG. 1A

```
                *         380         *         400         *         420
1 : GMGAGLADGMVLVMSLWDDHAADMLWLDSTYPTNASSTTPGVKRGTCDISSGDPTTVEST : 417
2 : QFKKATSGGMVLVMSLWDDYYANMLWLDSTYPTNETSSTPGAVRGSCSTSSGVPAQVESQ : 410
3 : KMGAAMQQGMVLVMSLWDDYAAQMLWLDSDYPTDADPTTPGIARGTCPTDSGVPSDVESQ : 414
4 : NMAAGMEAGMVLVMSLWDDYAVNMLWLDSTYPTNATG-TPGAARGTCATTSGDPKTVESQ : 413
5 : GMSQAMSTGMVLVMSLWDDYYADMLWLDSTYPTNDTASTPGAVRGTCSTSSGVPSQVESA : 418
6 : GMGAALAQGMVLVMSLWDDHSANMLWLDSNYPTTASSTTPGVARGTCDISSGVPADVEAN : 417

*         440         *         460         *         480
1 : YPNAYVIYSNIKTGPLNSTFTGTTSGTTSSSTTTTSTTTTSKTSSTTTTTTSKTSSTSST : 477
2 : SPNAKVTFSNIKFGPIGSTGNPSGGNPPGGNPPGTTTTRRPATTTGSSPGPT-------- : 462
3 : SPNSYVTYSNIKFGPINSTFTAS------------------------------------ : 437
4 : SGSSYVTFSDIRVGPFNSTFSGGSSTGGSTTTTASRTTTTSASSTSTSSTST-------- : 465
5 : SPNAYVTYSNIKVGPIGSTFNSGGSGSGSSSSTT--TTTHASTTTTSSASST-------- : 468
6 : HPDAYVVYSNIKVGPIGSTFNSGGSNPGGGTTTT--TTTQPTTTTTTAGNPG-------- : 467

*         500         *         520
1 : STTTSTGSSTTGAAHYAQCGGIGWTGATTCVSPYTCTKQNDYYSQCL : 524
2 : ------------QSHYGQCGGIGYSGPTVCASGTTCQVLNPYYSQCL : 497
3 : ---------------------------------------------- :   -
4 : --------GTGVAGHWGQCGGQGWTGPTTCVSGTTCTVVNPYYSQCL : 504
5 : --------GTGVAQHWGQCGGQGWTGPTTCVSPYTCQELNPYYYQCL : 507
6 : --------GTGVAQHYGQCGGIGWTGPTTCASPYTCQKLNDYYSQCL : 506
```

FIG. 1B

SEQUENCE LISTING

```
<160> NUMBER OF SEQ ID NOS: 79

<210> SEQ ID NO 1
<211> LENGTH: 524
<212> TYPE: PRT
<213> ORGANISM: Penicillium vasconiae

<400> SEQUENCE: 1
```

Gln Gln Val Gly Thr Leu Thr Thr Glu Thr His Pro Ser Leu Thr Trp
1               5                   10                  15

Ser Gln Cys Thr Ala Gly Gly Ser Cys Ser Thr Val Thr Gly Ser Val
            20                  25                  30

Val Ile Asp Ser Asn Trp Arg Trp Val His Ser Thr Ser Gly Ser Thr
        35                  40                  45

Asn Cys Tyr Thr Gly Asn Thr Trp Asp Ala Thr Leu Cys Pro Asp Asp
    50                  55                  60

Val Thr Cys Ala Ala Asn Cys Ala Leu Asp Gly Ala Ser Tyr Ser Ser
65                  70                  75                  80

Thr Tyr Gly Val Thr Thr Ser Gly Asn Ser Leu Arg Leu Asn Phe Val
                85                  90                  95

Thr Thr Ala Ser Gln Lys Asn Ile Gly Ser Arg Leu Tyr Leu Leu Glu
            100                 105                 110

Asn Asp Thr Thr Tyr Gln Lys Phe Asn Leu Leu Asn Gln Glu Phe Thr
        115                 120                 125

Phe Asp Val Asp Val Ser Asn Leu Pro Cys Gly Leu Asn Gly Ala Leu
    130                 135                 140

Tyr Phe Val Asp Met Asp Ala Asp Gly Gly Met Ala Lys Tyr Ser Thr
145                 150                 155                 160

Asn Lys Ala Gly Ala Lys Tyr Gly Thr Gly Tyr Cys Asp Ser Gln Cys
                165                 170                 175

Pro Arg Asp Leu Lys Phe Ile Asp Gly Gln Ala Asn Val Glu Gly Trp
            180                 185                 190

Thr Pro Ser Thr Asn Asp Val Asn Ser Gly Ile Gly Asn His Gly Ser
        195                 200                 205

Cys Cys Ala Glu Met Asp Ile Trp Glu Ala Asn Ser Ile Ser Asn Ala
    210                 215                 220

Val Thr Pro His Pro Cys Asp Thr Pro Ser Gln Thr Met Cys Thr Glu

-continued

```
                225                 230                 235                 240
Asp Ala Cys Gly Gly Thr Tyr Ser Thr Ser Arg Tyr Ala Gly Thr Cys
                245                 250                 255

Asp Pro Asp Gly Cys Asp Phe Asn Pro Tyr Arg Met Gly Asp Thr Ser
                260                 265                 270

Phe Phe Gly Pro Gly Leu Thr Val Asp Thr Lys Ser Pro Phe Thr Val
                275                 280                 285

Val Thr Gln Phe Ile Thr Asn Asp Gly Thr Ser Ser Gly Thr Leu Ser
                290                 295                 300

Glu Ile Lys Arg Phe Tyr Val Gln Asn Gly Lys Val Ile Gly Gln Pro
305                 310                 315                 320

Gln Ser Thr Ile Thr Gly Val Thr Gly Asn Ser Ile Thr Asp Thr Phe
                325                 330                 335

Cys Asn Ala Gln Lys Thr Ala Phe Gly Asp Thr Asn Asp Phe Thr Lys
                340                 345                 350

His Gly Gly Met Ala Gly Met Gly Ala Gly Leu Ala Asp Gly Met Val
                355                 360                 365

Leu Val Met Ser Leu Trp Asp Asp His Ala Ala Asp Met Leu Trp Leu
                370                 375                 380

Asp Ser Thr Tyr Pro Thr Asn Ala Ser Ser Thr Pro Gly Val Lys
385                 390                 395                 400

Arg Gly Thr Cys Asp Ile Ser Ser Gly Asp Pro Thr Thr Val Glu Ser
                405                 410                 415

Thr Tyr Pro Asn Ala Tyr Val Ile Tyr Ser Asn Ile Lys Thr Gly Pro
                420                 425                 430

Leu Asn Ser Thr Phe Thr Gly Thr Thr Ser Gly Thr Thr Ser Ser Ser
                435                 440                 445

Thr Thr Thr Thr Ser Thr Thr Thr Ser Lys Thr Ser Ser Thr Thr
                450                 455                 460

Thr Thr Thr Thr Ser Lys Thr Ser Ser Thr Ser Ser Thr Ser Thr Thr
465                 470                 475                 480

Thr Ser Thr Gly Ser Ser Thr Gly Ala Ala His Tyr Ala Gln Cys
                485                 490                 495

Gly Gly Ile Gly Trp Thr Gly Ala Thr Thr Cys Val Ser Pro Tyr Thr
                500                 505                 510

Cys Thr Lys Gln Asn Asp Tyr Tyr Ser Gln Cys Leu
                515                 520

<210> SEQ ID NO 2
<211> LENGTH: 497
<212> TYPE: PRT
<213> ORGANISM: Trichoderma reesei

<400> SEQUENCE: 2

Gln Ser Ala Cys Thr Leu Gln Ser Glu Thr His Pro Pro Leu Thr Trp
1               5                   10                  15

Gln Lys Cys Ser Ser Gly Gly Thr Cys Thr Gln Gln Thr Gly Ser Val
                20                  25                  30

Val Ile Asp Ala Asn Trp Arg Trp Thr His Ala Thr Asn Ser Ser Thr
                35                  40                  45

Asn Cys Tyr Asp Gly Asn Thr Trp Ser Ser Thr Leu Cys Pro Asp Asn
                50                  55                  60

Glu Thr Cys Ala Lys Asn Cys Cys Leu Asp Gly Ala Ala Tyr Ala Ser
65                  70                  75                  80
```

-continued

```
Thr Tyr Gly Val Thr Thr Ser Gly Asn Ser Leu Ser Ile Gly Phe Val
                 85                  90                  95

Thr Gln Ser Ala Gln Lys Asn Val Gly Ala Arg Leu Tyr Leu Met Ala
            100                 105                 110

Ser Asp Thr Thr Tyr Gln Glu Phe Thr Leu Leu Gly Asn Glu Phe Ser
            115                 120                 125

Phe Asp Val Asp Val Ser Gln Leu Pro Cys Gly Leu Asn Gly Ala Leu
        130                 135                 140

Tyr Phe Val Ser Met Asp Ala Asp Gly Gly Val Ser Lys Tyr Pro Thr
145                 150                 155                 160

Asn Thr Ala Gly Ala Lys Tyr Gly Thr Gly Tyr Cys Asp Ser Gln Cys
                165                 170                 175

Pro Arg Asp Leu Lys Phe Ile Asn Gly Gln Ala Asn Val Glu Gly Trp
            180                 185                 190

Glu Pro Ser Ser Asn Asn Ala Asn Thr Gly Ile Gly Gly His Gly Ser
            195                 200                 205

Cys Cys Ser Glu Met Asp Ile Trp Glu Ala Asn Ser Ile Ser Glu Ala
        210                 215                 220

Leu Thr Pro His Pro Cys Thr Thr Val Gly Gln Glu Ile Cys Glu Gly
225                 230                 235                 240

Asp Gly Cys Gly Gly Thr Tyr Ser Asp Asn Arg Tyr Gly Gly Thr Cys
                245                 250                 255

Asp Pro Asp Gly Cys Asp Trp Asn Pro Tyr Arg Leu Gly Asn Thr Ser
            260                 265                 270

Phe Tyr Gly Pro Gly Ser Ser Phe Thr Leu Asp Thr Thr Lys Lys Leu
            275                 280                 285

Thr Val Val Thr Gln Phe Glu Thr Ser Gly Ala Ile Asn Arg Tyr Tyr
        290                 295                 300

Val Gln Asn Gly Val Thr Phe Gln Gln Pro Asn Ala Glu Leu Gly Ser
305                 310                 315                 320

Tyr Ser Gly Asn Glu Leu Asn Asp Asp Tyr Cys Thr Ala Glu Glu Ala
                325                 330                 335

Glu Phe Gly Gly Ser Ser Phe Ser Asp Lys Gly Gly Leu Thr Gln Phe
            340                 345                 350

Lys Lys Ala Thr Ser Gly Gly Met Val Leu Val Met Ser Leu Trp Asp
            355                 360                 365

Asp Tyr Tyr Ala Asn Met Leu Trp Leu Asp Ser Thr Tyr Pro Thr Asn
        370                 375                 380

Glu Thr Ser Ser Thr Pro Gly Ala Val Arg Gly Ser Cys Ser Thr Ser
385                 390                 395                 400

Ser Gly Val Pro Ala Gln Val Glu Ser Gln Ser Pro Asn Ala Lys Val
                405                 410                 415

Thr Phe Ser Asn Ile Lys Phe Gly Pro Ile Gly Ser Thr Gly Asn Pro
            420                 425                 430

Ser Gly Gly Asn Pro Pro Gly Gly Asn Pro Pro Gly Thr Thr Thr Thr
            435                 440                 445

Arg Arg Pro Ala Thr Thr Thr Gly Ser Ser Pro Gly Pro Thr Gln Ser
450                 455                 460

His Tyr Gly Gln Cys Gly Gly Ile Gly Tyr Ser Gly Pro Thr Val Cys
465                 470                 475                 480

Ala Ser Gly Thr Thr Cys Gln Val Leu Asn Pro Tyr Tyr Ser Gln Cys
                485                 490                 495

Leu
```

```
<210> SEQ ID NO 3
<211> LENGTH: 437
<212> TYPE: PRT
<213> ORGANISM: Penicillium emersonii

<400> SEQUENCE: 3
```

| | | | | | | | | | | | | | | |
|---|---|---|---|---|---|---|---|---|---|---|---|---|---|---|
| Gln | Gln | Ala | Gly | Thr | Ala | Thr | Ala | Glu | Asn | His | Pro | Pro | Leu | Thr | Trp |
| 1 | | | | 5 | | | | | 10 | | | | | 15 | |
| Gln | Glu | Cys | Thr | Ala | Pro | Gly | Ser | Cys | Thr | Thr | Gln | Asn | Gly | Ala | Val |
| | | | 20 | | | | | 25 | | | | | 30 | | |
| Val | Leu | Asp | Ala | Asn | Trp | Arg | Trp | Val | His | Asp | Val | Asn | Gly | Tyr | Thr |
| | | 35 | | | | | 40 | | | | | 45 | | | |
| Asn | Cys | Tyr | Thr | Gly | Asn | Thr | Trp | Asn | Pro | Thr | Tyr | Cys | Pro | Asp | Asp |
| | 50 | | | | | 55 | | | | | 60 | | | | |
| Glu | Thr | Cys | Ala | Gln | Asn | Cys | Ala | Leu | Asp | Gly | Ala | Asp | Tyr | Glu | Gly |
| 65 | | | | | 70 | | | | | 75 | | | | | 80 |
| Thr | Tyr | Gly | Val | Thr | Ser | Ser | Gly | Ser | Ser | Leu | Lys | Leu | Asn | Phe | Val |
| | | | | 85 | | | | | 90 | | | | | 95 | |
| Thr | Gly | Ser | Asn | Val | Gly | Ser | Arg | Leu | Tyr | Leu | Leu | Gln | Asp | Asp | Ser |
| | | | 100 | | | | | 105 | | | | | 110 | | |
| Thr | Tyr | Gln | Ile | Phe | Lys | Leu | Leu | Asn | Arg | Glu | Phe | Thr | Phe | Asp | Val |
| | | 115 | | | | | 120 | | | | | 125 | | | |
| Asp | Val | Ser | Asn | Leu | Pro | Cys | Gly | Leu | Asn | Gly | Ala | Leu | Tyr | Phe | Val |
| | 130 | | | | | 135 | | | | | 140 | | | | |
| Ala | Met | Asp | Ala | Asp | Gly | Gly | Val | Ser | Lys | Tyr | Pro | Asn | Asn | Lys | Ala |
| 145 | | | | | 150 | | | | | 155 | | | | | 160 |
| Gly | Ala | Lys | Tyr | Gly | Thr | Gly | Tyr | Cys | Asp | Ser | Gln | Cys | Pro | Arg | Asp |
| | | | | 165 | | | | | 170 | | | | | 175 | |
| Leu | Lys | Phe | Ile | Asp | Gly | Glu | Ala | Asn | Val | Glu | Gly | Trp | Gln | Pro | Ser |
| | | | 180 | | | | | 185 | | | | | 190 | | |
| Ser | Asn | Asn | Ala | Asn | Thr | Gly | Ile | Gly | Asp | His | Gly | Ser | Cys | Cys | Ala |
| | | 195 | | | | | 200 | | | | | 205 | | | |
| Glu | Met | Asp | Val | Trp | Glu | Ala | Asn | Ser | Ile | Ser | Asn | Ala | Val | Thr | Pro |
| | 210 | | | | | 215 | | | | | 220 | | | | |
| His | Pro | Cys | Asp | Thr | Pro | Gly | Gln | Thr | Met | Cys | Ser | Gly | Asp | Asp | Cys |
| 225 | | | | | 230 | | | | | 235 | | | | | 240 |
| Gly | Gly | Thr | Tyr | Ser | Asn | Asp | Arg | Tyr | Ala | Gly | Thr | Cys | Asp | Pro | Asp |
| | | | | 245 | | | | | 250 | | | | | 255 | |
| Gly | Cys | Asp | Phe | Asn | Pro | Tyr | Arg | Met | Gly | Asn | Thr | Ser | Phe | Tyr | Gly |
| | | | 260 | | | | | 265 | | | | | 270 | | |
| Pro | Gly | Lys | Ile | Ile | Asp | Thr | Thr | Lys | Pro | Phe | Thr | Val | Val | Thr | Gln |
| | | 275 | | | | | 280 | | | | | 285 | | | |
| Phe | Leu | Thr | Asp | Asp | Gly | Thr | Asp | Thr | Gly | Thr | Leu | Ser | Glu | Ile | Lys |
| | 290 | | | | | 295 | | | | | 300 | | | | |
| Arg | Phe | Tyr | Val | Gln | Asn | Gly | Asn | Val | Ile | Pro | Gln | Pro | Asn | Ser | Asp |
| 305 | | | | | 310 | | | | | 315 | | | | | 320 |
| Ile | Ser | Gly | Val | Thr | Gly | Asn | Ser | Ile | Thr | Thr | Glu | Phe | Cys | Thr | Ala |
| | | | | 325 | | | | | 330 | | | | | 335 | |
| Gln | Lys | Gln | Ala | Phe | Gly | Asp | Thr | Asp | Phe | Ser | Gln | His | Gly | Gly | |
| | | | 340 | | | | | 345 | | | | | 350 | | |
| Leu | Ala | Lys | Met | Gly | Ala | Ala | Met | Gln | Gln | Gly | Met | Val | Leu | Val | Met |
| | | 355 | | | | | 360 | | | | | 365 | | | |
| Ser | Leu | Trp | Asp | Asp | Tyr | Ala | Ala | Gln | Met | Leu | Trp | Leu | Asp | Ser | Asp |

```
                370                 375                 380
Tyr Pro Thr Asp Ala Asp Pro Thr Thr Pro Gly Ile Ala Arg Gly Thr
385                 390                 395                 400

Cys Pro Thr Asp Ser Gly Val Pro Ser Asp Val Glu Ser Gln Ser Pro
                405                 410                 415

Asn Ser Tyr Val Thr Tyr Ser Asn Ile Lys Phe Gly Pro Ile Asn Ser
                420                 425                 430

Thr Phe Thr Ala Ser
            435

<210> SEQ ID NO 4
<211> LENGTH: 504
<212> TYPE: PRT
<213> ORGANISM: Penicillium occitanis

<400> SEQUENCE: 4

Gln Gln Ile Gly Thr Tyr Thr Ala Glu Thr His Pro Ser Leu Ser Trp
1               5                   10                  15

Ser Thr Cys Lys Ser Gly Gly Ser Cys Thr Thr Asn Ser Gly Ala Ile
                20                  25                  30

Thr Leu Asp Ala Asn Trp Arg Trp Val His Gly Val Asn Thr Ser Thr
            35                  40                  45

Asn Cys Tyr Thr Gly Asn Thr Trp Asn Ser Ala Ile Cys Asp Thr Asp
50                  55                  60

Ala Ser Cys Ala Gln Asp Cys Ala Leu Asp Gly Ala Asp Tyr Ser Gly
65                  70                  75                  80

Thr Tyr Gly Ile Thr Thr Ser Gly Asn Ser Leu Arg Leu Asn Phe Val
                85                  90                  95

Thr Gly Ser Asn Val Gly Ser Arg Thr Tyr Leu Met Ala Asp Asn Thr
                100                 105                 110

His Tyr Gln Ile Phe Asp Leu Leu Asn Gln Glu Phe Thr Phe Thr Val
            115                 120                 125

Asp Val Ser His Leu Pro Cys Gly Leu Asn Gly Ala Leu Tyr Phe Val
130                 135                 140

Thr Met Asp Ala Asp Gly Gly Val Ser Lys Tyr Pro Asn Asn Lys Ala
145                 150                 155                 160

Gly Ala Gln Tyr Gly Val Gly Tyr Cys Asp Ser Gln Cys Pro Arg Asp
                165                 170                 175

Leu Lys Phe Ile Ala Gly Gln Ala Asn Val Glu Gly Trp Thr Pro Ser
                180                 185                 190

Ala Asn Asn Ala Asn Thr Gly Ile Gly Asn His Gly Ala Cys Cys Ala
            195                 200                 205

Glu Leu Asp Ile Trp Glu Ala Asn Ser Ile Ser Glu Ala Leu Thr Pro
210                 215                 220

His Pro Cys Asp Thr Pro Gly Leu Ser Val Cys Thr Thr Asp Ala Cys
225                 230                 235                 240

Gly Gly Thr Tyr Ser Ser Asp Arg Tyr Ala Gly Thr Cys Asp Pro Asp
                245                 250                 255

Gly Cys Asp Phe Asn Pro Tyr Arg Leu Gly Val Thr Asp Phe Tyr Gly
                260                 265                 270

Ser Gly Lys Thr Val Asp Thr Lys Pro Phe Thr Val Val Thr Gln
            275                 280                 285

Phe Val Thr Asn Asp Gly Thr Ser Thr Gly Ser Leu Ser Glu Ile Arg
            290                 295                 300
```

Arg Tyr Tyr Val Gln Asn Gly Val Val Ile Pro Gln Pro Ser Ser Lys
305                 310                 315                 320

Ile Ser Gly Ile Ser Gly Asn Val Ile Asn Ser Asp Tyr Cys Ala Ala
                325                 330                 335

Glu Ile Ser Thr Phe Gly Gly Thr Ala Ser Phe Asn Lys His Gly Gly
            340                 345                 350

Leu Thr Asn Met Ala Ala Gly Met Glu Ala Gly Met Val Leu Val Met
        355                 360                 365

Ser Leu Trp Asp Asp Tyr Ala Val Asn Met Leu Trp Leu Asp Ser Thr
    370                 375                 380

Tyr Pro Thr Asn Ala Thr Gly Thr Pro Gly Ala Ala Arg Gly Thr Cys
385                 390                 395                 400

Ala Thr Thr Ser Gly Asp Pro Lys Thr Val Glu Ser Gln Ser Gly Ser
                405                 410                 415

Ser Tyr Val Thr Phe Ser Asp Ile Arg Val Gly Pro Phe Asn Ser Thr
            420                 425                 430

Phe Ser Gly Gly Ser Ser Thr Gly Gly Ser Thr Thr Thr Ala Ser
        435                 440                 445

Arg Thr Thr Thr Ser Ala Ser Ser Thr Ser Thr Ser Ser Thr Ser
    450                 455                 460

Thr Gly Thr Gly Val Ala Gly His Trp Gly Gln Cys Gly Gly Gln Gly
465                 470                 475                 480

Trp Thr Gly Pro Thr Thr Cys Val Ser Gly Thr Thr Cys Thr Val Val
                485                 490                 495

Asn Pro Tyr Tyr Ser Gln Cys Leu
            500

<210> SEQ ID NO 5
<211> LENGTH: 507
<212> TYPE: PRT
<213> ORGANISM: Talaromyces leycettanus

<400> SEQUENCE: 5

Gln Gln Ile Gly Thr Tyr Gln Thr Glu Thr His Pro Pro Leu Thr Trp
1               5                   10                  15

Gln Thr Cys Thr Ser Gly Gly Ser Cys Thr Thr Asn Gln Gly Ser Ile
            20                  25                  30

Val Leu Asp Ala Asn Trp Arg Trp Val His Glu Val Gly Ser Thr Thr
        35                  40                  45

Asn Cys Tyr Thr Gly Asn Thr Trp Asp Thr Ser Ile Cys Ser Thr Asp
    50                  55                  60

Thr Thr Cys Ala Gln Gln Cys Ala Val Asp Gly Ala Asp Tyr Glu Gly
65                  70                  75                  80

Thr Tyr Gly Ile Thr Thr Ser Gly Ser Gln Val Arg Ile Asn Phe Val
                85                  90                  95

Thr Asn Asn Ser Asn Gly Lys Asn Val Gly Ala Arg Val Tyr Met Met
            100                 105                 110

Ala Asp Asn Thr His Tyr Gln Ile Tyr Gln Leu Leu Asn Gln Glu Phe
        115                 120                 125

Thr Phe Asp Val Asp Val Ser Asn Leu Pro Cys Gly Leu Asn Gly Ala
    130                 135                 140

Leu Tyr Phe Val Val Met Asp Ala Asp Gly Gly Val Ser Lys Tyr Pro
145                 150                 155                 160

Asn Asn Lys Ala Gly Ala Gln Tyr Gly Val Gly Tyr Cys Asp Ser Gln
                165                 170                 175

Cys Pro Arg Asp Leu Lys Phe Ile Gln Gly Gln Ala Asn Val Glu Gly
            180                 185                 190

Trp Gln Pro Ser Ser Asn Asn Ala Asn Thr Gly Leu Gly Asn His Gly
        195                 200                 205

Ser Cys Cys Ala Glu Leu Asp Val Trp Glu Ser Asn Ser Ile Ser Gln
    210                 215                 220

Ala Leu Thr Pro His Pro Cys Asp Thr Pro Thr Asn Thr Leu Cys Thr
225                 230                 235                 240

Gly Asp Ser Cys Gly Gly Thr Tyr Ser Ser Asn Arg Tyr Ala Gly Thr
                245                 250                 255

Cys Asp Pro Asp Gly Cys Asp Phe Asn Pro Tyr Arg Leu Gly Asn Thr
            260                 265                 270

Thr Phe Tyr Gly Pro Gly Lys Thr Ile Asp Thr Thr Lys Pro Phe Thr
        275                 280                 285

Val Val Thr Gln Phe Ile Thr Asp Asp Gly Thr Ser Ser Gly Thr Leu
    290                 295                 300

Ser Glu Ile Arg Arg Phe Tyr Val Gln Asn Gly Val Thr Tyr Ala Gln
305                 310                 315                 320

Pro Asn Ser Asp Val Ser Gly Ile Ser Gly Asn Ala Ile Asn Ser Ala
                325                 330                 335

Tyr Cys Thr Ala Glu Asn Thr Val Phe Asn Gly Ala Gly Thr Phe Ala
            340                 345                 350

Gln His Gly Gly Leu Ala Gly Met Ser Gln Ala Met Ser Thr Gly Met
        355                 360                 365

Val Leu Val Met Ser Leu Trp Asp Asp Tyr Tyr Ala Asp Met Leu Trp
    370                 375                 380

Leu Asp Ser Thr Tyr Pro Thr Asn Asp Thr Ala Ser Thr Pro Gly Ala
385                 390                 395                 400

Val Arg Gly Thr Cys Ser Thr Ser Ser Gly Val Pro Ser Gln Val Glu
                405                 410                 415

Ser Ala Ser Pro Asn Ala Tyr Val Thr Tyr Ser Asn Ile Lys Val Gly
            420                 425                 430

Pro Ile Gly Ser Thr Phe Asn Ser Gly Gly Ser Gly Ser Gly Ser Ser
        435                 440                 445

Ser Ser Thr Thr Thr Thr Thr His Ala Ser Thr Thr Thr Thr Ser Ser
    450                 455                 460

Ala Ser Ser Thr Gly Thr Gly Val Ala Gln His Trp Gly Gln Cys Gly
465                 470                 475                 480

Gly Gln Gly Trp Thr Gly Pro Thr Thr Cys Val Ser Pro Tyr Thr Cys
                485                 490                 495

Gln Glu Leu Asn Pro Tyr Tyr Gln Cys Leu
            500                 505

<210> SEQ ID NO 6
<211> LENGTH: 506
<212> TYPE: PRT
<213> ORGANISM: Aspergillus fumigatus

<400> SEQUENCE: 6

Gln Gln Val Gly Thr Ser Gln Ala Glu Val His Pro Ser Met Thr Trp
1               5                   10                  15

Gln Ser Cys Thr Ala Gly Gly Ser Cys Thr Thr Asn Asn Gly Lys Val
            20                  25                  30

Val Ile Asp Ala Asn Trp Arg Trp Val His Lys Val Gly Asp Tyr Thr

```
            35                  40                  45
Asn Cys Tyr Thr Gly Asn Thr Trp Asp Thr Thr Ile Cys Pro Asp Asp
 50                  55                  60

Ala Thr Cys Ala Ser Asn Cys Ala Leu Glu Gly Ala Asn Tyr Glu Ser
 65                  70                  75                  80

Thr Tyr Gly Val Thr Ala Ser Gly Asn Ser Leu Arg Leu Asn Phe Val
                     85                  90                  95

Thr Thr Ser Gln Gln Lys Asn Ile Gly Ser Arg Leu Tyr Met Met Lys
                100                 105                 110

Asp Asp Ser Thr Tyr Glu Met Phe Lys Leu Leu Asn Gln Glu Phe Thr
                115                 120                 125

Phe Asp Val Asp Val Ser Asn Leu Pro Cys Gly Leu Asn Gly Ala Leu
130                 135                 140

Tyr Phe Val Ala Met Asp Ala Asp Gly Gly Met Ser Lys Tyr Pro Thr
145                 150                 155                 160

Asn Lys Ala Gly Ala Lys Tyr Gly Thr Gly Tyr Cys Asp Ser Gln Cys
                165                 170                 175

Pro Arg Asp Leu Lys Phe Ile Asn Gly Gln Ala Asn Val Glu Gly Trp
                180                 185                 190

Gln Pro Ser Ser Asn Asp Ala Asn Ala Gly Thr Gly Asn His Gly Ser
                195                 200                 205

Cys Cys Ala Glu Met Asp Ile Trp Glu Ala Asn Ser Ile Ser Thr Ala
210                 215                 220

Phe Thr Pro His Pro Cys Asp Thr Pro Gly Gln Val Met Cys Thr Gly
225                 230                 235                 240

Asp Ala Cys Gly Gly Thr Tyr Ser Ser Asp Arg Tyr Gly Gly Thr Cys
                245                 250                 255

Asp Pro Asp Gly Cys Asp Phe Asn Ser Phe Arg Gln Gly Asn Lys Thr
                260                 265                 270

Phe Tyr Gly Pro Gly Met Thr Val Asp Thr Lys Ser Lys Phe Thr Val
                275                 280                 285

Val Thr Gln Phe Ile Thr Asp Asp Gly Thr Ser Ser Gly Thr Leu Lys
                290                 295                 300

Glu Ile Lys Arg Phe Tyr Val Gln Asn Gly Lys Val Ile Pro Asn Ser
305                 310                 315                 320

Glu Ser Thr Trp Thr Gly Val Ser Gly Asn Ser Ile Thr Thr Glu Tyr
                325                 330                 335

Cys Thr Ala Gln Lys Ser Leu Phe Gln Asp Gln Asn Val Phe Glu Lys
                340                 345                 350

His Gly Gly Leu Glu Gly Met Gly Ala Ala Leu Ala Gln Gly Met Val
                355                 360                 365

Leu Val Met Ser Leu Trp Asp Asp His Ser Ala Asn Met Leu Trp Leu
                370                 375                 380

Asp Ser Asn Tyr Pro Thr Thr Ala Ser Ser Thr Thr Pro Gly Val Ala
385                 390                 395                 400

Arg Gly Thr Cys Asp Ile Ser Ser Gly Val Pro Ala Asp Val Glu Ala
                    405                 410                 415

Asn His Pro Asp Ala Tyr Val Tyr Ser Asn Ile Lys Val Gly Pro
                420                 425                 430

Ile Gly Ser Thr Phe Asn Ser Gly Ser Asn Pro Gly Gly Gly Thr
                435                 440                 445

Thr Thr Thr Thr Thr Thr Gln Pro Thr Thr Thr Thr Thr Ala Gly
                450                 455                 460
```

Asn Pro Gly Gly Thr Gly Val Ala Gln His Tyr Gly Gln Cys Gly Gly
465                 470                 475                 480

Ile Gly Trp Thr Gly Pro Thr Thr Cys Ala Ser Pro Tyr Thr Cys Gln
                485                 490                 495

Lys Leu Asn Asp Tyr Tyr Ser Gln Cys Leu
            500                 505

<210> SEQ ID NO 7
<211> LENGTH: 40
<212> TYPE: DNA
<213> ORGANISM: Artificial sequence
<220> FEATURE:
<223> OTHER INFORMATION: Synthetic construct

<400> SEQUENCE: 7
ttgcagccaa gatctctgca cagcaggtcg gcactttgac                           40

<210> SEQ ID NO 8
<211> LENGTH: 40
<212> TYPE: DNA
<213> ORGANISM: Artificial sequence
<220> FEATURE:
<223> OTHER INFORMATION: Synthetic construct

<400> SEQUENCE: 8
taaatcatat taattaagct ctacaggcac tgggagtaat                           40

<210> SEQ ID NO 9
<211> LENGTH: 48
<212> TYPE: DNA
<213> ORGANISM: Artificial sequence
<220> FEATURE:
<223> OTHER INFORMATION: Synthetic construct

<400> SEQUENCE: 9
atctctgcac agcaggtcgg cactttgacg cccgagaccc atccatcg                  48

<210> SEQ ID NO 10
<211> LENGTH: 30
<212> TYPE: DNA
<213> ORGANISM: Artificial sequence
<220> FEATURE:
<223> OTHER INFORMATION: Synthetic construct

<400> SEQUENCE: 10
cgtcaaagtg ccgacctgct gtgcagagat                                      30

<210> SEQ ID NO 11
<211> LENGTH: 48
<212> TYPE: DNA
<213> ORGANISM: Artificial sequence
<220> FEATURE:
<223> OTHER INFORMATION: Synthetic construct

<400> SEQUENCE: 11
atctctgcac agcaggtcgg cactttgacg gccgagaccc atccatcg                  48

<210> SEQ ID NO 12
<211> LENGTH: 30
<212> TYPE: DNA
<213> ORGANISM: Artificial sequence
<220> FEATURE:
<223> OTHER INFORMATION: Synthetic construct

<400> SEQUENCE: 12
cgtcaaagtg ccgacctgct gtgcagagat                                                  30

<210> SEQ ID NO 13
<211> LENGTH: 48
<212> TYPE: DNA
<213> ORGANISM: Artificial sequence
<220> FEATURE:
<223> OTHER INFORMATION: Synthetic construct

<400> SEQUENCE: 13
acgactgaga cccatccatc gttgacctgg cagcagtgta ccgccggc                              48

<210> SEQ ID NO 14
<211> LENGTH: 30
<212> TYPE: DNA
<213> ORGANISM: Artificial sequence
<220> FEATURE:
<223> OTHER INFORMATION: Synthetic construct

<400> SEQUENCE: 14
ccaggtcaac gatggatggg tctcagtcgt                                                  30

<210> SEQ ID NO 15
<211> LENGTH: 48
<212> TYPE: DNA
<213> ORGANISM: Artificial sequence
<220> FEATURE:
<223> OTHER INFORMATION: Synthetic construct

<400> SEQUENCE: 15
aacatcggtt cccgtctgta cttgctggag gacgacacca cctaccag                              48

<210> SEQ ID NO 16
<211> LENGTH: 30
<212> TYPE: DNA
<213> ORGANISM: Artificial sequence
<220> FEATURE:
<223> OTHER INFORMATION: Synthetic construct

<400> SEQUENCE: 16
ctccagcaag tacagacggg aaccgatgtt                                                  30

<210> SEQ ID NO 17
<211> LENGTH: 48
<212> TYPE: DNA
<213> ORGANISM: Artificial sequence
<220> FEATURE:
<223> OTHER INFORMATION: Synthetic construct

<400> SEQUENCE: 17
gtggacatgg acgcagatgg tggcatggcc cgctactcca ccaacaag                              48

<210> SEQ ID NO 18
<211> LENGTH: 30
<212> TYPE: DNA
<213> ORGANISM: Artificial sequence
<220> FEATURE:
<223> OTHER INFORMATION: Synthetic construct

<400> SEQUENCE: 18
ggccatgcca ccatctgcgt ccatgtccac                                                  30

<210> SEQ ID NO 19
<211> LENGTH: 48
<212> TYPE: DNA

```
<213> ORGANISM: Artificial sequence
<220> FEATURE:
<223> OTHER INFORMATION: Synthetic construct

<400> SEQUENCE: 19
atggacgcag atggtggcat ggccaaatac cccaccaaca aggccgga            48

<210> SEQ ID NO 20
<211> LENGTH: 30
<212> TYPE: DNA
<213> ORGANISM: Artificial sequence
<220> FEATURE:
<223> OTHER INFORMATION: Synthetic construct

<400> SEQUENCE: 20
gtatttggcc atgccaccat ctgcgtccat                                30

<210> SEQ ID NO 21
<211> LENGTH: 48
<212> TYPE: DNA
<213> ORGANISM: Artificial sequence
<220> FEATURE:
<223> OTHER INFORMATION: Synthetic construct

<400> SEQUENCE: 21
agtcaatgcc cgcgggatct caagttcatc aacggccagg ccaacgtg            48

<210> SEQ ID NO 22
<211> LENGTH: 30
<212> TYPE: DNA
<213> ORGANISM: Artificial sequence
<220> FEATURE:
<223> OTHER INFORMATION: Synthetic construct

<400> SEQUENCE: 22
gatgaacttg agatcccgcg ggcattgact                                30

<210> SEQ ID NO 23
<211> LENGTH: 48
<212> TYPE: DNA
<213> ORGANISM: Artificial sequence
<220> FEATURE:
<223> OTHER INFORMATION: Synthetic construct

<400> SEQUENCE: 23
gtggaaggct ggacccctc caccaatgat cccaactccg gcattggc             48

<210> SEQ ID NO 24
<211> LENGTH: 30
<212> TYPE: DNA
<213> ORGANISM: Artificial sequence
<220> FEATURE:
<223> OTHER INFORMATION: Synthetic construct

<400> SEQUENCE: 24
atcattggtg gagggggtcc agccttccac                                30

<210> SEQ ID NO 25
<211> LENGTH: 48
<212> TYPE: DNA
<213> ORGANISM: Artificial sequence
<220> FEATURE:
<223> OTHER INFORMATION: Synthetic construct

<400> SEQUENCE: 25
tgcgacaccc cctcgcaaac catgtgcact ggcgatgcct gcggtgga            48
```

<210> SEQ ID NO 26
<211> LENGTH: 30
<212> TYPE: DNA
<213> ORGANISM: Artificial sequence
<220> FEATURE:
<223> OTHER INFORMATION: Synthetic construct

<400> SEQUENCE: 26
agtgcacatg gtttgcgagg gggtgtcgca                              30

<210> SEQ ID NO 27
<211> LENGTH: 48
<212> TYPE: DNA
<213> ORGANISM: Artificial sequence
<220> FEATURE:
<223> OTHER INFORMATION: Synthetic construct

<400> SEQUENCE: 27
gaagatgcct gcggtggaac ctacagcact gaccgctatg ccggtact        48

<210> SEQ ID NO 28
<211> LENGTH: 30
<212> TYPE: DNA
<213> ORGANISM: Artificial sequence
<220> FEATURE:
<223> OTHER INFORMATION: Synthetic construct

<400> SEQUENCE: 28
agtgctgtag gttccaccgc aggcatcttc                              30

<210> SEQ ID NO 29
<211> LENGTH: 48
<212> TYPE: DNA
<213> ORGANISM: Artificial sequence
<220> FEATURE:
<223> OTHER INFORMATION: Synthetic construct

<400> SEQUENCE: 29
aacccctacc gtatgggcga cacttctttc tacggtcctg gcttgacc        48

<210> SEQ ID NO 30
<211> LENGTH: 30
<212> TYPE: DNA
<213> ORGANISM: Artificial sequence
<220> FEATURE:
<223> OTHER INFORMATION: Synthetic construct

<400> SEQUENCE: 30
gaaagaagtg tcgcccatac ggtaggggtt                              30

<210> SEQ ID NO 31
<211> LENGTH: 48
<212> TYPE: DNA
<213> ORGANISM: Artificial sequence
<220> FEATURE:
<223> OTHER INFORMATION: Synthetic construct

<400> SEQUENCE: 31
cgcttctacg tccagaacgg caaggtcatc gcccagcccc agtctacc        48

<210> SEQ ID NO 32
<211> LENGTH: 30
<212> TYPE: DNA
<213> ORGANISM: Artificial sequence
<220> FEATURE:

```
<223> OTHER INFORMATION: Synthetic construct

<400> SEQUENCE: 32
gatgaccttg ccgttctgga cgtagaagcg                                    30

<210> SEQ ID NO 33
<211> LENGTH: 48
<212> TYPE: DNA
<213> ORGANISM: Artificial sequence
<220> FEATURE:
<223> OTHER INFORMATION: Synthetic construct

<400> SEQUENCE: 33
cgcttctacg tccagaacgg caaggtcatc ccccagcccc agtctacc                48

<210> SEQ ID NO 34
<211> LENGTH: 30
<212> TYPE: DNA
<213> ORGANISM: Artificial sequence
<220> FEATURE:
<223> OTHER INFORMATION: Synthetic construct

<400> SEQUENCE: 34
gatgaccttg ccgttctgga cgtagaagcg                                    30

<210> SEQ ID NO 35
<211> LENGTH: 48
<212> TYPE: DNA
<213> ORGANISM: Artificial sequence
<220> FEATURE:
<223> OTHER INFORMATION: Synthetic construct

<400> SEQUENCE: 35
cgcttctacg tccagaacgg caaggtcatc agccagcccc agtctacc                48

<210> SEQ ID NO 36
<211> LENGTH: 30
<212> TYPE: DNA
<213> ORGANISM: Artificial sequence
<220> FEATURE:
<223> OTHER INFORMATION: Synthetic construct

<400> SEQUENCE: 36
gatgaccttg ccgttctgga cgtagaagcg                                    30

<210> SEQ ID NO 37
<211> LENGTH: 48
<212> TYPE: DNA
<213> ORGANISM: Artificial sequence
<220> FEATURE:
<223> OTHER INFORMATION: Synthetic construct

<400> SEQUENCE: 37
aaggtcatcg gtcagcccca gtctaccatc cccggcgtca ccggtaac                48

<210> SEQ ID NO 38
<211> LENGTH: 30
<212> TYPE: DNA
<213> ORGANISM: Artificial sequence
<220> FEATURE:
<223> OTHER INFORMATION: Synthetic construct

<400> SEQUENCE: 38
gatggtagac tggggctgac cgatgacctt                                    30
```

-continued

```
<210> SEQ ID NO 39
<211> LENGTH: 48
<212> TYPE: DNA
<213> ORGANISM: Artificial sequence
<220> FEATURE:
<223> OTHER INFORMATION: Synthetic construct

<400> SEQUENCE: 39
ggtcagcccc agtctaccat cactggcgtc cccggtaact cgatcacc        48

<210> SEQ ID NO 40
<211> LENGTH: 30
<212> TYPE: DNA
<213> ORGANISM: Artificial sequence
<220> FEATURE:
<223> OTHER INFORMATION: Synthetic construct

<400> SEQUENCE: 40
gacgccagtg atggtagact ggggctgacc                            30

<210> SEQ ID NO 41
<211> LENGTH: 48
<212> TYPE: DNA
<213> ORGANISM: Artificial sequence
<220> FEATURE:
<223> OTHER INFORMATION: Synthetic construct

<400> SEQUENCE: 41
tgcaatgcgc aaaagaccgc attcggcgac cccaatgact tcaccaag        48

<210> SEQ ID NO 42
<211> LENGTH: 30
<212> TYPE: DNA
<213> ORGANISM: Artificial sequence
<220> FEATURE:
<223> OTHER INFORMATION: Synthetic construct

<400> SEQUENCE: 42
gtcgccgaat gcggtctttt gcgcattgca                            30

<210> SEQ ID NO 43
<211> LENGTH: 48
<212> TYPE: DNA
<213> ORGANISM: Artificial sequence
<220> FEATURE:
<223> OTHER INFORMATION: Synthetic construct

<400> SEQUENCE: 43
gcgcaaaaga ccgcattcgg cgacaccaat gtcttcacca agcacggt        48

<210> SEQ ID NO 44
<211> LENGTH: 30
<212> TYPE: DNA
<213> ORGANISM: Artificial sequence
<220> FEATURE:
<223> OTHER INFORMATION: Synthetic construct

<400> SEQUENCE: 44
attggtgtcg ccgaatgcgg tcttttgcgc                            30

<210> SEQ ID NO 45
<211> LENGTH: 48
<212> TYPE: DNA
<213> ORGANISM: Artificial sequence
<220> FEATURE:
<223> OTHER INFORMATION: Synthetic construct
```

<400> SEQUENCE: 45
aatgacttca ccaagcacgg tggcatggca gccatgggtg ccggtctc        48

<210> SEQ ID NO 46
<211> LENGTH: 30
<212> TYPE: DNA
<213> ORGANISM: Artificial sequence
<220> FEATURE:
<223> OTHER INFORMATION: Synthetic construct

<400> SEQUENCE: 46
tgccatgcca ccgtgcttgg tgaagtcatt        30

<210> SEQ ID NO 47
<211> LENGTH: 48
<212> TYPE: DNA
<213> ORGANISM: Artificial sequence
<220> FEATURE:
<223> OTHER INFORMATION: Synthetic construct

<400> SEQUENCE: 47
ttcaccaagc acggtggcat ggcaggcatg accgccggtc tcgctgat        48

<210> SEQ ID NO 48
<211> LENGTH: 30
<212> TYPE: DNA
<213> ORGANISM: Artificial sequence
<220> FEATURE:
<223> OTHER INFORMATION: Synthetic construct

<400> SEQUENCE: 48
catgcctgcc atgccaccgt gcttggtgaa        30

<210> SEQ ID NO 49
<211> LENGTH: 48
<212> TYPE: DNA
<213> ORGANISM: Artificial sequence
<220> FEATURE:
<223> OTHER INFORMATION: Synthetic construct

<400> SEQUENCE: 49
ttcaccaagc acggtggcat ggcaggcatg agcgccggtc tcgctgat        48

<210> SEQ ID NO 50
<211> LENGTH: 30
<212> TYPE: DNA
<213> ORGANISM: Artificial sequence
<220> FEATURE:
<223> OTHER INFORMATION: Synthetic construct

<400> SEQUENCE: 50
catgcctgcc atgccaccgt gcttggtgaa        30

<210> SEQ ID NO 51
<211> LENGTH: 48
<212> TYPE: DNA
<213> ORGANISM: Artificial sequence
<220> FEATURE:
<223> OTHER INFORMATION: Synthetic construct

<400> SEQUENCE: 51
gtcatgagtc tctgggatga ccatgcggcc aacatgctct ggctcgac        48

<210> SEQ ID NO 52
<211> LENGTH: 30

```
<212> TYPE: DNA
<213> ORGANISM: Artificial sequence
<220> FEATURE:
<223> OTHER INFORMATION: Synthetic construct

<400> SEQUENCE: 52
ggccgcatgg tcatcccaga gactcatgac                                     30

<210> SEQ ID NO 53
<211> LENGTH: 51
<212> TYPE: DNA
<213> ORGANISM: Artificial sequence
<220> FEATURE:
<223> OTHER INFORMATION: Synthetic construct

<400> SEQUENCE: 53
tggctcgaca gcacctaccc taccaacgcc gacccgacca ctcccggtgt c             51

<210> SEQ ID NO 54
<211> LENGTH: 30
<212> TYPE: DNA
<213> ORGANISM: Artificial sequence
<220> FEATURE:
<223> OTHER INFORMATION: Synthetic construct

<400> SEQUENCE: 54
ggcgttggta gggtaggtgc tgtcgagcca                                     30

<210> SEQ ID NO 55
<211> LENGTH: 57
<212> TYPE: DNA
<213> ORGANISM: Artificial sequence
<220> FEATURE:
<223> OTHER INFORMATION: Synthetic construct

<400> SEQUENCE: 55
atgctctggc tcgacagcac ctaccctacc gacgccgacc cgaccactcc cggtgtc       57

<210> SEQ ID NO 56
<211> LENGTH: 30
<212> TYPE: DNA
<213> ORGANISM: Artificial sequence
<220> FEATURE:
<223> OTHER INFORMATION: Synthetic construct

<400> SEQUENCE: 56
ggtagggtag gtgctgtcga gccagagcat                                     30

<210> SEQ ID NO 57
<211> LENGTH: 48
<212> TYPE: DNA
<213> ORGANISM: Artificial sequence
<220> FEATURE:
<223> OTHER INFORMATION: Synthetic construct

<400> SEQUENCE: 57
tggctcgaca gcacctaccc taccaacgcc gactcgacca ctcccggt                 48

<210> SEQ ID NO 58
<211> LENGTH: 30
<212> TYPE: DNA
<213> ORGANISM: Artificial sequence
<220> FEATURE:
<223> OTHER INFORMATION: Synthetic construct

<400> SEQUENCE: 58
```
ggcgttggta gggtaggtgc tgtcgagcca                                            30

<210> SEQ ID NO 59
<211> LENGTH: 48
<212> TYPE: DNA
<213> ORGANISM: Artificial sequence
<220> FEATURE:
<223> OTHER INFORMATION: Synthetic construct

<400> SEQUENCE: 59
ctcgacagca cctaccctac caacgcctcc cccaccactc ccggtgtc                        48

<210> SEQ ID NO 60
<211> LENGTH: 30
<212> TYPE: DNA
<213> ORGANISM: Artificial sequence
<220> FEATURE:
<223> OTHER INFORMATION: Synthetic construct

<400> SEQUENCE: 60
ggaggcgttg gtagggtagg tgctgtcgag                                            30

<210> SEQ ID NO 61
<211> LENGTH: 48
<212> TYPE: DNA
<213> ORGANISM: Artificial sequence
<220> FEATURE:
<223> OTHER INFORMATION: Synthetic construct

<400> SEQUENCE: 61
ggtacttgcg atatctcctc tggcgaccca gccaccgtcg agtctacc                        48

<210> SEQ ID NO 62
<211> LENGTH: 30
<212> TYPE: DNA
<213> ORGANISM: Artificial sequence
<220> FEATURE:
<223> OTHER INFORMATION: Synthetic construct

<400> SEQUENCE: 62
tgggtcgcca gaggagatat cgcaagtacc                                            30

<210> SEQ ID NO 63
<211> LENGTH: 48
<212> TYPE: DNA
<213> ORGANISM: Artificial sequence
<220> FEATURE:
<223> OTHER INFORMATION: Synthetic construct

<400> SEQUENCE: 63
aacgcctacg tcatctactc gaacatcaag gtcggtcctc tcaactcg                        48

<210> SEQ ID NO 64
<211> LENGTH: 30
<212> TYPE: DNA
<213> ORGANISM: Artificial sequence
<220> FEATURE:
<223> OTHER INFORMATION: Synthetic construct

<400> SEQUENCE: 64
cttgatgttc gagtagatga cgtaggcgtt                                            30

<210> SEQ ID NO 65
<211> LENGTH: 30
<212> TYPE: DNA
<213> ORGANISM: Artificial sequence
<220> FEATURE:
<223> OTHER INFORMATION: Synthetic construct

<400> SEQUENCE: 65 gctattttc taacaaagca tcttagatta                                      30

<210> SEQ ID NO 66
<211> LENGTH: 30
<212> TYPE: DNA
<213> ORGANISM: Artificial sequence
<220> FEATURE:
<223> OTHER INFORMATION: Synthetic construct

<400> SEQUENCE: 66
gctgatcccc tcgttttcgg aaacgctttg                                      30

<210> SEQ ID NO 67
<211> LENGTH: 33
<212> TYPE: DNA
<213> ORGANISM: Artificial sequence
<220> FEATURE:
<223> OTHER INFORMATION: Synthetic construct

<400> SEQUENCE: 67
acgtctgtcc aggcccagca ggtcggcact ttg                                  33

<210> SEQ ID NO 68
<211> LENGTH: 38
<212> TYPE: DNA
<213> ORGANISM: Artificial sequence
<220> FEATURE:
<223> OTHER INFORMATION: Synthetic construct

<400> SEQUENCE: 68
tcgccacgga gcttaattaa ctacaggcac tgggagta                             38

<210> SEQ ID NO 69
<211> LENGTH: 90
<212> TYPE: DNA
<213> ORGANISM: Artificial sequence
<220> FEATURE:
<223> OTHER INFORMATION: Synthetic construct

<400> SEQUENCE: 69
cgcggactgc gcaccatgaa gggatcaatc tcctatcaaa tctacaaagg tgccctgctc     60
ctctcggccc ttttgacgtc tgtccaggcc                                     90

<210> SEQ ID NO 70
<211> LENGTH: 90
<212> TYPE: DNA
<213> ORGANISM: Artificial sequence
<220> FEATURE:
<223> OTHER INFORMATION: Synthetic construct

<400> SEQUENCE: 70
ggcctggaca gacgtcaaaa gggccgagag gagcagggca cctttgtaga tttgatagga     60
gattgatccc ttcatggtgc gcagtccgcg                                     90

<210> SEQ ID NO 71
<211> LENGTH: 30
<212> TYPE: DNA
<213> ORGANISM: Artificial sequence
<220> FEATURE:
<223> OTHER INFORMATION: Synthetic construct -continued

<400> SEQUENCE: 71
gtgcgcagca ccggtggtgc tcgagccagt                                        30

<210> SEQ ID NO 72
<211> LENGTH: 48
<212> TYPE: DNA
<213> ORGANISM: Artificial sequence
<220> FEATURE:
<223> OTHER INFORMATION: Synthetic construct

<400> SEQUENCE: 72
actggctcga gcaccaccgg tgctgcgcac tgggcccagt gtggtgga                    48

<210> SEQ ID NO 73
<211> LENGTH: 40
<212> TYPE: DNA
<213> ORGANISM: Artificial sequence
<220> FEATURE:
<223> OTHER INFORMATION: Synthetic construct

<400> SEQUENCE: 73
atatacacaa ctggatttac atgaagggat caatctccta                             40

<210> SEQ ID NO 74
<211> LENGTH: 40
<212> TYPE: DNA
<213> ORGANISM: Artificial sequence
<220> FEATURE:
<223> OTHER INFORMATION: Synthetic construct

<400> SEQUENCE: 74
gtgtcagtca cctctagtta ctacaggcac tgggagtaat                             40

<210> SEQ ID NO 75
<211> LENGTH: 1650
<212> TYPE: DNA
<213> ORGANISM: Penicillium vasconiae
<220> FEATURE:
<221> NAME/KEY: CDS
<222> LOCATION: (1)..(1647)
<220> FEATURE:
<221> NAME/KEY: sig_peptide
<222> LOCATION: (1)..(75)
<220> FEATURE:
<221> NAME/KEY: mat_peptide
<222> LOCATION: (76)..(1647)

<400> SEQUENCE: 75

```
atg aag gga tca atc tcc tat caa atc tac aaa ggt gcc ctg ctc ctc        48
Met Lys Gly Ser Ile Ser Tyr Gln Ile Tyr Lys Gly Ala Leu Leu Leu
-25                 -20                 -15                 -10 tcg gcc ctt ttg acg tct gtc cag gcc cag cag gtc ggc act ttg acg        96
Ser Ala Leu Leu Thr Ser Val Gln Ala Gln Gln Val Gly Thr Leu Thr
                -5                  -1  1                   5 act gag acc cat cca tcg ttg acc tgg tcc cag tgt acc gcc ggc ggt       144
Thr Glu Thr His Pro Ser Leu Thr Trp Ser Gln Cys Thr Ala Gly Gly
        10                  15                  20 agc tgc tct acc gtg acc ggc agt gtg gtt atc gat tct aac tgg cgc       192
Ser Cys Ser Thr Val Thr Gly Ser Val Val Ile Asp Ser Asn Trp Arg
    25                  30                  35 tgg gtt cac tcc acc agt ggc tcg acc aac tgc tat acc ggc aac acc       240
Trp Val His Ser Thr Ser Gly Ser Thr Asn Cys Tyr Thr Gly Asn Thr
40                  45                  50                  55 tgg gac gcc acc ctc tgc cct gac gat gtg acc tgc gca gcc aac tgt       288
Trp Asp Ala Thr Leu Cys Pro Asp Asp Val Thr Cys Ala Ala Asn Cys
```

-continued

|              |    | 60 |     |     |     |     | 65  |     |     |     |     | 70  |     |     |     |     |      |
|---|---|---|---|---|---|---|---|---|---|---|---|---|---|---|---|---|---|
| gct | ctg | gat | ggc | gct | agc | tac | tcg | agc | acc | tac | ggt | gtt | acc | acc | agc | | 336 |
| Ala | Leu | Asp | Gly | Ala | Ser | Tyr | Ser | Ser | Thr | Tyr | Gly | Val | Thr | Thr | Ser | | |
|     |     | 75  |     |     |     |     | 80  |     |     |     |     | 85  |     |     |     | | |

| ggc | aat | tcc | ctg | cgt | ctg | aac | ttt | gtc | act | acg | gct | tcg | cag | aag | aac | | 384 |
|---|---|---|---|---|---|---|---|---|---|---|---|---|---|---|---|---|---|
| Gly | Asn | Ser | Leu | Arg | Leu | Asn | Phe | Val | Thr | Thr | Ala | Ser | Gln | Lys | Asn | | |
|     |     | 90  |     |     |     |     | 95  |     |     |     |     | 100 |     |     |     | | |

| atc | ggt | tcc | cgt | ctg | tac | ttg | ctg | gag | aat | gac | acc | tac | cag | aag | | | 432 |
|---|---|---|---|---|---|---|---|---|---|---|---|---|---|---|---|---|---|
| Ile | Gly | Ser | Arg | Leu | Tyr | Leu | Leu | Glu | Asn | Asp | Thr | Thr | Tyr | Gln | Lys | | |
|     | 105 |     |     |     |     | 110 |     |     |     |     | 115 |     |     |     |     | | |

| ttc | aac | ctg | ctg | aac | cag | gag | ttc | act | ttc | gat | gtg | gat | gtg | tcc | aac | | 480 |
|---|---|---|---|---|---|---|---|---|---|---|---|---|---|---|---|---|---|
| Phe | Asn | Leu | Leu | Asn | Gln | Glu | Phe | Thr | Phe | Asp | Val | Asp | Val | Ser | Asn | | |
| 120 |     |     |     | 125 |     |     |     |     | 130 |     |     |     |     | 135 |     | | |

| ctt | ccc | tgt | ggt | ctc | aac | ggt | gcc | ctc | tac | ttt | gtg | gac | atg | gac | gca | | 528 |
|---|---|---|---|---|---|---|---|---|---|---|---|---|---|---|---|---|---|
| Leu | Pro | Cys | Gly | Leu | Asn | Gly | Ala | Leu | Tyr | Phe | Val | Asp | Met | Asp | Ala | | |
|     |     |     | 140 |     |     |     |     | 145 |     |     |     |     | 150 |     |     | | |

| gat | ggt | ggc | atg | gcc | aaa | tac | tcc | acc | aac | aag | gcc | gga | gcc | aag | tat | | 576 |
|---|---|---|---|---|---|---|---|---|---|---|---|---|---|---|---|---|---|
| Asp | Gly | Gly | Met | Ala | Lys | Tyr | Ser | Thr | Asn | Lys | Ala | Gly | Ala | Lys | Tyr | | |
|     |     |     | 155 |     |     |     |     | 160 |     |     |     |     | 165 |     |     | | |

| gga | act | ggt | tac | tgc | gac | agt | caa | tgc | ccg | cgg | gat | ctc | aag | ttc | atc | | 624 |
|---|---|---|---|---|---|---|---|---|---|---|---|---|---|---|---|---|---|
| Gly | Thr | Gly | Tyr | Cys | Asp | Ser | Gln | Cys | Pro | Arg | Asp | Leu | Lys | Phe | Ile | | |
|     | 170 |     |     |     |     | 175 |     |     |     |     | 180 |     |     |     |     | | |

| gat | ggc | cag | gcc | aac | gtg | gaa | ggc | tgg | acc | ccc | tcc | acc | aat | gat | gtc | | 672 |
|---|---|---|---|---|---|---|---|---|---|---|---|---|---|---|---|---|---|
| Asp | Gly | Gln | Ala | Asn | Val | Glu | Gly | Trp | Thr | Pro | Ser | Thr | Asn | Asp | Val | | |
| 185 |     |     |     |     | 190 |     |     |     |     | 195 |     |     |     |     |     | | |

| aac | tcc | ggc | att | ggc | aat | cac | ggc | tcc | tgc | tgt | gcg | gag | atg | gat | atc | | 720 |
|---|---|---|---|---|---|---|---|---|---|---|---|---|---|---|---|---|---|
| Asn | Ser | Gly | Ile | Gly | Asn | His | Gly | Ser | Cys | Cys | Ala | Glu | Met | Asp | Ile | | |
| 200 |     |     |     | 205 |     |     |     |     | 210 |     |     |     |     | 215 |     | | |

| tgg | gag | gcc | aac | tcg | atc | tcc | aat | gcc | gtc | act | cct | cat | cct | tgc | gac | | 768 |
|---|---|---|---|---|---|---|---|---|---|---|---|---|---|---|---|---|---|
| Trp | Glu | Ala | Asn | Ser | Ile | Ser | Asn | Ala | Val | Thr | Pro | His | Pro | Cys | Asp | | |
|     |     |     | 220 |     |     |     |     | 225 |     |     |     |     | 230 |     |     | | |

| acc | ccc | tcg | caa | acc | atg | tgc | act | gaa | gat | gcc | tgc | ggt | gga | acc | tac | | 816 |
|---|---|---|---|---|---|---|---|---|---|---|---|---|---|---|---|---|---|
| Thr | Pro | Ser | Gln | Thr | Met | Cys | Thr | Glu | Asp | Ala | Cys | Gly | Gly | Thr | Tyr | | |
|     |     | 235 |     |     |     |     | 240 |     |     |     |     | 245 |     |     |     | | |

| agc | act | tcg | cgc | tat | gcc | ggt | act | tgc | gat | ccc | gat | ggc | tgt | gat | ttc | | 864 |
|---|---|---|---|---|---|---|---|---|---|---|---|---|---|---|---|---|---|
| Ser | Thr | Ser | Arg | Tyr | Ala | Gly | Thr | Cys | Asp | Pro | Asp | Gly | Cys | Asp | Phe | | |
|     | 250 |     |     |     |     | 255 |     |     |     |     | 260 |     |     |     |     | | |

| aac | ccc | tac | cgt | atg | ggc | gac | act | tct | ttc | ttc | ggt | cct | ggc | ttg | acc | | 912 |
|---|---|---|---|---|---|---|---|---|---|---|---|---|---|---|---|---|---|
| Asn | Pro | Tyr | Arg | Met | Gly | Asp | Thr | Ser | Phe | Phe | Gly | Pro | Gly | Leu | Thr | | |
| 265 |     |     |     |     | 270 |     |     |     |     | 275 |     |     |     |     |     | | |

| gtt | gac | acc | aag | tct | ccc | ttc | acc | gtg | gtg | acc | caa | ttc | atc | acc | aac | | 960 |
|---|---|---|---|---|---|---|---|---|---|---|---|---|---|---|---|---|---|
| Val | Asp | Thr | Lys | Ser | Pro | Phe | Thr | Val | Val | Thr | Gln | Phe | Ile | Thr | Asn | | |
| 280 |     |     |     | 285 |     |     |     |     | 290 |     |     |     |     | 295 |     | | |

| gat | ggc | acc | tct | tca | ggc | acc | ctg | tca | gag | atc | aag | cgc | ttc | tac | gtc | | 1008 |
|---|---|---|---|---|---|---|---|---|---|---|---|---|---|---|---|---|---|
| Asp | Gly | Thr | Ser | Ser | Gly | Thr | Leu | Ser | Glu | Ile | Lys | Arg | Phe | Tyr | Val | | |
|     |     |     | 300 |     |     |     |     | 305 |     |     |     |     | 310 |     |     | | |

| cag | aac | ggc | aag | gtc | atc | ggt | cag | ccc | cag | tct | acc | atc | act | ggc | gtc | | 1056 |
|---|---|---|---|---|---|---|---|---|---|---|---|---|---|---|---|---|---|
| Gln | Asn | Gly | Lys | Val | Ile | Gly | Gln | Pro | Gln | Ser | Thr | Ile | Thr | Gly | Val | | |
|     |     | 315 |     |     |     |     | 320 |     |     |     |     | 325 |     |     |     | | |

| acc | ggt | aac | tcg | atc | acc | gat | acc | ttc | tgc | aat | gcg | caa | aag | acc | gca | | 1104 |
|---|---|---|---|---|---|---|---|---|---|---|---|---|---|---|---|---|---|
| Thr | Gly | Asn | Ser | Ile | Thr | Asp | Thr | Phe | Cys | Asn | Ala | Gln | Lys | Thr | Ala | | |
|     | 330 |     |     |     |     | 335 |     |     |     |     | 340 |     |     |     |     | | |

| ttc | ggc | gac | acc | aat | gac | ttc | acc | aag | cac | ggt | ggc | atg | gca | ggc | atg | | 1152 |
|---|---|---|---|---|---|---|---|---|---|---|---|---|---|---|---|---|---|
| Phe | Gly | Asp | Thr | Asn | Asp | Phe | Thr | Lys | His | Gly | Gly | Met | Ala | Gly | Met | | |
| 345 |     |     |     |     | 350 |     |     |     |     | 355 |     |     |     |     |     | | |

| ggt | gcc | ggt | ctc | gct | gat | ggt | atg | gtt | ctg | gtc | atg | agt | ctc | tgg | gat | | 1200 |
|---|---|---|---|---|---|---|---|---|---|---|---|---|---|---|---|---|---|
| Gly | Ala | Gly | Leu | Ala | Asp | Gly | Met | Val | Leu | Val | Met | Ser | Leu | Trp | Asp | | |
| 360 |     |     |     | 365 |     |     |     |     | 370 |     |     |     |     | 375 |     | | |

| gac | cat | gcg | gcc | gat | atg | ctc | tgg | ctc | gac | agc | acc | tac | cct | acc | aac | | 1248 |
|---|---|---|---|---|---|---|---|---|---|---|---|---|---|---|---|---|---|

```
Asp His Ala Ala Asp Met Leu Trp Leu Asp Ser Thr Tyr Pro Thr Asn
            380                 385                 390 gcc tcc tcg acc act ccc ggt gtc aag cgc ggt act tgc gat atc tcc      1296
Ala Ser Ser Thr Thr Pro Gly Val Lys Arg Gly Thr Cys Asp Ile Ser
            395                 400                 405 tct ggc gac cca acc acc gtc gag tct acc tac ccc aac gcc tac gtc      1344
Ser Gly Asp Pro Thr Thr Val Glu Ser Thr Tyr Pro Asn Ala Tyr Val
            410                 415                 420 atc tac tcg aac atc aag act ggt cct ctc aac tcg acc ttt acc ggc      1392
Ile Tyr Ser Asn Ile Lys Thr Gly Pro Leu Asn Ser Thr Phe Thr Gly
            425                 430                 435 acc acc tcc ggc acc acc agc tct tct acc act acc act agc act act      1440
Thr Thr Ser Gly Thr Thr Ser Ser Ser Thr Thr Thr Thr Ser Thr Thr
440                 445                 450                 455 act act agc aag acc agc tct acc act acc act act agc aag acc          1488
Thr Thr Ser Lys Thr Ser Ser Thr Thr Thr Thr Thr Ser Lys Thr
            460                 465                 470 agc tct acc agc tcc acc tcg act acc acc tct act ggc tcg agc acc      1536
Ser Ser Thr Ser Ser Thr Ser Thr Thr Thr Ser Thr Gly Ser Ser Thr
            475                 480                 485 acc ggt gct gcg cac tat gcc cag tgt ggt gga att ggc tgg act ggc      1584
Thr Gly Ala Ala His Tyr Ala Gln Cys Gly Gly Ile Gly Trp Thr Gly
            490                 495                 500 gcc acc acc tgt gtc agc ccg tac act tgc acc aag cag aat gac tat      1632
Ala Thr Thr Cys Val Ser Pro Tyr Thr Cys Thr Lys Gln Asn Asp Tyr
505                 510                 515 tac tcc cag tgc ctg tag                                              1650
Tyr Ser Gln Cys Leu
520

<210> SEQ ID NO 76
<211> LENGTH: 549
<212> TYPE: PRT
<213> ORGANISM: Penicillium vasconiae

<400> SEQUENCE: 76

Met Lys Gly Ser Ile Ser Tyr Gln Ile Tyr Lys Gly Ala Leu Leu Leu
-25                 -20                 -15                 -10

Ser Ala Leu Leu Thr Ser Val Gln Ala Gln Val Gly Thr Leu Thr
            -5                  -1   1                5

Thr Glu Thr His Pro Ser Leu Trp Ser Gln Cys Thr Ala Gly Gly
            10                  15                  20

Ser Cys Ser Thr Val Thr Gly Ser Val Val Ile Asp Ser Asn Trp Arg
25                  30                  35

Trp Val His Ser Thr Ser Gly Ser Thr Asn Cys Tyr Thr Gly Asn Thr
40                  45                  50                  55

Trp Asp Ala Thr Leu Cys Pro Asp Asp Val Thr Cys Ala Ala Asn Cys
            60                  65                  70

Ala Leu Asp Gly Ala Ser Tyr Ser Ser Thr Tyr Gly Val Thr Thr Ser
            75                  80                  85

Gly Asn Ser Leu Arg Leu Asn Phe Val Thr Thr Ala Ser Gln Lys Asn
            90                  95                  100

Ile Gly Ser Arg Leu Tyr Leu Leu Glu Asn Asp Thr Thr Tyr Gln Lys
            105                 110                 115

Phe Asn Leu Leu Asn Gln Glu Phe Thr Phe Asp Val Asp Val Ser Asn
120                 125                 130                 135

Leu Pro Cys Gly Leu Asn Gly Ala Leu Tyr Phe Val Asp Met Asp Ala
            140                 145                 150
```

Asp Gly Gly Met Ala Lys Tyr Ser Thr Asn Lys Ala Gly Ala Lys Tyr
            155                 160                 165

Gly Thr Gly Tyr Cys Asp Ser Gln Cys Pro Arg Asp Leu Lys Phe Ile
        170                 175                 180

Asp Gly Gln Ala Asn Val Glu Gly Trp Thr Pro Ser Thr Asn Asp Val
185                 190                 195

Asn Ser Gly Ile Gly Asn His Gly Ser Cys Cys Ala Glu Met Asp Ile
200                 205                 210                 215

Trp Glu Ala Asn Ser Ile Ser Asn Ala Val Thr Pro His Pro Cys Asp
                220                 225                 230

Thr Pro Ser Gln Thr Met Cys Thr Glu Asp Ala Cys Gly Gly Thr Tyr
            235                 240                 245

Ser Thr Ser Arg Tyr Ala Gly Thr Cys Asp Pro Asp Gly Cys Asp Phe
        250                 255                 260

Asn Pro Tyr Arg Met Gly Asp Thr Ser Phe Phe Gly Pro Gly Leu Thr
    265                 270                 275

Val Asp Thr Lys Ser Pro Phe Thr Val Val Thr Gln Phe Ile Thr Asn
280                 285                 290                 295

Asp Gly Thr Ser Ser Gly Thr Leu Ser Glu Ile Lys Arg Phe Tyr Val
                300                 305                 310

Gln Asn Gly Lys Val Ile Gly Gln Pro Gln Ser Thr Ile Thr Gly Val
            315                 320                 325

Thr Gly Asn Ser Ile Thr Asp Thr Phe Cys Asn Ala Gln Lys Thr Ala
        330                 335                 340

Phe Gly Asp Thr Asn Asp Phe Thr Lys His Gly Met Ala Gly Met
    345                 350                 355

Gly Ala Gly Leu Ala Asp Gly Met Val Leu Val Met Ser Leu Trp Asp
360                 365                 370                 375

Asp His Ala Ala Asp Met Leu Trp Leu Asp Ser Thr Tyr Pro Thr Asn
                380                 385                 390

Ala Ser Ser Thr Thr Pro Gly Val Lys Arg Gly Thr Cys Asp Ile Ser
            395                 400                 405

Ser Gly Asp Pro Thr Thr Val Glu Ser Thr Tyr Pro Asn Ala Tyr Val
        410                 415                 420

Ile Tyr Ser Asn Ile Lys Thr Gly Pro Leu Asn Ser Thr Phe Thr Gly
    425                 430                 435

Thr Thr Ser Gly Thr Thr Ser Ser Ser Thr Thr Thr Thr Ser Thr Thr
440                 445                 450                 455

Thr Thr Ser Lys Thr Ser Ser Thr Thr Thr Thr Thr Thr Ser Lys Thr
                460                 465                 470

Ser Ser Thr Ser Ser Thr Ser Thr Thr Ser Thr Gly Ser Ser Thr
            475                 480                 485

Thr Gly Ala Ala His Tyr Ala Gln Cys Gly Gly Ile Gly Trp Thr Gly
        490                 495                 500

Ala Thr Thr Cys Val Ser Pro Tyr Thr Cys Thr Lys Gln Asn Asp Tyr
        505                 510                 515

Tyr Ser Gln Cys Leu
520

<210> SEQ ID NO 77
<211> LENGTH: 49
<212> TYPE: DNA
<213> ORGANISM: Artificial sequence
<220> FEATURE:

```
<223> OTHER INFORMATION: Synthetic construct

<400> SEQUENCE: 77
acacaactgg ggatccacca tgaagggatc aatctcctat caaatctac                49

<210> SEQ ID NO 78
<211> LENGTH: 41
<212> TYPE: DNA
<213> ORGANISM: Artificial sequence
<220> FEATURE:
<223> OTHER INFORMATION: Synthetic construct

<400> SEQUENCE: 78
ccctctagat ctcgagcacc acttttctcc caaatttgaa g                        41

<210> SEQ ID NO 79
<211> LENGTH: 57
<212> TYPE: DNA
<213> ORGANISM: Artificial sequence
<220> FEATURE:
<223> OTHER INFORMATION: Synthetic construct

<400> SEQUENCE: 79
atgcttttgc aagccttcct tttccttttg gctggttttg cagccaagat ctctgca       57
```

CELLOBIOHYDROLASE VARIANTS AND POLYNUCLEOTIDES ENCODING SAME

CROSS-REFERENCE TO RELATED APPLICATIONS

This application is a 35 U.S.C. § 371 national application of PCT/US2017/024005 filed Mar. 24, 2017, which claims priority or the benefit under 35 U.S.C. § 119 of U.S. Provisional Application No. 62/312,806 filed Mar. 24, 2016, the contents of which are fully incorporated herein by reference.

REFERENCE TO A SEQUENCE LISTING

The contents of the electronic sequence listing created on Mar. 24, 2017, named SQ.txt and 51 KB in size, is hereby incorporated by reference in its entirety.

BACKGROUND OF THE INVENTION

Field of the Invention

The present invention relates to cellobiohydrolase variants, polynucleotides encoding the variants, and methods of producing and using the variants.

Description of the Related Art

Cellulose is a polymer of the simple sugar glucose covalently linked by beta-1,4-bonds. Many microorganisms produce enzymes that hydrolyze beta-linked glucans. These enzymes include endoglucanases, cellobiohydrolases, and beta-glucosidases. Endoglucanases digest the cellulose polymer at random locations, opening it to attack by cellobiohydrolases. Cellobiohydrolases sequentially release molecules of cellobiose from the ends of the cellulose polymer. Cellobiose is a water-soluble beta-1,4-linked dimer of glucose. Beta-glucosidases hydrolyze cellobiose to glucose.

The conversion of lignocellulosic feedstocks into ethanol has the advantages of the ready availability of large amounts of feedstock, the desirability of avoiding burning or land filling the materials, and the cleanliness of the ethanol fuel. Wood, agricultural residues, herbaceous crops, and municipal solid wastes have been considered as feedstocks for ethanol production. These materials primarily consist of cellulose, hemicellulose, and lignin. Once the lignocellulose is converted to fermentable sugars, e.g., glucose, the fermentable sugars can easily be fermented by yeast into ethanol.

WO 2011/050037 discloses *Thielavia terrestris* cellobiohydrolase variants with improved thermostability. WO 2011/050037 discloses *Aspergillus fumigatus* cellobiohydrolase variants with improved thermostability. WO 2005/028636 discloses variants of *Hypocrea jecorina* Cel7A cellobiohydrolase I. WO 2005/001065 discloses variants of *Humicola grisea* Cel7A cellobiohydrolase I, *Hypocrea jecorina* cellobiohydrolase I, and *Scytalidium thermophilium* cellobiohydrolase I. WO 2004/016760 discloses variants of *Hypocrea jecorina* Cel7A cellobiohydrolase I. U.S. Pat. No. 7,375,197 discloses variants of *Trichoderma reesei* cellobiohydrolase I.

There is a need in the art for cellobiohydrolase variants with improved properties to increase the efficiency of the saccharification of lignocellulosic feedstocks.

SUMMARY OF THE INVENTION

The present invention relates to isolated cellobiohydrolase variants, comprising a substitution at one or more (e.g., several) positions corresponding to positions 8, 17, 113, 157, 159, 184, 199, 240, 250, 274, 318, 325, 328, 347, 349, 358, 360, 380, 391, 393, 394, 412, and 430 of SEQ ID NO: 1, wherein the variants have cellobiohydrolase activity.

The present invention also relates to cellobiohydrolase variants, comprising a variant catalytic domain, wherein the variant catalytic domain comprises a substitution at one or more (e.g., several) positions corresponding to positions 8, 17, 113, 157, 159, 184, 199, 240, 250, 274, 318, 325, 328, 347, 349, 358, 360, 380, 391, 393, 394, 412, and 430 of SEQ ID NO: 1, wherein the cellobiohydrolase variants have cellobiohydrolase activity.

The present invention also relates to isolated polynucleotides encoding the variants; nucleic acid constructs, vectors, and host cells comprising the polynucleotides; and methods of producing the variants.

The present invention also relates to processes for degrading a cellulosic material, comprising: treating the cellulosic material with an enzyme composition comprising a cellobiohydrolase variant of the present invention. In one aspect, the processes further comprise recovering the degraded cellulosic material.

The present invention also relates to processes of producing a fermentation product, comprising: (a) saccharifying a cellulosic material with an enzyme composition comprising a cellobiohydrolase variant of the present invention; (b) fermenting the saccharified cellulosic material with one or more (e.g., several) fermenting microorganisms to produce the fermentation product; and (c) recovering the fermentation product from the fermentation.

The present invention also relates to processes of fermenting a cellulosic material, comprising: fermenting the cellulosic material with one or more (e.g., several) fermenting microorganisms, wherein the cellulosic material is saccharified with an enzyme composition comprising a cellobiohydrolase variant of the present invention. In one aspect, the fermenting of the cellulosic material produces a fermentation product. In another aspect, the processes further comprise recovering the fermentation product from the fermentation.

BRIEF DESCRIPTION OF THE FIGURES

FIGS. 1A and 1B show an alignment of a *Penicillium vasconiae* cellobiohydrolase (SEQ ID NO: 1), a *Trichoderma reesei* cellobiohydrolase (SEQ ID NO: 2), a *Penicillium emersonii* cellobiohydrolase (SEQ ID NO: 3), a *Penicillium oxitanis* cellobiohydrolase (SEQ ID NO: 4), a *Talaromyces leycettanus* cellobiohydrolase (SEQ ID NO: 5), and an *Aspergillus fumigatus* cellobiohydrolase (SEQ ID NO: 6).

DEFINITIONS

Acetylxylan esterase: The term "acetylxylan esterase" means a carboxylesterase (EC 3.1.1.72) that catalyzes the hydrolysis of acetyl groups from polymeric xylan, acetylated xylose, acetylated glucose, alpha-napthyl acetate, and p-nitrophenyl acetate. Acetylxylan esterase activity can be determined using 0.5 mM p-nitrophenylacetate as substrate in 50 mM sodium acetate pH 5.0 containing 0.01% TWEEN™ 20 (polyoxyethylene sorbitan monolaurate). One unit of acetylxylan esterase is defined as the amount of enzyme capable of releasing 1 μmole of p-nitrophenolate anion per minute at pH 5, 25° C.

Alpha-L-arabinofuranosidase: The term "alpha-L-arabinofuranosidase" means an alpha-L-arabinofuranoside arabinofuranohydrolase (EC 3.2.1.55) that catalyzes the hydrolysis of terminal non-reducing alpha-L-arabinofuranoside residues in alpha-L-arabinosides. The enzyme acts on alpha-L-arabinofuranosides, alpha-L-arabinans containing (1,3)- and/or (1,5)-linkages, arabinoxylans, and arabinogalactans. Alpha-L-arabinofuranosidase is also known as arabinosidase, alpha-arabinosidase, alpha-L-arabinosidase, alpha-arabinofuranosidase, polysaccharide alpha-L-arabinofuranosidase, alpha-L-arabinofuranoside hydrolase, L-arabinosidase, or alpha-L-arabinanase. Alpha-L-arabinofuranosidase activity can be determined using 5 mg of medium viscosity wheat arabinoxylan (Megazyme International Ireland, Ltd., Bray, Co. Wicklow, Ireland) per ml of 100 mM sodium acetate pH 5 in a total volume of 200 µl for 30 minutes at 40° C. followed by arabinose analysis by AMINEX® HPX-87H column chromatography (Bio-Rad Laboratories, Inc.).

Alpha-glucuronidase: The term "alpha-glucuronidase" means an alpha-D-glucosiduronate glucuronohydrolase (EC 3.2.1.139) that catalyzes the hydrolysis of an alpha-D-glucuronoside to D-glucuronate and an alcohol. Alpha-glucuronidase activity can be determined according to de Vries, 1998, *J. Bacteriol.* 180: 243-249. One unit of alpha-glucuronidase equals the amount of enzyme capable of releasing 1 µmole of glucuronic or 4-O-methylglucuronic acid per minute at pH 5, 40° C.

Auxiliary Activity 9 polypeptide: The term "Auxiliary Activity 9 polypeptide" or "AA9 polypeptide" means a polypeptide classified as a lytic polysaccharide monooxygenase (Quinlan et al., 2011, *Proc. Natl. Acad. Sci. USA* 108: 15079-15084; Phillips et al., 2011, *ACS Chem. Biol.* 6: 1399-1406; Li et al., 2012, *Structure* 20: 1051-1061). AA9 polypeptides were formerly classified into the glycoside hydrolase Family 61 (GH61) according to Henrissat, 1991, *Biochem. J.* 280: 309-316, and Henrissat and Bairoch, 1996, *Biochem. J.* 316: 695-696.

AA9 polypeptides enhance the hydrolysis of a cellulosic material by an enzyme having cellulolytic activity. Cellulolytic enhancing activity can be determined by measuring the increase in reducing sugars or the increase of the total of cellobiose and glucose from the hydrolysis of a cellulosic material by cellulolytic enzyme under the following conditions: 1-50 mg of total protein/g of cellulose in pretreated corn stover (PCS), wherein total protein is comprised of 50-99.5% w/w cellulolytic enzyme protein and 0.5-50% w/w protein of an AA9 polypeptide for 1-7 days at a suitable temperature, such as 40° C.-80° C., e.g., 40° C., 45° C., 50° C., 55° C., 60° C., 65° C., 70° C., 75° C., or 80° C. and a suitable pH, such as 4-9, e.g., 4.5, 5.0, 5.5, 6.0, 6.5, 7.0, 7.5, 8.0, 8.5, or 9.0, compared to a control hydrolysis with equal total protein loading without cellulolytic enhancing activity (1-50 mg of cellulolytic protein/g of cellulose in PCS).

AA9 polypeptide enhancing activity can be determined using a mixture of CELLUCLAST™ 1.5 L (Novozymes A/S, Bagsværd, Denmark) and beta-glucosidase as the source of the cellulolytic activity, wherein the beta-glucosidase is present at a weight of at least 2-5% protein of the cellulase protein loading. In one aspect, the beta-glucosidase is an *Aspergillus oryzae* beta-glucosidase (e.g., recombinantly produced in *Aspergillus oryzae* according to WO 02/095014). In another aspect, the beta-glucosidase is an *Aspergillus fumigatus* beta-glucosidase (e.g., recombinantly produced in *Aspergillus oryzae* as described in WO 02/095014).

AA9 polypeptide enhancing activity can also be determined by incubating an AA9 polypeptide with 0.5% phosphoric acid swollen cellulose (PASC), 100 mM sodium acetate pH 5, 1 mM $MnSO_4$, 0.1% gallic acid, 0.025 mg/ml of *Aspergillus fumigatus* beta-glucosidase, and 0.01% TRITON® X-100 (4-(1,1,3,3-tetramethylbutyl)phenyl-polyethylene glycol) for 24-96 hours at 40° C. followed by determination of the glucose released from the PASC.

AA9 polypeptide enhancing activity can also be determined according to WO 2013/028928 for high temperature compositions.

AA9 polypeptides enhance the hydrolysis of a cellulosic material catalyzed by enzyme having cellulolytic activity by reducing the amount of cellulolytic enzyme required to reach the same degree of hydrolysis preferably at least 1.01-fold, e.g., at least 1.05-fold, at least 1.10-fold, at least 1.25-fold, at least 1.5-fold, at least 2-fold, at least 3-fold, at least 4-fold, at least 5-fold, at least 10-fold, or at least 20-fold.

The AA9 polypeptide can be used in the presence of a soluble activating divalent metal cation according to WO 2008/151043 or WO 2012/122518, e.g., manganese or copper.

The AA9 polypeptide can also be used in the presence of a dioxy compound, a bicylic compound, a heterocyclic compound, a nitrogen-containing compound, a quinone compound, a sulfur-containing compound, or a liquor obtained from a pretreated cellulosic material such as pretreated corn stover (WO 2012/021394, WO 2012/021395, WO 2012/021396, WO 2012/021399, WO 2012/021400, WO 2012/021401, WO 2012/021408, and WO 2012/021410).

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Beta-glucosidase: The term "beta-glucosidase" means a beta-D-glucoside glucohydrolase (E.C. 3.2.1.21) that catalyzes the hydrolysis of terminal non-reducing beta-D-glucose residues with the release of beta-D-glucose. Beta-glucosidase activity can be determined using p-nitrophenyl-beta-D-glucopyranoside as substrate according to the procedure of Venturi et al., 2002, *J. Basic Microbiol.* 42: 55-66. One unit of beta-glucosidase is defined as 1.0 µmole of p-nitrophenolate anion produced per minute at 25° C., pH 4.8 from 1 mM p-nitrophenyl-beta-D-glucopyranoside as substrate in 50 mM sodium citrate containing 0.01% TWEEN® 20.

Beta-xylosidase: The term "beta-xylosidase" means a beta-D-xyloside xylohydrolase (E.C. 3.2.1.37) that catalyzes the exo-hydrolysis of short beta (1→4)-xylooligosaccharides to remove successive D-xylose residues from non-reducing termini. Beta-xylosidase activity can be determined using 1 mM p-nitrophenyl-beta-D-xyloside as substrate in 100 mM sodium citrate containing 0.01% TWEEN® 20 at pH 5, 40° C. One unit of beta-xylosidase is defined as 1.0 µmole of p-nitrophenolate anion produced per minute at 40° C., pH 5 from 1 mM p-nitrophenyl-beta-D-xyloside in 100 mM sodium citrate containing 0.01% TWEEN® 20.

Carbohydrate binding module: The term "carbohydrate binding module" means a domain within a carbohydrate-active enzyme that provides carbohydrate-binding activity (Boraston et al., 2004, *Biochem. J.* 383: 769-781). A majority of known carbohydrate binding modules (CBMs) are contiguous amino acid sequences with a discrete fold. The carbohydrate binding module (CBM) is typically found either at the N-terminal or at the C-terminal extremity of an enzyme. Some CBMs are known to have specificity for cellulose. In an embodiment, the carbohydrate binding module has the sequence of amino acids 489-524 of SEQ ID NO: 1. In another embodiment, the carbohydrate binding module has the sequence of amino acids 461-497 of SEQ ID NO: 2. In another embodiment, the carbohydrate binding module has the sequence of amino acids 469-504 of SEQ ID NO: 4. In another embodiment, the carbohydrate binding module has the sequence of amino acids 472-507 of SEQ ID NO: 5. In another embodiment, the carbohydrate binding module has the sequence of amino acids 469-506 of SEQ ID NO: 6.

Catalase: The term "catalase" means a hydrogen-peroxide:hydrogen-peroxide oxidoreductase (E.C. 1.11.1.6 or E.C. 1.11.1.21) that catalyzes the conversion of two hydrogen peroxides to oxygen and two waters.

Catalase activity can be determined according to U.S. Pat. No. 5,646,025.

Catalase activity can also be determined by monitoring the degradation of hydrogen peroxide at 240 nm based on the following reaction:

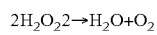

The reaction is conducted in 50 mM phosphate pH 7 at 25° C. with 10.3 mM substrate ($H_2O_2$). Absorbance is monitored spectrophotometrically within 16-24 seconds, which should correspond to an absorbance reduction from 0.45 to 0.4. One catalase activity unit can be expressed as one μmole of $H_2O_2$ degraded per minute at pH 7.0 and 25° C. or under the assay conditions.

Catalytic domain: The term "catalytic domain" means the region of an enzyme containing the catalytic machinery of the enzyme. In an embodiment, the catalytic domain has the sequence of amino acids 1-443 of SEQ ID NO: 1. In another embodiment, the catalytic domain has the sequence of amino acids 1-441 of SEQ ID NO: 2. In another embodiment, the catalytic domain has the sequence of amino acids 1-437 of SEQ ID NO: 3. In another embodiment, the catalytic domain has the sequence of amino acids 1-442 of SEQ ID NO: 4. In another embodiment, the catalytic domain has the sequence of amino acids 1-448 of SEQ ID NO: 5. In another embodiment, the catalytic domain has the sequence of amino acids 1-447 of SEQ ID NO: 6.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Cellobiohydrolase: The term "cellobiohydrolase" means a 1,4-beta-D-glucan cellobiohydrolase (E.C. 3.2.1.91 and E.C. 3.2.1.176) that catalyzes the hydrolysis of 1,4-beta-D-glucosidic linkages in cellulose, cellooligosaccharides, or any beta-1,4-linked glucose containing polymer, releasing cellobiose from the reducing end (cellobiohydrolase I) or non-reducing end (cellobiohydrolase II) of the chain (Teeri, 1997, *Trends in Biotechnology* 15: 160-167; Teeri et al., 1998, *Biochem. Soc. Trans.* 26: 173-178). Cellobiohydrolase activity can be determined according to the procedures described by WO 2011/153276, Lever et al., 1972, *Anal. Biochem.* 47: 273-279; van Tilbeurgh et al., 1982, *FEBS Letters* 149: 152-156; van Tilbeurgh and Claeyssens, 1985, *FEBS Letters* 187: 283-288; and Tomme et al., 1988, *Eur. J. Biochem.* 170: 575-581.

Cellulolytic enzyme or cellulase: The term "cellulolytic enzyme" or "cellulase" means one or more (e.g., several) enzymes that hydrolyze a cellulosic material. Such enzymes include endoglucanase(s), cellobiohydrolase(s), beta-glucosidase(s), or combinations thereof. The two basic approaches for measuring cellulolytic enzyme activity include: (1) measuring the total cellulolytic enzyme activity, and (2) measuring the individual cellulolytic enzyme activities (endoglucanases, cellobiohydrolases, and beta-glucosidases) as reviewed in Zhang et al., 2006, *Biotechnology Advances* 24: 452-481. Total cellulolytic enzyme activity can be measured using insoluble substrates, including Whatman N21 filter paper, microcrystalline cellulose, bacterial cellulose, algal cellulose, cotton, pretreated lignocellulose, etc. The most common total cellulolytic activity assay is the filter paper assay using Whatman N21 filter paper as the substrate. The assay was established by the International Union of Pure and Applied Chemistry (IUPAC) (Ghose, 1987, *Pure Appl. Chem.* 59: 257-68).

Cellulolytic enzyme activity can be determined by measuring the increase in production/release of sugars during hydrolysis of a cellulosic material by cellulolytic enzyme(s) under the following conditions: 1-50 mg of cellulolytic enzyme protein/g of cellulose in pretreated corn stover (PCS) (or other pretreated cellulosic material) for 3-7 days at a suitable temperature such as 25° C.-80° C., e.g., 25° C., 30° C., 35° C., 40° C., 45° C., 50° C., 55° C., 60° C., 65° C., 70° C., 75° C., or 80° C., and a suitable pH, such as 3-9, e.g., 3.0, 3.5, 4.0, 4.5, 5.0, 5.5, 6.0, 6.5, 7.0, 7.5, 8.0, 8.5, or 9.0, compared to a control hydrolysis without addition of cellulolytic enzyme protein. Typical conditions are 1 ml reactions, washed or unwashed PCS, 5% insoluble solids (dry weight), 50 mM sodium acetate pH 5, 1 mM $MnSO_4$, 50° C., 55° C., or 60° C., 72 hours, sugar analysis by AMINEX® HPX-87H column chromatography (Bio-Rad Laboratories, Inc.).

Cellulosic material: The term "cellulosic material" means any material containing cellulose. The predominant polysaccharide in the primary cell wall of biomass is cellulose, the second most abundant is hemicellulose, and the third is pectin. The secondary cell wall, produced after the cell has stopped growing, also contains polysaccharides and is strengthened by polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which help stabilize the cell wall matrix.

Cellulose is generally found, for example, in the stems, leaves, hulls, husks, and cobs of plants or leaves, branches, and wood of trees. The cellulosic material can be, but is not limited to, agricultural residue, herbaceous material (including energy crops), municipal solid waste, pulp and paper mill residue, waste paper, and wood (including forestry residue) (see, for example, Wiselogel et al., 1995, in Handbook on Bioethanol (Charles E. Wyman, editor), pp. 105-118, Taylor & Francis, Washington D.C.; Wyman, 1994, *Bioresource Technology* 50: 3-16; Lynd, 1990, *Applied Biochemistry and Biotechnology* 24/25: 695-719; Mosier et al., 1999, Recent Progress in Bioconversion of Lignocellulosics, in *Advances in Biochemical Engineering/Biotechnology*, T. Scheper, managing editor, Volume 65, pp. 23-40, Springer-Verlag, New York). It is understood herein that the cellulose may be in the form of lignocellulose, a plant cell wall material containing lignin, cellulose, and hemicellulose in a mixed matrix. In one aspect, the cellulosic material is any biomass material. In another aspect, the cellulosic material is lignocellulose, which comprises cellulose, hemicellulose, and lignin.

In an embodiment, the cellulosic material is agricultural residue, herbaceous material (including energy crops), municipal solid waste, pulp and paper mill residue, waste paper, or wood (including forestry residue).

In another embodiment, the cellulosic material is arundo, bagasse, bamboo, corn cob, corn fiber, corn stover, miscanthus, rice straw, sugar cane straw, switchgrass, or wheat straw.

In another embodiment, the cellulosic material is aspen, eucalyptus, fir, pine, poplar, spruce, or willow.

In another embodiment, the cellulosic material is algal cellulose, bacterial cellulose, cotton linter, filter paper, microcrystalline cellulose (e.g., AVICEL®), or phosphoric-acid treated cellulose.

In another embodiment, the cellulosic material is an aquatic biomass. As used herein the term "aquatic biomass" means biomass produced in an aquatic environment by a photosynthesis process. The aquatic biomass can be algae, emergent plants, floating-leaf plants, or submerged plants.

The cellulosic material may be used as is or may be subjected to pretreatment, using conventional methods known in the art, as described herein. In a preferred aspect, the cellulosic material is pretreated.

Coding sequence: The term "coding sequence" means a polynucleotide, which directly specifies the amino acid sequence of a variant. The boundaries of the coding sequence are generally determined by an open reading frame, which begins with a start codon such as ATG, GTG or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a variant of the present invention. Each control sequence may be native (i.e., from the same gene) or foreign (i.e., from a different gene) to the polynucleotide encoding the variant or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a variant.

Dissolved Oxygen Saturation Level: The saturation level of oxygen is determined at the standard partial pressure (0.21 atmosphere) of oxygen. The saturation level at the standard partial pressure of oxygen is dependent on the temperature and solute concentrations. In an embodiment where the temperature during hydrolysis or saccharification is 50° C., the saturation level would typically be in the range of 5-5.5 mg oxygen per kg slurry, depending on the solute concentrations. Hence, a concentration of dissolved oxygen of 0.5 to 10% of the saturation level at 50° C. corresponds to an amount of dissolved oxygen in a range from 0.025 ppm (0.5×5/100) to 0.55 ppm (10×5.5/100), such as, e.g., 0.05 to 0.165 ppm, and a concentration of dissolved oxygen of 10-70% of the saturation level at 50° C. corresponds to an amount of dissolved oxygen in a range from 0.50 ppm (10×5/100) to 3.85 ppm (70×5.5/100), such as, e.g., 1 to 2 ppm. In an embodiment, oxygen is added in an amount in the range of 0.5 to 5 ppm, such as 0.5 to 4.5 ppm, 0.5 to 4 ppm, 0.5 to 3.5 ppm, 0.5 to 3 ppm, 0.5 to 2.5 ppm, or 0.5 to 2 ppm. In one aspect, the dissolved oxygen concentration during saccharification is in the range of 0.5-10% of the saturation level, such as 0.5-7%, such as 0.5-5%, such as 0.5-4%, such as 0.5-3%, such as 0.5-2%, such as 1-5%, such as 1-4%, such as 1-3%, such as 1-2%.

Endoglucanase: The term "endoglucanase" means a 4-(1, 3;1,4)-beta-D-glucan 4-glucanohydrolase (E.C. 3.2.1.4) that catalyzes endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3-1,4 glucans such as cereal beta-D-glucans or xyloglucans, and other plant material containing cellulosic components. Endoglucanase activity can be determined by measuring reduction in substrate viscosity or increase in reducing ends determined by a reducing sugar assay (Zhang et al., 2006, *Biotechnology Advances* 24: 452-481). Endoglucanase activity can also be determined using carboxymethyl cellulose (CMC) as substrate according to the procedure of Ghose, 1987, *Pure and Appl. Chem.* 59: 257-268, at pH 5, 40° C.

Expression: The term "expression" includes any step involved in the production of a variant including, but not limited to, transcription, post-transcriptional modification, translation, post-translational modification, and secretion.

Expression vector: The term "expression vector" means a linear or circular DNA molecule that comprises a polynucleotide encoding a variant and is operably linked to control sequences that provide for its expression.

Feruloyl esterase: The term "feruloyl esterase" means a 4-hydroxy-3-methoxycinnamoyl-sugar hydrolase (EC 3.1.1.73) that catalyzes the hydrolysis of 4-hydroxy-3-methoxycinnamoyl (feruloyl) groups from esterified sugar, which is usually arabinose in natural biomass substrates, to produce ferulate (4-hydroxy-3-methoxycinnamate). Feruloyl esterase (FAE) is also known as ferulic acid esterase, hydroxycinnamoyl esterase, FAE-III, cinnamoyl ester hydrolase, FAEA, cinnAE, FAE-I, or FAE-II. Feruloyl esterase activity can be determined using 0.5 mM p-nitrophenylferulate as substrate in 50 mM sodium acetate pH 5.0. One unit of feruloyl esterase equals the amount of enzyme capable of releasing 1 μmole of p-nitrophenolate anion per minute at pH 5, 25° C.

Fragment: The term "fragment" means a polypeptide having one or more (e.g., several) amino acids absent from the amino and/or carboxyl terminus of a mature polypeptide; wherein the fragment has cellobiohydrolase activity. In one aspect, a fragment contains at least 380 amino acid residues, at least 400 amino acid residues, or at least 420 amino acid residues. In another aspect, a fragment contains at least 85% of the amino acid residues, e.g., at least 90% of the amino acid residues or at least 95% of the amino acid residues of the parent cellobiohydrolase.

Hemicellulolytic enzyme or hemicellulase: The term "hemicellulolytic enzyme" or "hemicellulase" means one or more (e.g., several) enzymes that hydrolyze a hemicellulosic material. See, for example, Shallom and Shoham, 2003, *Current Opinion In Microbiology* 6(3): 219-228). Hemicellulases are key components in the degradation of plant biomass. Examples of hemicellulases include, but are not limited to, an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. The substrates for these enzymes, hemicelluloses, are a heterogeneous group of branched and linear polysaccharides that are bound via hydrogen bonds to the cellulose microfibrils in the plant cell wall, crosslinking them into a robust network. Hemicelluloses are also covalently attached to lignin, forming together with cellulose a highly complex structure. The variable structure and organization of hemicelluloses require the concerted action of many enzymes for its complete degradation. The catalytic modules of hemicellulases are either glycoside hydrolases (GHs) that hydrolyze glycosidic bonds, or carbohydrate esterases (CEs), which hydrolyze ester linkages of acetate or ferulic acid side groups. These catalytic modules, based on homology of their primary sequence, can be assigned into GH and CE families. Some families, with an overall similar fold, can be further grouped into clans, marked alphabetically (e.g., GH-A). A most informative and updated classification of these and other carbohydrate active enzymes is available in the Carbohydrate-Active Enzymes (CAZy) database. Hemicellulolytic enzyme activities can be measured according to Ghose and Bisaria, 1987, *Pure & Appl. Chem.* 59: 1739-1752, at a suitable temperature such as 25° C.–80° C., e.g., 25° C., 30° C., 35° C., 40° C., 45° C., 50° C., 55° C., 60° C., 65° C., 70° C., 75° C., or 80° C., and a suitable pH such as 3-9, e.g., 3.0, 3.5, 4.0, 4.5, 5.0, 5.5, 6.0, 6.5, 7.0, 7.5, 8.0, 8.5, or 9.0.

Hemicellulosic material: The term "hemicellulosic material" means any material comprising hemicelluloses. Hemicelluloses include xylan, glucuronoxylan, arabinoxylan, glucomannan, and xyloglucan. These polysaccharides contain many different sugar monomers. Sugar monomers in hemicellulose can include xylose, mannose, galactose, rhamnose, and arabinose. Hemicelluloses contain most of the D-pentose sugars. Xylose is in most cases the sugar monomer present in the largest amount, although in softwoods mannose can be the most abundant sugar. Xylan contains a backbone of beta-(1-4)-linked xylose residues. Xylans of terrestrial plants are heteropolymers possessing a beta-(1-4)-D-xylopyranose backbone, which is branched by short carbohydrate chains. They comprise D-glucuronic acid or its 4-O-methyl ether, L-arabinose, and/or various oligosaccharides, composed of D-xylose, L-arabinose, D- or L-galactose, and D-glucose. Xylan-type polysaccharides can be divided into homoxylans and heteroxylans, which include glucuronoxylans, (arabino)glucuronoxylans, (glucurono) arabinoxylans, arabinoxylans, and complex heteroxylans. See, for example, Ebringerova et al., 2005, *Adv. Polym. Sci.* 186: 1-67. Hemicellulosic material is also known herein as "xylan-containing material".

Sources for hemicellulosic material are essentially the same as those for cellulosic material described herein.

In the processes of the present invention, any material containing hemicellulose may be used. In a preferred aspect, the hemicellulosic material is lignocellulose.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Improved property: The term "improved property" means a characteristic associated with a variant that is improved compared to the parent. Such improved properties include, but are not limited to, glucose tolerance, catalytic efficiency, catalytic rate, chemical stability, oxidation stability, pH activity, pH stability, specific activity, stability under storage conditions, substrate binding, substrate cleavage, substrate specificity, substrate stability, surface properties, thermal activity, and thermostability. In particular, the improved property is improved thermal activity and/or thermostability.

Increased thermal activity: The term "increased thermal activity" means a cellobiohydrolase variant enzyme displaying an alteration of the temperature-dependent activity profile at a specific temperature relative to the temperature-dependent activity profile of the parent cellobiohydrolase. The thermal activity value provides a measure of the enzyme's efficiency in performing catalysis of a hydrolysis reaction over a range of temperatures. A cellobiohydrolase has a specific temperature range wherein the protein is stable and retains its enzymatic activity, but becomes less stable and thus less active with increasing temperature. Furthermore, the initial rate of a reaction catalyzed by a cellobiohydrolase can be accelerated by an increase in temperature which is measured by determining thermal activity of a variant. A more thermoactive cellobiohydrolase variant will lead to an increase in the rate of hydrolysis decreasing the time required and/or decreasing the enzyme concentration required for hydrolysis. Alternatively, a cellobiohydrolase variant with a reduced thermal activity will catalyze a hydrolysis reaction at a temperature lower than the temperature optimum of the parent enzyme defined by the temperature-dependent activity profile of the parent.

The increased thermal activity of the variant relative to the parent can be determined by measuring the activity of a cellulase enzyme mixture containing either the variant enzyme or its parent in degrading cellulose at various temperatures, as described in Examples 34 through 44 of WO 2011/057140.

Increased thermostability: The term "increased thermostability" means a higher retention of cellobiohydrolase activity of a cellobiohydrolase variant after a period of incubation at a temperature relative to the parent. The increased thermostability of the variant relative to the parent can be assessed, for example, under conditions of one or more (e.g., several) temperatures. For example, the one or more (e.g., several) temperatures can be any temperature or temperatures in the range of 45° C. to 95° C., e.g., 45, 50, 55, 60, 65, 70, 75, 80, 85, or 95° C. (or in between, e.g., 62° C., 68° C., 72° C., etc.) at one or more (e.g., several) pHs in the range of 3 to 9, e.g., 3.0, 3.5, 4.0, 4.5, 5.0, 5.5, 6.0, 6.5, 7.0, 7.5, 8.0, 8.5, or 9.0 (or in between) for a suitable period (time) of incubation, e.g., 1 minute, 5 minutes, 10 minutes, 15 minutes, 20 minutes, 25 minutes, 30 minutes, 45 minutes, or 60 minutes (or in between, e.g., 23 minutes, 37 minutes, etc.), such that the variant retains residual activity. However, longer periods of incubation can also be used. The term "increased thermostability" can be used interchangeably with "improved thermostability".

The increased thermostability of the variant relative to the parent can be determined by differential scanning calorimetry (DSC) using methods standard in the art (see, for example, Sturtevant, 1987, *Annual Review of Physical Chemistry* 38: 463-488). The increased thermostability of the variant relative to the parent can also be determined using protein thermal unfolding analysis (see, for example, Example 6 herein). The increased thermostability of the variant relative to the parent can also be determined using any enzyme assay known in the art for cellobiohydrolases to measure residual activity after a temperature treatment. For example, residual enzyme activity can be measured using 4-methylumbelliferyl lactopyranoside (MUL) as described in WO 2011/153276.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance).

Laccase: The term "laccase" means a benzenediol:oxygen oxidoreductase (E.C. 1.10.3.2) that catalyzes the following reaction: 1,2- or 1,4-benzenediol+$O_2$=1,2- or 1,4-benzosemiquinone+$2H_2O$.

Laccase activity can be determined by the oxidation of syringaldazine (4,4''-[azinobis(methanylylidene)]bis(2,6-dimethoxyphenol)) to the corresponding quinone 4,4''-[azobis (methanylylidene)]bis(2,6-dimethoxycyclohexa-2,5-dien-1-one) by laccase. The reaction (shown below) is detected by an increase in absorbance at 530 nm.

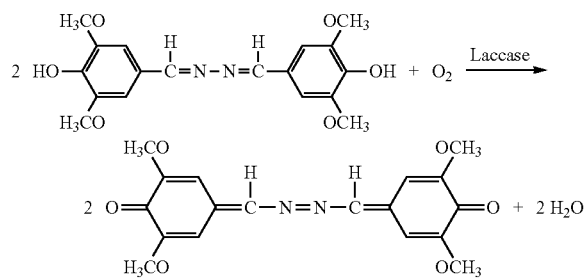

The reaction is conducted in 23 mM MES pH 5.5 at 30° C. with 19 µM substrate (syringaldazine) and 1 g/L polyethylene glycol (PEG) 6000. The sample is placed in a spectrophotometer and the change in absorbance is measured at 530 nm every 15 seconds up to 90 seconds. One laccase unit is the amount of enzyme that catalyzes the conversion of 1 µmole syringaldazine per minute under the specified analytical conditions.

Linker: The term "linker" means an amino acid sequence that links a carbohydrate binding module and a catalytic domain. In an embodiment, the linker has the sequence of amino acids 444-488 of SEQ ID NO: 1. In an embodiment, the linker has the sequence of amino acids 442-460 of SEQ ID NO: 2. In an embodiment, the linker has the sequence of amino acids 443-468 of SEQ ID NO: 4. In an embodiment, the linker has the sequence of amino acids 449-471 of SEQ ID NO: 5. In an embodiment, the linker has the sequence of amino acids 448-468 of SEQ ID NO: 6.

Mature polypeptide: The term "mature polypeptide" means a polypeptide in its final form following translation and any post-translational modifications, such as N-terminal processing, C-terminal truncation, glycosylation, phosphorylation, etc. It is known in the art that a host cell may produce a mixture of two of more different mature polypeptides (i.e., with a different C-terminal and/or N-terminal amino acid) expressed by the same polynucleotide. It is also known in the art that different host cells process polypeptides differently, and thus, one host cell expressing a polynucleotide may produce a different mature polypeptide (e.g., having a different C-terminal and/or N-terminal amino acid) as compared to another host cell expressing the same polynucleotide.

Mature polypeptide coding sequence: The term "mature polypeptide coding sequence" means a polynucleotide that encodes a mature polypeptide having cellobiohydrolase activity.

Mutant: The term "mutant" means a polynucleotide encoding a variant.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Parent or parent cellobiohydrolase: The term "parent" or "parent cellobiohydrolase" means a cellobiohydrolase to which an alteration, i.e., a substitution, insertion, and/or deletion, at one or more (e.g., several) positions, is made to produce the enzyme variants of the present invention. The parent may be a naturally occurring (wild-type) polypeptide or a variant or fragment thereof.

Peroxidase: The term "peroxidase" means an enzyme that converts a peroxide, e.g., hydrogen peroxide, to a less oxidative species, e.g., water. It is understood herein that a peroxidase encompasses a peroxide-decomposing enzyme. The term "peroxide-decomposing enzyme" is defined herein as a donor:peroxide oxidoreductase (E.C. number 1.11.1.x, wherein x=1-3, 5, 7-19, or 21) that catalyzes the reaction reduced substrate $(2e^-)$+ROOR'→oxidized substrate+ROH+R'OH; such as horseradish peroxidase that catalyzes the reaction phenol+$H_2O_2$→quinone+$H_2O$, and catalase that catalyzes the reaction $H_2O_2$+$H_2O_2$→$O_2$+$2H_2O$. In addition to hydrogen peroxide, other peroxides may also be decomposed by these enzymes.

Peroxidase activity can be determined by measuring the oxidation of 2,2'-azino-bis(3-ethylbenzthiazoline-6-sulfonic acid (ABTS) by a peroxidase in the presence of hydrogen peroxide as shown below. The reaction product $ABTS_{ox}$ forms a blue-green color which can be quantified at 418 nm.

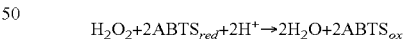

The reaction is conducted in 0.1 M phosphate pH 7 at 30° C. with 1.67 mM substrate (ABTS), 1.5 g/L TRITON® X-405, 0.88 mM hydrogen peroxide, and approximately 0.040 unit of enzyme per ml. The sample is placed in a spectrophotometer and the change in absorbance is measured at 418 nm from 15 seconds up to 60 seconds. One peroxidase unit can be expressed as the amount of enzyme required to catalyze the conversion of 1 µmole of hydrogen peroxide per minute under the specified analytical conditions.

Pretreated cellulosic or hemicellulosic material: The term "pretreated cellulosic or hemicellulosic material" means a cellulosic or hemicellulosic material derived from biomass by treatment with heat and dilute sulfuric acid, alkaline pretreatment, neutral pretreatment, or any pretreatment known in the art.

Pretreated corn stover: The term "Pretreated Corn Stover" or "PCS" means a cellulosic material derived from corn stover by treatment with heat and dilute sulfuric acid, alkaline pretreatment, neutral pretreatment, or any pretreatment known in the art.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are a gap open penalty of 10, a gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment–
Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are a gap open penalty of 10, a gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows: (Identical Deoxyribonucleotides×100)/(Length of Alignment–Total Number of Gaps in Alignment)

Subsequence: The term "subsequence" means a polynucleotide having one or more (e.g., several) nucleotides absent from the 5' and/or 3' end of a mature polypeptide coding sequence; wherein the subsequence encodes a fragment having cellobiohydrolase activity.

Variant: The term "variant" means a polypeptide having cellobiohydrolase activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position. The variants of the present invention have at least 20%, e.g., at least 40%, at least 50%, at least 60%, at least 70%, at least 80%, at least 90%, at least 95%, or at least 100% of the cellobiohydrolase activity of the polypeptide of SEQ ID NO: 1.

Wild-type cellobiohydrolase: The term "wild-type" cellobiohydrolase means a cellobiohydrolase produced by a naturally occurring microorganism, such as a bacterium, yeast, or filamentous fungus found in nature.

Xylan-containing material: The term "xylan-containing material" means any material comprising a plant cell wall polysaccharide containing a backbone of beta-(1-4)-linked xylose residues. Xylans of terrestrial plants are heteropolymers possessing a beta-(1-4)-D-xylopyranose backbone, which is branched by short carbohydrate chains. They comprise D-glucuronic acid or its 4-O-methyl ether, L-arabinose, and/or various oligosaccharides, composed of D-xylose, L-arabinose, D- or L-galactose, and D-glucose. Xylan-type polysaccharides can be divided into homoxylans and heteroxylans, which include glucuronoxylans, (arabino)glucuronoxylans, (glucurono)arabinoxylans, arabinoxylans, and complex heteroxylans. See, for example, Ebringerova et al., 2005, *Adv. Polym. Sci.* 186: 1-67.

In the processes of the present invention, any material containing xylan may be used. In a preferred aspect, the xylan-containing material is lignocellulose.

Xylan degrading activity or xylanolytic activity: The term "xylan degrading activity" or "xylanolytic activity" means a biological activity that hydrolyzes xylan-containing material. The two basic approaches for measuring xylanolytic activity include: (1) measuring the total xylanolytic activity, and (2) measuring the individual xylanolytic activities (e.g., endoxylanases, beta-xylosidases, arabinofuranosidases, alpha-glucuronidases, acetylxylan esterases, feruloyl esterases, and alpha-glucuronyl esterases). Recent progress in assays of xylanolytic enzymes was summarized in several publications including Biely and Puchard, 2006, *Journal of the Science of Food and Agriculture* 86(11): 1636-1647; Spanikova and Biely, 2006, *FEBS Letters* 580(19): 4597-4601; Herrmann et al., 1997, *Biochemical Journal* 321: 375-381.

Total xylan degrading activity can be measured by determining the reducing sugars formed from various types of xylan, including, for example, oat spelt, beechwood, and larchwood xylans, or by photometric determination of dyed xylan fragments released from various covalently dyed xylans. A common total xylanolytic activity assay is based on production of reducing sugars from polymeric 4-O-methyl glucuronoxylan as described in Bailey et al., 1992, Interlaboratory testing of methods for assay of xylanase activity, *Journal of Biotechnology* 23(3): 257-270. Xylanase activity can also be determined with 0.2% AZCL-arabinoxylan as substrate in 0.01% TRITON® X-100 and 200 mM sodium phosphate pH 6 at 37° C. One unit of xylanase activity is defined as 1.0 μmole of azurine produced per minute at 37° C., pH 6 from 0.2% AZCL-arabinoxylan as substrate in 200 mM sodium phosphate pH 6.

Xylan degrading activity can be determined by measuring the increase in hydrolysis of birchwood xylan (Sigma Chemical Co., Inc.) by xylan-degrading enzyme(s) under the following typical conditions: 1 ml reactions, 5 mg/ml substrate (total solids), 5 mg of xylanolytic protein/g of substrate, 50 mM sodium acetate pH 5, 50° C., 24 hours, sugar analysis using p-hydroxybenzoic acid hydrazide (PHBAH) assay as described by Lever, 1972, *Anal. Biochem.* 47: 273-279.

Xylanase: The term "xylanase" means a 1,4-beta-D-xylan-xylohydrolase (E.C. 3.2.1.8) that catalyzes the endohydrolysis of 1,4-beta-D-xylosidic linkages in xylans. Xylanase activity can be determined with 0.2% AZCL-arabinoxylan as substrate in 0.01% TRITON® X-100 and 200 mM sodium phosphate pH 6 at 37° C. One unit of xylanase activity is defined as 1.0 μmole of azurine produced per minute at 37° C., pH 6 from 0.2% AZCL-arabinoxylan as substrate in 200 mM sodium phosphate pH 6.

Reference to "about" a value or parameter herein includes aspects that are directed to that value or parameter per se. For example, description referring to "about X" includes the aspect "X".

As used herein and in the appended claims, the singular forms "a," "or," and "the" include plural referents unless the context clearly dictates otherwise. It is understood that the aspects of the invention described herein include "consisting" and/or "consisting essentially of" aspects.

Unless defined otherwise or clearly indicated by context, all technical and scientific terms used herein have the same meaning as commonly understood by one of ordinary skill in the art to which this invention belongs.

Conventions for Designation of Variants

For purposes of the present invention, the cellobiohydrolase of SEQ ID NO: 1 is used to determine the corresponding amino acid residue in another cellobiohydrolase. The amino acid sequence of another cellobiohydrolase is aligned with the cellobiohydrolase of SEQ ID NO: 1, and based on the alignment, the amino acid position number corresponding to any amino acid residue in the polypeptide of SEQ ID NO: 1 is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are a gap open penalty of 10, a gap extension penalty of 0.5, and the EBLOSUM62 (EMBOSS version of BLOSUM62) substitution matrix.

Identification of the corresponding amino acid residue in another cellobiohydrolase can be determined by alignment of multiple polypeptide sequences using several computer programs including, but not limited to MUSCLE (multiple sequence comparison by log-expectation; version 3.5 or later; Edgar, 2004, *Nucleic Acids Research* 32: 1792-1797); MAFFT (version 6.857 or later; Katoh and Kuma, 2002, *Nucleic Acids Research* 30: 3059-3066; Katoh et al., 2005, *Nucleic Acids Research* 33: 511-518; Katoh and Toh, 2007, *Bioinformatics* 23: 372-374; Katoh et al., 2009, *Methods in Molecular Biology* 537: 39-64; Katoh and Toh, 2010, *Bioinformatics* 26: 1899-1900), and EMBOSS EMMA employing ClustalW (1.83 or later; Thompson et al., 1994, *Nucleic Acids Research* 22: 4673-4680), using their respective default parameters.

When another cellobiohydrolase has diverged from the cellobiohydrolase of SEQ ID NO: 1 such that traditional sequence-based comparison fails to detect their relationship (Lindahl and Elofsson, 2000, *J. Mol. Biol.* 295: 613-615), other pairwise sequence comparison algorithms can be used. Greater sensitivity in sequence-based searching can be attained using search programs that utilize probabilistic representations of polypeptide families (profiles) to search databases. For example, the PSI-BLAST program generates profiles through an iterative database search process and can detect remote homologs (Atschul et al., 1997, *Nucleic Acids Res.* 25: 3389-3402). Even greater sensitivity can be achieved if the family or superfamily for the polypeptide has one or more representatives in the protein structure databases. Programs such as GenTHREADER (Jones, 1999, *J. Mol. Biol.* 287: 797-815; McGuffin and Jones, 2003, *Bioinformatics* 19: 874-881) utilize information from a variety of sources (PSI-BLAST, secondary structure prediction, structural alignment profiles, and solvation potentials) as input to a neural network that predicts the structural fold for a query sequence. Similarly, the method of Gough et al., 2000, *J. Mol. Biol.* 313: 903-919, can be used to align a sequence of unknown structure with the superfamily models present in the SCOP database. These alignments can in turn be used to generate homology models for the polypeptide, and such models can be assessed for accuracy using a variety of tools developed for that purpose. For proteins of known structure, several tools and resources are available for retrieving and generating structural alignments. For example, the SCOP superfamilies of proteins have been structurally aligned, and those alignments are accessible and downloadable. Two or more protein structures can be aligned using a variety of algorithms such as the distance alignment matrix (Holm and Sander, 1998, *Proteins* 33: 88-96) or combinatorial extension (Shindyalov and Bourne, 1998, *Protein Engineering* 11: 739-747), and implementation of these algorithms can additionally be utilized to query structure databases with a structure of interest to discover possible structural homologs (e.g., Holm and Park, 2000, *Bioinformatics* 16: 566-567).

In describing the variants of the present invention, the nomenclature described below is adapted for ease of reference. The accepted IUPAC single letter or three letter amino acid abbreviation is employed.

Substitutions.

For an amino acid substitution, the following nomenclature is used: Original amino acid, position, substituted amino acid. Accordingly, the substitution of threonine at position 226 with alanine is designated as "Thr226Ala" or "T226A". Multiple mutations are separated by addition marks ("+"), e.g., "Gly205Arg+Ser411Phe" or "G205R+S411F", representing substitutions at positions 205 and 411 of glycine (G) with arginine (R) and serine (S) with phenylalanine (F), respectively.

Deletions.

For an amino acid deletion, the following nomenclature is used: Original amino acid, position, *. Accordingly, the deletion of glycine at position 195 is designated as "Gly195*" or "G195*". Multiple deletions are separated by addition marks ("+"), e.g., "Gly195*+Ser411*" or "G195*+S411*".

Insertions.

For an amino acid insertion, the following nomenclature is used: Original amino acid, position, original amino acid, inserted amino acid. Accordingly, the insertion of lysine after glycine at position 195 is designated "Gly195GlyLys" or "G195GK". An insertion of multiple amino acids is designated [Original amino acid, position, original amino acid, inserted amino acid #1, inserted amino acid #2; etc.]. For example, the insertion of lysine and alanine after glycine at position 195 is indicated as "Gly195GlyLysAla" or "G195GKA".

In such cases the inserted amino acid residue(s) are numbered by the addition of lower case letters to the position number of the amino acid residue preceding the inserted amino acid residue(s). In the above example, the sequence would thus be:

| Parent: | Variant: |
|---|---|
| 195 | 195 195a 195b |
| G | G - K - A |

Multiple Alterations.

Variants comprising multiple alterations are separated by addition marks ("+"), e.g., "Arg170Tyr+Gly195Glu" or "R170Y+G195E" representing a substitution of arginine and glycine at positions 170 and 195 with tyrosine and glutamic acid, respectively.

Different Alterations.

Where different alterations can be introduced at a position, the different alterations are separated by a comma, e.g., "Arg170Tyr,Glu" represents a substitution of arginine at position 170 with tyrosine or glutamic acid. Thus, "Tyr167Gly,Ala+Arg170Gly,Ala" designates the following variants: "Tyr167Gly+Arg170Gly", "Tyr167Gly+Arg170Ala", "Tyr167Ala+Arg170Gly", and "Tyr167Ala+Arg170Ala".

DETAILED DESCRIPTION OF THE INVENTION

Variants

The present invention relates to isolated cellobiohydrolase variants, comprising a substitution at one or more (e.g., several) positions corresponding to positions 8, 17, 113, 157, 159, 184, 199, 240, 250, 274, 318, 325, 328, 347, 349, 358, 360, 380, 391, 393, 394, 412, and 430 of SEQ ID NO: 1, wherein the variants have cellobiohydrolase activity.

In an embodiment, the variant has a sequence identity of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to the amino acid sequence of the parent cellobiohydrolase or the mature polypeptide thereof.

In another embodiment, the variant comprises a catalytic domain having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to the catalytic domain of a parent cellobiohydrolase.

In another embodiment, the variant has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to the polypeptide of SEQ ID NO: 1.

In another embodiment, the variant has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to the polypeptide of SEQ ID NO: 2.

In another embodiment, the variant has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to the polypeptide of SEQ ID NO: 3.

In another embodiment, the variant has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to the polypeptide of SEQ ID NO: 4.

In another embodiment, the variant has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to the polypeptide of SEQ ID NO: 5.

In another embodiment, the variant has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to the polypeptide of SEQ ID NO: 6.

In one aspect, the number of alterations in the variants of the present invention is 1-23, e.g., 1, 2, 3, 4, 5, 6, 7, 8, 9, 10, 11, 12, 13, 4, 15, 16, 17, 18, 19, 20, 21, 22, or 23 alterations.

In another aspect, the variant comprises a substitution at one or more (e.g., several) positions corresponding to positions 8, 17, 113, 157, 159, 184, 199, 240, 250, 274, 318, 325, 328, 347, 349, 358, 360, 380, 391, 393, 394, 412, and 430 of SEQ ID NO: 1. In another aspect, a variant comprises a substitution at two positions corresponding to any of positions 8, 17, 113, 157, 159, 184, 199, 240, 250, 274, 318, 325, 328, 347, 349, 358, 360, 380, 391, 393, 394, 412, and 430. In another aspect, a variant comprises a substitution at three positions corresponding to any of positions 8, 17, 113, 157, 159, 184, 199, 240, 250, 274, 318, 325, 328, 347, 349, 358, 360, 380, 391, 393, 394, 412, and 430. In another aspect, a variant comprises a substitution at four positions corresponding to any of positions 8, 17, 113, 157, 159, 184, 199, 240, 250, 274, 318, 325, 328, 347, 349, 358, 360, 380, 391, 393, 394, 412, and 430. In another aspect, a variant comprises a substitution at five positions corresponding to any of positions 8, 17, 113, 157, 159, 184, 199, 240, 250, 274, 318, 325, 328, 347, 349, 358, 360, 380, 391, 393, 394, 412, and 430. In another aspect, a variant comprises a substitution at six positions corresponding to any of positions 8, 17, 113, 157, 159, 184, 199, 240, 250, 274, 318, 325, 328, 347, 349, 358, 360, 380, 391, 393, 394, 412, and 430. In another aspect, a variant comprises a substitution at seven positions corresponding to any of positions 8, 17, 113, 157, 159, 184, 199, 240, 250, 274, 318, 325, 328, 347, 349, 358, 360, 380, 391, 393, 394, 412, and 430. In another aspect, a variant comprises a substitution at eight positions corresponding to any of positions 8, 17, 113, 157, 159, 184, 199, 240, 250, 274, 318, 325, 328, 347, 349, 358, 360, 380, 391, 393, 394, 412, and 430. In another aspect, a variant comprises a substitution at nine positions corresponding to any of positions 8, 17, 113, 157, 159, 184, 199, 240, 250, 274, 318, 325, 328, 347, 349, 358, 360, 380, 391, 393, 394, 412, and 430. In another aspect, a variant comprises a substitution at ten positions corresponding to any of positions 8, 17, 113, 157, 159, 184, 199, 240, 250, 274, 318, 325, 328, 347, 349, 358, 360, 380, 391, 393, 394, 412, and 430. In another aspect, a variant comprises a substitution at eleven positions corresponding to any of positions 8, 17, 113, 157, 159, 184, 199, 240, 250, 274, 318, 325, 328, 347, 349, 358, 360, 380, 391, 393, 394, 412, and 430. In another aspect, a variant comprises a substitution at twelve positions corresponding to any of positions 8, 17, 113, 157, 159, 184, 199, 240, 250, 274, 318, 325, 328, 347, 349, 358, 360, 380, 391, 393, 394, 412, and 430. In another aspect, a variant comprises a substitution at thirteen positions corresponding to any of positions 8, 17, 113, 157, 159, 184, 199, 240, 250, 274, 318, 325, 328, 347, 349, 358, 360, 380, 391, 393, 394, 412, and 430. In another aspect, a variant comprises a substitution at fourteen positions corresponding to any of positions 8, 17, 113, 157, 159, 184, 199, 240, 250, 274, 318, 325, 328, 347, 349, 358, 360, 380, 391, 393, 394, 412, and 430. In another aspect, a variant comprises a substitution at fifteen positions corresponding to any of positions 8, 17, 113, 157, 159, 184, 199, 240, 250, 274, 318, 325, 328, 347, 349, 358, 360, 380, 391, 393, 394, 412, and 430. In another aspect, a variant comprises a substitution at sixteen positions corresponding to any of positions 8, 17, 113, 157, 159, 184, 199, 240, 250, 274, 318, 325, 328, 347, 349, 358, 360, 380, 391, 393, 394, 412, and 430. In another aspect, a variant comprises a substitution at seventeen positions corresponding to any of positions 8, 17, 113, 157, 159, 184, 199, 240, 250, 274, 318, 325, 328, 347, 349, 358, 360, 380, 391, 393, 394, 412, and 430. In another aspect, a variant comprises a substitution at eighteen positions corresponding to any of positions 8, 17, 113, 157, 159, 184, 199, 240, 250, 274, 318, 325, 328, 347, 349, 358, 360, 380, 391, 393, 394, 412, and 430. In another aspect, a variant comprises a substitution at nineteen positions corresponding to any of positions 8, 17, 113, 157, 159, 184, 199, 240, 250, 274, 318, 325, 328, 347, 349, 358, 360, 380, 391, 393, 394, 412, and 430. In another aspect, a variant comprises a substitution at twenty positions corresponding to any of positions 8, 17, 113, 157, 159, 184, 199, 240, 250, 274, 318, 325, 328, 347, 349, 358, 360, 380, 391, 393, 394, 412, and 430. In another aspect, a variant comprises a substitution at twenty-one positions corresponding to any of positions 8, 17, 113, 157, 159, 184, 199, 240, 250, 274, 318, 325, 328, 347, 349, 358, 360, 380, 391, 393, 394, 412, and 430. In another aspect, a variant comprises a substitution at twenty-two positions corresponding to any of positions 8, 17, 113, 157, 159, 184, 199, 240, 250, 274, 318, 325, 328, 347, 349, 358, 360, 380, 391, 393, 394, 412, and 430. In another aspect, a variant comprises a substitution at each position corresponding to positions 8, 17, 113, 157, 159, 184, 199, 240, 250, 274, 318, 325, 328, 347, 349, 358, 360, 380, 391, 393, 394, 412, and 430.

In another aspect, the variant comprises or consists of a substitution at a position corresponding to position 8 of SEQ ID NO: 1. In another aspect, the amino acid at a position corresponding to position 8 is substituted with Ala, Arg, Asn, Asp, Cys, Gln, Glu, Gly, His, Ile, Leu, Lys, Met, Phe, Pro, Ser, Trp, Tyr, or Val, e.g., Ala or Pro. In another aspect, the variant comprises or consists of the substitution of Thr→Ala or Pro at a position corresponding to position 8 of SEQ ID NO: 1 (e.g., T8A,P).

In another aspect, the variant comprises or consists of a substitution at a position corresponding to position 17 of SEQ ID NO: 1. In another aspect, the amino acid at a position corresponding to position 17 is substituted with Ala, Arg, Asn, Asp, Cys, Gln, Glu, Gly, His, Ile, Leu, Lys, Met, Phe, Pro, Thr, Trp, Tyr, or Val, e.g., Gln. In another aspect, the variant comprises or consists of the substitution of Ser→Gln at a position corresponding to position 17 of SEQ ID NO: 1 (e.g., S17Q).

In another aspect, the variant comprises or consists of a substitution at a position corresponding to position 113 of SEQ ID NO: 1. In another aspect, the amino acid at a position corresponding to position 113 is substituted with Ala, Arg, Asp, Cys, Gln, Glu, Gly, His, Ile, Leu, Lys, Met, Phe, Pro, Ser, Thr, Trp, Tyr, or Val, e.g., Asp. In another aspect, the variant comprises or consists of the substitution of Asn→Asp at a position corresponding to position 113 of SEQ ID NO: 1 (e.g., N113D).

In another aspect, the variant comprises or consists of a substitution at a position corresponding to position 157 of SEQ ID NO: 1. In another aspect, the amino acid at a position corresponding to position 157 is substituted with Ala, Arg, Asn, Asp, Cys, Gln, Glu, Gly, His, Ile, Leu, Met, Phe, Pro, Ser, Thr, Trp, Tyr, or Val, e.g., Arg. In another aspect, the variant comprises or consists of the substitution of Lys→Arg at a position corresponding to position 157 of SEQ ID NO: 1 (e.g., K157R).

In another aspect, the variant comprises or consists of a substitution at a position corresponding to position 159 of SEQ ID NO: 1. In another aspect, the amino acid at a position corresponding to position 159 is substituted with Ala, Arg, Asn, Asp, Cys, Gln, Glu, Gly, His, Ile, Leu, Lys, Met, Phe, Pro, Thr, Trp, Tyr, or Val, e.g., Pro. In another aspect, the variant comprises or consists of the substitution of Ser→Pro at a position corresponding to position 159 of SEQ ID NO: 1 (e.g., S159P).

In another aspect, the variant comprises or consists of a substitution at a position corresponding to position 184 of SEQ ID NO: 1. In another aspect, the amino acid at a position corresponding to position 184 is substituted with Ala, Arg, Asn, Cys, Gln, Glu, Gly, His, Ile, Leu, Lys, Met, Phe, Pro, Ser, Thr, Trp, Tyr, or Val, e.g., Asn. In another aspect, the variant comprises or consists of the substitution of Asp→Asn at a position corresponding to position 184 of SEQ ID NO: 1 (e.g., D184N).

In another aspect, the variant comprises or consists of a substitution at a position corresponding to position 199 of SEQ ID NO: 1. In another aspect, the amino acid at a position corresponding to position 199 is substituted with Ala, Arg, Asn, Asp, Cys, Gln, Glu, Gly, His, Ile, Leu, Lys, Met, Phe, Pro, Ser, Thr, Trp, or Tyr, e.g., Pro. In another aspect, the variant comprises or consists of the substitution of Val→Pro at a position corresponding to position 199 of SEQ ID NO: 1 (e.g., V199P).

In another aspect, the variant comprises or consists of a substitution at a position corresponding to position 240 of SEQ ID NO: 1. In another aspect, the amino acid at a position corresponding to position 240 is substituted with Ala, Arg, Asn, Asp, Cys, Gln, Gly, His, Ile, Leu, Lys, Met, Phe, Pro, Ser, Thr, Trp, Tyr, or Val, e.g., Gly. In another aspect, the variant comprises or consists of the substitution of Glu→Gly at a position corresponding to position 240 of SEQ ID NO: 1 (e.g., E240G).

In another aspect, the variant comprises or consists of a substitution at a position corresponding to position 250 of SEQ ID NO: 1. In another aspect, the amino acid at a position corresponding to position 250 is substituted with Ala, Arg, Asn, Asp, Cys, Gln, Glu, Gly, His, Ile, Leu, Lys, Met, Phe, Pro, Thr, Trp, Tyr, or Val, e.g., Asp. In another aspect, the variant comprises or consists of the substitution of Ser→Asp at a position corresponding to position 250 of SEQ ID NO: 1 (e.g., S250D).

In another aspect, the variant comprises or consists of a substitution at a position corresponding to position 274 of SEQ ID NO: 1. In another aspect, the amino acid at a position corresponding to position 274 is substituted with Ala, Arg, Asn, Asp, Cys, Gln, Glu, Gly, His, Ile, Leu, Lys, Met, Pro, Ser, Thr, Trp, Tyr, or Val, e.g., Tyr. In another aspect, the variant comprises or consists of the substitution of Phe→Tyr at a position corresponding to position 274 of SEQ ID NO: 1 (e.g., F274Y).

In another aspect, the variant comprises or consists of a substitution at a position corresponding to position 318 of SEQ ID NO: 1. In another aspect, the amino acid at a position corresponding to position 318 is substituted with Ala, Arg, Asn, Asp, Cys, Gln, Glu, His, Ile, Leu, Lys, Met, Phe, Pro, Ser, Thr, Trp, Tyr, or Val, e.g., Ala, Pro, or Ser. In another aspect, the variant comprises or consists of the substitution of Gly→Ala, Pro, or Ser at a position corresponding to position 318 of SEQ ID NO: 1 (e.g., G318A, P,S).

In another aspect, the variant comprises or consists of a substitution at a position corresponding to position 325 of SEQ ID NO: 1. In another aspect, the amino acid at a position corresponding to position 325 is substituted with Ala, Arg, Asn, Asp, Cys, Gln, Glu, Gly, His, Ile, Leu, Lys, Met, Phe, Pro, Ser, Trp, Tyr, or Val, e.g., Pro. In another aspect, the variant comprises or consists of the substitution of Thr→Pro at a position corresponding to position 325 of SEQ ID NO: 1 (e.g., T325P).

In another aspect, the variant comprises or consists of a substitution at a position corresponding to position 328 of SEQ ID NO: 1. In another aspect, the amino acid at a position corresponding to position 328 is substituted with Ala, Arg, Asn, Asp, Cys, Gln, Glu, Gly, His, Ile, Leu, Lys, Met, Phe, Pro, Ser, Trp, Tyr, or Val, e.g., Pro. In another aspect, the variant comprises or consists of the substitution of Thr→Pro at a position corresponding to position 328 of SEQ ID NO: 1 (e.g., T328P).

In another aspect, the variant comprises or consists of a substitution at a position corresponding to position 347 of SEQ ID NO: 1. In another aspect, the amino acid at a position corresponding to position 347 is substituted with Ala, Arg, Asn, Asp, Cys, Gln, Glu, Gly, His, Ile, Leu, Lys, Met, Phe, Pro, Ser, Trp, Tyr, or Val, e.g., Pro. In another aspect, the variant comprises or consists of the substitution of Thr→Pro at a position corresponding to position 347 of SEQ ID NO: 1 (e.g., T347P).

In another aspect, the variant comprises or consists of a substitution at a position corresponding to position 349 of SEQ ID NO: 1. In another aspect, the amino acid at a position corresponding to position 349 is substituted with Ala, Arg, Asn, Cys, Gln, Glu, Gly, His, Ile, Leu, Lys, Met, Phe, Pro, Ser, Thr, Trp, Tyr, or Val, e.g., Val. In another aspect, the variant comprises or consists of the substitution of Asp→Val at a position corresponding to position 349 of SEQ ID NO: 1 (e.g., D349V).

In another aspect, the variant comprises or consists of a substitution at a position corresponding to position 358 of SEQ ID NO: 1. In another aspect, the amino acid at a position corresponding to position 358 is substituted with Ala, Arg, Asn, Asp, Cys, Gln, Glu, His, Ile, Leu, Lys, Met, Phe, Pro, Ser, Thr, Trp, Tyr, or Val, e.g., Ala. In another aspect, the variant comprises or consists of the substitution of Gly→Ala at a position corresponding to position 358 of SEQ ID NO: 1 (e.g., G358A).

In another aspect, the variant comprises or consists of a substitution at a position corresponding to position 360 of SEQ ID NO: 1. In another aspect, the amino acid at a position corresponding to position 360 is substituted with Ala, Arg, Asn, Asp, Cys, Gln, Glu, His, Ile, Leu, Lys, Met, Phe, Pro, Ser, Thr, Trp, Tyr, or Val, e.g., Ser or Thr. In another aspect, the variant comprises or consists of the substitution of Gly→Ser or Thr at a position corresponding to position 360 of SEQ ID NO: 1 (e.g., G360S,T).

In another aspect, the variant comprises or consists of a substitution at a position corresponding to position 380 of SEQ ID NO: 1. In another aspect, the amino acid at a position corresponding to position 380 is substituted with Ala, Arg, Asn, Cys, Gln, Glu, Gly, His, Ile, Leu, Lys, Met, Phe, Pro, Ser, Thr, Trp, Tyr, or Val, e.g., Asn. In another aspect, the variant comprises or consists of the substitution of Asp→Asn at a position corresponding to position 380 of SEQ ID NO: 1 (e.g., D380N).

In another aspect, the variant comprises or consists of a substitution at a position corresponding to position 391 of SEQ ID NO: 1. In another aspect, the amino acid at a position corresponding to position 391 is substituted with Ala, Arg, Asp, Cys, Gln, Glu, Gly, His, Ile, Leu, Lys, Met, Phe, Pro, Ser, Thr, Trp, Tyr, or Val, e.g., Asp. In another aspect, the variant comprises or consists of the substitution of Asn→Asp at a position corresponding to position 391 of SEQ ID NO: 1 (e.g., N391D).

In another aspect, the variant comprises or consists of a substitution at a position corresponding to position 393 of SEQ ID NO: 1. In another aspect, the amino acid at a position corresponding to position 393 is substituted with Ala, Arg, Asn, Asp, Cys, Gln, Glu, Gly, His, Ile, Leu, Lys, Met, Phe, Pro, Thr, Trp, Tyr, or Val, e.g., Asp. In another aspect, the variant comprises or consists of the substitution of Ser→Asp at a position corresponding to position 393 of SEQ ID NO: 1 (e.g., S393D).

In another aspect, the variant comprises or consists of a substitution at a position corresponding to position 394 of SEQ ID NO: 1. In another aspect, the amino acid at a position corresponding to position 394 is substituted with Ala, Arg, Asn, Asp, Cys, Gln, Glu, Gly, His, Ile, Leu, Lys, Met, Phe, Pro, Thr, Trp, Tyr, or Val, e.g., Pro. In another aspect, the variant comprises or consists of the substitution of Ser→Pro at a position corresponding to position 394 of SEQ ID NO: 1 (e.g., S394P).

In another aspect, the variant comprises or consists of a substitution at a position corresponding to position 412 of SEQ ID NO: 1. In another aspect, the amino acid at a position corresponding to position 412 is substituted with Ala, Arg, Asn, Asp, Cys, Gln, Glu, Gly, His, Ile, Leu, Lys, Met, Phe, Pro, Ser, Trp, Tyr, or Val, e.g., Ala. In another aspect, the variant comprises or consists of the substitution of Thr→Ala at a position corresponding to position 412 of SEQ ID NO: 1 (e.g., T412A).

In another aspect, the variant comprises or consists of a substitution at a position corresponding to position 430 of SEQ ID NO: 1. In another aspect, the amino acid at a position corresponding to position 430 is substituted with Ala, Arg, Asn, Asp, Cys, Gln, Glu, Gly, His, Ile, Leu, Lys, Met, Phe, Pro, Ser, Trp, Tyr, or Val, e.g., Val. In another aspect, the variant comprises or consists of the substitution of Thr→Val at a position corresponding to position 430 of SEQ ID NO: 1 (e.g., T430V).

In another aspect, the variant comprises or consists of one or more (e.g., several) substitutions selected from the group consisting of T8A,P; S17Q; N113D; K157R; S159P; D184N; V199P; E240G; S250D; F274Y; G318A,P,S; T325P; T328P; T347P; D349V; G358A; G360S,T; D380N; N391D; S393D; S394P; T412A; and T430V at positions corresponding to SEQ ID NO: 1 in other cellobiohydrolases.

In each of the aspects below, the variant comprises or consists of the one or more (e.g., several) substitutions described below at positions corresponding to SEQ ID NO: 1 in other cellobiohydrolases, e.g., SEQ ID NOs: 2-6.

In another aspect, the variant comprises or consists of the substitutions S393D+S394P of SEQ ID NO: 1. In another aspect, the variant comprises or consists of the substitutions N391D+S393D+S394P of SEQ ID NO: 1. In another aspect, the variant comprises or consists of the substitutions T347P+D349V+N391D+S393D+S394P of SEQ ID NO: 1. In another aspect, the variant comprises or consists of the substitutions D349V+F274Y+N391D+S393D+S394P of SEQ ID NO: 1. In another aspect, the variant comprises or consists of the substitutions V199P+E240G+F274Y+T347P+D349V of SEQ ID NO: 1. 1. In another aspect, the variant comprises or consists of the substitutions V199P+ E240G+F274Y+G318P+T347P+D349V of SEQ ID NO: 1. In another aspect, the variant comprises or consists of the substitutions V199P+E240G+F274Y+T325P+T347P+ D349V of SEQ ID NO: 1. In another aspect, the variant comprises or consists of the substitutions V199P+E240G+ F274Y+G318P+T347P+D349V+N391D+S393D+S394P of SEQ ID NO: 1. In another aspect, the variant comprises or consists of the substitutions V199P+E240G+F274Y+ G318P+T347P+D349V+N391D+S393D+S394P+Y493W of SEQ ID NO: 1.

The variants may further comprise one or more additional alterations, e.g., substitutions, insertions, or deletions at one or more (e.g., several) other positions.

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, The Proteins, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for cellobiohydrolase activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

Additional guidance on the structure-activity relationship of the variants herein can be determined using published three-dimensional structure data for the Cel7A family of cellobiohydrolases (e.g., See, Moroz et al., 2015, *Acta Cryst.* F71: 114-120).

In one aspect, the variant further comprises an alteration at one or more (e.g., several) positions corresponding to positions 4, 21, 26, 38, 39, 44, 45, 46, 51, 52, 53, 54, 72, 75, 87, 93, 94, 95, 100, 102, 108, 111, 114, 129, 130, 131, 137, 138, 139, 144, 150, 156, 157, 183, 184, 187, 194, 195, 196, 197, 198, 199, 200, 201, 205, 206, 209, 211, 219, 237, 241, 247, 253, 260, 264, 271, 280, 320, 322, 330, 332, 343, 345, 350, 357, 358, 360, 365, 371, 375, 379, 380, 381, 382, 385, 386, 389, 390, 392, 397, 400, 405, 407, 413, 426, 427, 430, 440, 444, 445, 446, 447, 450, 453, 455, 456, 458, 459, 462, 463, 464, 492, 493, 494, 496, 497, 498, 502, 503, 507, 510, 513, 515, 516, and 517 of SEQ ID NO: 1, e.g., G4C, A21P, S26A, W38A, R39L, T44I, T44M, T44N, T44K, S45D, S45N, G46A, G46I, G46L, G46T, Y51I, T52R, T52W, G53A, G53M, G53R, G53W, N54S, N54I, N54D, A72C, G75S, S87T, L93V, N94S, N94A, N94R, N94Q, F95L, F95Y, S100T, S100V, S100W, S100L, S100G, K102S, K102R, L108I, L111T, D114E, F129S, D130N, D130E, V131A, P137S, C138S, G139E, G139M, G139Q, G139S, G139R, L144A, L144V, D150N, A156G, K157R, I183N, D184S, A187L, P194*, P194Q, S195*, T196*, N197A, N197*, D198A, D198*, V199*, N200A, N200G, N200W, N200F, N200C, N200*, S201*, N205R, H206Y, C209S, A211T, N219S, M237T, D241L, D241R, D241V, Y247C, A253D, A253R, G260D, N264Y, T271I, V280I, P320A, S322V, N330D, I332F, A343V, G345D, F350L, A357S, G358R, G360M, D365S, M371V, D375A, D375G, A379T, D380H, D380Y, M381V, L382A, D385E, S386C, S386E, P389L, P389Q, P389I, T390A, T390S, T390A, A392G, A392I, A392L, P397A, P397G, P397K, P397W, P397C, P397L, K400A, D405P, S407G, T413P, S426F, N427D, T430Y, T440L, T440R, T440G, T444S, T445D, S446T, S447L, T450D, S453D, T455A, T456S, S458E, K459E, K459S, S462I, T463I, T464A, T464A, H492L, Y493S, Y493W, A494D, A494S, C496S, C496Y, G497C, G498D, G498S, T502N, G503D, C507Y, P510V, P510S, C513R, C513W, K515D, Q516P, and N517D.

The variants may consist of 400 to 525, e.g., 400 to 500, 425 to 490, 450 to 480, 460 to 485 amino acids.

In an embodiment, the variant further comprises a linker, e.g., a foreign linker (a linker from a different parent).

In an embodiment, the variant further comprises a carbohydrate binding module, e.g., a foreign carbohydrate binding module (a carbohydrate binding module from a different parent).

In an embodiment, the variant has increased thermal activity compared to the parent enzyme.

In an embodiment, the variant has increased thermostability compared to the parent enzyme.

Parent Cellobiohydrolases

The parent cellobiohydrolase may be any cellobiohydrolase I.

In one embodiment, the parent cellobiohydrolase may be a polypeptide having at least 60% sequence identity to the polypeptide of SEQ ID NO: 1 or is a fragment of the polypeptide of SEQ ID NO: 1, which has cellobiohydrolase activity. In one aspect, the parent has a sequence identity to the polypeptide of SEQ ID NO: 1 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which have cellobiohydrolase activity. In another aspect, the amino acid sequence of the parent differs by up to 10 amino acids, e.g., 1, 2, 3, 4, 5, 6, 7, 8, 9, or 10, from the polypeptide of SEQ ID NO: 1.

In another embodiment, the parent cellobiohydrolase may be a polypeptide having at least 60% sequence identity to the polypeptide of SEQ ID NO: 2 or is a fragment of the polypeptide of SEQ ID NO: 2, which has cellobiohydrolase activity. In one aspect, the parent has a sequence identity to the polypeptide of SEQ ID NO: 2 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which have cellobiohydrolase activity. In another aspect, the amino acid sequence of the parent differs by up to 10 amino acids, e.g., 1, 2, 3, 4, 5, 6, 7, 8, 9, or 10, from the polypeptide of SEQ ID NO: 2.

In another embodiment, the parent cellobiohydrolase may be a polypeptide having at least 60% sequence identity to the polypeptide of SEQ ID NO: 3 or is a fragment of the polypeptide of SEQ ID NO: 3, which has cellobiohydrolase activity. In one aspect, the parent has a sequence identity to the polypeptide of SEQ ID NO: 3 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which have cellobiohydrolase activity. In another aspect, the amino acid sequence of the parent differs by up to 10 amino acids, e.g., 1, 2, 3, 4, 5, 6, 7, 8, 9, or 10, from the polypeptide of SEQ ID NO: 3.

In another embodiment, the parent cellobiohydrolase may be a polypeptide having at least 60% sequence identity to the polypeptide of SEQ ID NO: 4 or is a fragment of the polypeptide of SEQ ID NO: 4, which has cellobiohydrolase activity. In one aspect, the parent has a sequence identity to the polypeptide of SEQ ID NO: 4 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which have cellobiohydrolase activity. In another aspect, the amino acid sequence of the parent differs by up to 10 amino acids, e.g., 1, 2, 3, 4, 5, 6, 7, 8, 9, or 10, from the polypeptide of SEQ ID NO: 4.

In another embodiment, the parent cellobiohydrolase may be a polypeptide having at least 60% sequence identity to the polypeptide of SEQ ID NO: 5 or is a fragment of the polypeptide of SEQ ID NO: 5, which has cellobiohydrolase activity. In one aspect, the parent has a sequence identity to the polypeptide of SEQ ID NO: 5 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which have cellobiohydrolase activity. In another aspect, the amino acid sequence of the parent differs by up to 10 amino acids, e.g., 1, 2, 3, 4, 5, 6, 7, 8, 9, or 10, from the polypeptide of SEQ ID NO: 5.

In another embodiment, the parent cellobiohydrolase may be a polypeptide having at least 60% sequence identity to the polypeptide of SEQ ID NO: 6 or is a fragment of the polypeptide of SEQ ID NO: 6, which has cellobiohydrolase activity. In one aspect, the parent has a sequence identity to the polypeptide of SEQ ID NO: 6 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which have cellobiohydrolase activity. In another aspect, the amino acid sequence of the parent differs by up to 10 amino acids, e.g., 1, 2, 3, 4, 5, 6, 7, 8, 9, or 10, from the polypeptide of SEQ ID NO: 6.

In another aspect, the parent comprises or consists of the amino acid sequence of SEQ ID NO: 1. In another aspect, the parent comprises a catalytic domain having amino acids 1 to 443 of SEQ ID NO: 1.

In another aspect, the parent comprises or consists of the amino acid sequence of SEQ ID NO: 2. In another aspect, the parent comprises a catalytic domain having amino acids 1 to 441 of SEQ ID NO: 2.

In another aspect, the parent comprises or consists of the amino acid sequence of SEQ ID NO: 3.

In another aspect, the parent comprises or consists of the amino acid sequence of SEQ ID NO: 4. In another aspect, the parent comprises a catalytic domain having amino acids 1 to 442 of SEQ ID NO: 4.

In another aspect, the parent comprises or consists of the amino acid sequence of SEQ ID NO: 5. In another aspect, the parent comprises a catalytic domain having amino acids 1 to 448 of SEQ ID NO: 5.

In another aspect, the parent comprises or consists of the amino acid sequence of SEQ ID NO: 6. In another aspect, the parent comprises a catalytic domain having amino acids 1 to 447 of SEQ ID NO: 6.

In another aspect, the parent is a fragment of the polypeptide of SEQ ID NO: 1 containing at least 430 amino acid residues, e.g., at least 455 amino acid residues or at least 480 amino acid residues.

In another aspect, the parent is a fragment of the polypeptide of SEQ ID NO: 2 containing at 420 amino acid residues, e.g., at least 450 amino acid residues or at least 470 amino acid residues.

In another aspect, the parent is a fragment of the polypeptide of SEQ ID NO: 3 containing at 375 amino acid residues, e.g., at least 400 amino acid residues or at least 420 amino acid residues.

In another aspect, the parent is a fragment of the polypeptide of SEQ ID NO: 4 containing at least 370 amino acid residues, e.g., at least 390 amino acid residues or at least 415 amino acid residues.

In another aspect, the parent is a fragment of the polypeptide of SEQ ID NO: 5 containing at least 370 amino acid residues, e.g., at least 390 amino acid residues or at least 415 amino acid residues.

In another aspect, the parent is a fragment of the polypeptide of SEQ ID NO: 6 containing at least 370 amino acid residues, e.g., at least 390 amino acid residues or at least 415 amino acid residues.

A polynucleotide encoding the polypeptide of SEQ ID NO: 1, SEQ ID NO: 2, SEQ ID NO: 3, SEQ ID NO: 4, SEQ ID NO: 5, or SEQ ID NO: 6, or a subsequence thereof, may be used to design nucleic acid probes to identify and clone DNA encoding a parent from strains of different genera or species according to methods well known in the art. In particular, such probes can be used for hybridization with the genomic DNA or cDNA of a cell of interest, following standard Southern blotting procedures, to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}$P, $^{3}$H, $^{35}$S, biotin, or avidin). Such probes are encompassed by the present invention.

A genomic DNA or cDNA library prepared from such other strains may be screened for DNA that hybridizes with the probes described above and encodes a parent. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material.

In another embodiment, the parent is an allelic variant of the polypeptide of SEQ ID NO: 1, SEQ ID NO: 2, SEQ ID NO: 3, SEQ ID NO: 4, SEQ ID NO: 5, or SEQ ID NO: 6.

The polypeptide may be a hybrid polypeptide in which a region of one polypeptide is fused at the N-terminus or the C-terminus of a region of another polypeptide.

The parent may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, Proteins: Structure, *Function, and Genetics* 6: 240-248; and Stevens, 2003, *Drug Discovery World* 4: 35-48.

The parent may be a fungal cellobiohydrolase. For example, the parent may be a yeast cellobiohydrolase such as a *Candida*, *Kluyveromyces*, *Pichia*, *Saccharomyces*, *Schizosaccharomyces*, or *Yarrowia* cellobiohydrolase; or a filamentous fungal cellobiohydrolase such as an *Acremonium*, *Agaricus*, *Alternaria*, *Aspergillus*, *Aureobasidium*, *Botryosphaeria*, *Ceriporiopsis*, *Chaetomidium*, *Chrysosporium*, *Claviceps*, *Cochliobolus*, *Coprinopsis*, *Coptotermes*, *Corynascus*, *Cryphonectria*, *Cryptococcus*, *Dipodia*, *Exidia*, *Filibasidium*, *Fusarium*, *Gibberella*, *Holomastigotoides*, *Humicola*, *Irpex*, *Lentinula*, *Leptospaeria*, *Magnaporthe*, *Melanocarpus*, *Meripilus*, *Mucor*, *Myceliophthora*, *Neocallimastix*, *Neurospora*, *Paecilomyces*, *Penicillium*, *Phanerochaete*, *Piromyces*, *Poitrasia*, *Pseudoplectania*, *Pseudotrichonympha*, *Rhizomucor*, *Schizophyllum*, *Scytalidium*, *Talaromyces*, *Thermoascus*, *Thielavia*, *Tolypocladium*, *Trichoderma*, *Trichophaea*, *Verticillium*, *Volvariella*, or *Xylaria* cellobiohydrolase.

In another aspect, the parent is a *Saccharomyces carlsbergensis*, *Saccharomyces cerevisiae*, *Saccharomyces diastaticus*, *Saccharomyces douglasii*, *Saccharomyces kluyveri*, *Saccharomyces norbensis*, or *Saccharomyces oviformis* cellobiohydrolase.

In another aspect, the parent is an *Acremonium cellulolyticus*, *Aspergillus aculeatus*, *Aspergillus awamori*, *Aspergillus foetidus*, *Aspergillus fumigatus*, *Aspergillus japonicus*, *Aspergillus lentulus*, *Aspergillus nidulans*, *Aspergillus niger*, *Aspergillus oryzae*, *Aspergillus terreus*, *Chrysosporium inops*, *Chrysosporium keratinophilum*, *Chrysosporium lucknowense*, *Chrysosporium merdarium*, *Chrysosporium pannicola*, *Chrysosporium queenslandicum*, *Chrysosporium tropicum*, *Chrysosporium zonatum*, *Fennellia nivea*, *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium sulphureum*, *Fusarium torulosum*, *Fusarium trichothecioides*, *Fusarium venenatum*, *Humicola grisea*, *Humicola insolens*, *Humicola lanuginosa*, *Irpex lacteus*, *Mucor miehei*, *Myceliophthora thermophila*, *Neurospora crassa*, *Penicillium emersonii*, *Penicillium funiculosum*, *Penicillium pinophilum*, *Penicillium purpurogenum*, *Penicillium vasconiae*, *Phanerochaete chrysosporium*, *Talaromyces emersonii*, *Talaromyces leycettanus*, *Thermoascus aurantiacus*, *Thielavia achromatica*, *Thielavia albomyces*, *Thielavia albopilosa*, *Thielavia australeinsis*, *Thielavia fimeti*, *Thielavia microspora*, *Thielavia ovispora*, *Thielavia peruviana*, *Thielavia setosa*, *Thielavia spededonium*, *Thielavia subthermophila*, *Thielavia terrestris*, *Trichoderma harzianum*, *Trichoderma koningii*, *Trichoderma longibrachiatum*, *Trichoderma reesei*, or *Trichoderma viride* cellobiohydrolase.

In another aspect, the parent is a *Penicillium vasconiae* cellobiohydrolase, e.g., the cellobiohydrolase of SEQ ID NO: 1.

In another aspect, the parent is a *Trichoderma reesei* cellobiohydrolase, e.g., the cellobiohydrolase of SEQ ID NO: 2.

In another aspect, the parent is a *Penicillium emersonii* cellobiohydrolase, e.g., the cellobiohydrolase of SEQ ID NO: 3.

In another aspect, the parent is a *Penicillium occitanis* cellobiohydrolase, e.g., the cellobiohydrolase of SEQ ID NO: 4.

In another aspect, the parent is a *Talaromyces leycettanus* cellobiohydrolase, e.g., the cellobiohydrolase of SEQ ID NO: 5.

In another aspect, the parent is an *Aspergillus fumigatus* cellobiohydrolase, e.g., the cellobiohydrolase of SEQ ID NO: 6.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The parent may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding a parent may then be obtained by similarly screening a genomic DNA or cDNA library of another microorganism or mixed DNA sample. Once a polynucleotide encoding a parent has been detected with the probe(s), the polynucleotide can be isolated or cloned by utilizing techniques that are known to those of ordinary skill in the art (see, e.g., Sambrook et al., 1989, *Molecular Cloning, A Laboratory Manual*, 2d edition, Cold Spring Harbor, New York Preparation of Variants The present invention also relates to methods for obtaining a variant having cellobiohydrolase activity, comprising: (a) introducing into a parent cellobiohydrolase a substitution at one or more (e.g., several) positions corresponding to positions 8, 17, 113, 157, 159, 184, 199, 240, 250, 274, 318, 325, 328, 347, 349, 358, 360, 380, 391, 393, 394, 412, and 430 of SEQ ID NO: 1, wherein the variant has cellobiohydrolase activity; and optionally (b) recovering the variant.

In one aspect, the method further comprises introducing an alteration at one or more (e.g., several) positions corresponding to positions 4, 21, 26, 38, 39, 44, 45, 46, 51, 52, 53, 54, 72, 75, 87, 93, 94, 95, 100, 102, 108, 111, 114, 129, 130, 131, 137, 138, 139, 144, 150, 156, 157, 183, 184, 187, 194, 195, 196, 197, 198, 199, 200, 201, 205, 206, 209, 211, 219, 237, 241, 247, 253, 260, 264, 271, 280, 320, 322, 330, 332, 343, 345, 350, 357, 358, 360, 365, 371, 375, 379, 380, 381, 382, 385, 386, 389, 390, 390, 392, 397, 400, 405, 407, 413, 426, 427, 430, 440, 444, 445, 446, 447, 450, 453, 455, 456, 458, 459, 462, 463, 464, 492, 493, 494, 496, 497, 498, 502, 503, 507, 510, 513, 515, 516, and 517 of SEQ ID NO: 1, e.g., G4C, A21P, S26A, W38A, R39L, T44I, T44M, T44N, T44K, S45D, S45N, G46A, G46I, G46L, G46T, Y51I, T52R, T52W, G53A, G53M, G53R, G53W, N54S, N54I, N54D, A72C, G75S, S87T, L93V, N94S, N94A, N94R, N94Q, F95L, F95Y, S100T, S100V, S100W, S100L, S100G, K102S, K102R, L108I, L111T, D114E, F129S, D130N, D130E, V131A, P137S, C138S, G139E, G139M, G139Q, G139S, G139R, L144A, L144V, D150N, A156G, K157R, I183N, D184S, A187L, P194*, P194Q, S195*, T196*, N197A, N197*, D198A, D198*, V199*, N200A, N200G, N200W, N200F, N200C, N200*, S201*, N205R, H206Y, C209S, A211T, N219S, M237T, D241L, D241R, D241V, Y247C, A253D, A253R, G260D, N264Y, T271I, V280I, P320A, S322V, N330D, I332F, A343V, G345D, F350L, A357S, G358R, G360M, D365S, M371V, D375A, D375G, A379T, D380H, D380Y, M381V, L382A, D385E, S386C, S386E, P389L, P389Q, P389I, T390A, T390S, T390A, A392G, A392I, A392L, P397A, P397G, P397K, P397W, P397C, P397L, K400A, D405P, S407G, T413P, S426F, N427D, T430Y, T440L, T440R, T440G, T444S, T445D, S446T, S447L, T450D, S453D, T455A, T456S, S458E, K459E, K459S, S462I, T463I, T464A, T464A, H492L, Y493S, Y493W, A494D, A494S, C496S, C496Y, G497C, G498D, G498S, T502N, G503D, C507Y, P510V, P510S, C513R, C513W, K515D, Q516P, and N517D.

The variants can be prepared using any mutagenesis procedure known in the art, such as site-directed mutagenesis, synthetic gene construction, semi-synthetic gene construction, random mutagenesis, shuffling, etc.

Site-directed mutagenesis is a technique in which one or more (e.g., several) mutations are introduced at one or more defined sites in a polynucleotide encoding the parent. Any site-directed mutagenesis procedure can be used in the present invention. There are many commercial kits available that can be used to prepare variants.

Site-directed mutagenesis can be accomplished in vitro by PCR involving the use of oligonucleotide primers containing the desired mutation. Site-directed mutagenesis can also be performed in vitro by cassette mutagenesis involving the cleavage by a restriction enzyme at a site in the plasmid comprising a polynucleotide encoding the parent and subsequent ligation of an oligonucleotide containing the mutation in the polynucleotide. Usually the restriction enzyme that digests the plasmid and the oligonucleotide is the same, permitting sticky ends of the plasmid and the insert to ligate to one another. See, e.g., Scherer and Davis, 1979, *Proc. Natl. Acad. Sci. USA* 76: 4949-4955; and Barton et al., 1990, *Nucleic Acids Res.* 18: 7349-4966.

Site-directed mutagenesis can also be accomplished in vivo by methods known in the art. See, e.g., U.S. Patent Application Publication No. 2004/0171154; Storici et al., 2001, *Nature Biotechnol.* 19: 773-776; Kren et al., 1998, *Nat. Med.* 4: 285-290; and Calissano and Macino, 1996, *Fungal Genet. Newslett.* 43: 15-16.

Site-saturation mutagenesis systematically replaces a polypeptide coding sequence with sequences encoding all 19 amino acids at one or more (e.g., several) specific positions (Parikh and Matsumura, 2005, *J. Mol. Biol.* 352: 621-628).

Synthetic gene construction entails in vitro synthesis of a designed polynucleotide molecule to encode a polypeptide of interest. Gene synthesis can be performed utilizing several techniques, such as the multiplex microchip-based technology described by Tian et al. (2004, *Nature* 432: 1050-1054) and similar technologies wherein oligonucleotides are synthesized and assembled upon photo-programmable microfluidic chips.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204) and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

Semi-synthetic gene construction is accomplished by combining aspects of synthetic gene construction, and/or site-directed mutagenesis, and/or random mutagenesis, and/or shuffling. Semi-synthetic construction is typified by a process utilizing polynucleotide fragments that are synthesized, in combination with PCR techniques. Defined regions of genes may thus be synthesized de novo, while other regions may be amplified using site-specific mutagenic primers, while yet other regions may be subjected to error-prone PCR or non-error prone PCR amplification. Polynucleotide subsequences may then be shuffled.

Polynucleotides

The present invention also relates to isolated polynucleotides encoding a variant of the present invention.

Nucleic Acid Constructs

The present invention also relates to nucleic acid constructs comprising a polynucleotide encoding a variant of the present invention operably linked to one or more control sequences that direct the expression of the coding sequence in a suitable host cell under conditions compatible with the control sequences.

The polynucleotide may be manipulated in a variety of ways to provide for expression of a variant. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide recognized by a host cell for expression of a polynucleotide encoding a variant of the present invention. The promoter contains transcriptional control sequences that mediate the expression of the variant. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Dania (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof. Other promoters are described in U.S. Pat. No. 6,011,147.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator is operably linked to the 3'-terminus of the polynucleotide encoding the variant. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* acetamidase, *Aspergillus nidulans* anthranilate synthase, *Aspergillus niger* glucoamylase, *Aspergillus niger* alpha-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader is operably linked to the 5'-terminus of the polynucleotide encoding the variant. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a variant and directs the variant into the cell's secretory pathway. The 5'-end of the coding sequence of the polynucleotide may inherently contain a signal peptide coding sequence naturally linked in translation reading frame with the segment of the coding sequence that encodes the variant. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence to enhance secretion of the variant. However, any signal peptide coding sequence that directs the expressed variant into the secretory pathway of a host cell may be used.

Effective signal peptide coding sequences for bacterial host cells are the signal peptide coding sequences obtained from the genes for *Bacillus* NCI B 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a variant. The resultant polypeptide is known as a proenzyme or propolypeptide (or a zymogen in some cases). A propolypeptide is generally inactive and can be converted to an active variant by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a variant and the signal peptide sequence is positioned next to the N-terminus of the propeptide sequence.

It may also be desirable to add regulatory sequences that regulate expression of the variant relative to the growth of the host cell. Examples of regulatory sequences are those that cause expression of the gene to be turned on or off in response to a chemical or physical stimulus, including the presence of a regulatory compound. Regulatory sequences in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the variant would be operably linked to the regulatory sequence.

Expression Vectors

The present invention also relates to recombinant expression vectors comprising a polynucleotide encoding a variant of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the variant at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, adeA (phosphoribosylaminoim idazole-succinocarboxamide synthase), adeB (phosphoribosyl-aminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes.

The selectable marker may be a dual selectable marker system as described in WO 2010/039889. In one aspect, the dual selectable marker is a hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the variant or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAM1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a variant. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide encoding a variant of the present invention operably linked to one or more control sequences that direct the production of a variant of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the variant and its source.

The host cell may be any cell useful in the recombinant production of a variant, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell, including, but not limited to, *Streptomyces achromogenes*, *Streptomyces avermitilis*, *Streptomyces coelicolor*, *Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol. (Praha)* 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397), or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804), or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, Passmore, and Davenport, editors, *Soc. App. Bacteriol. Symposium Series* No. 9, 1980).

The yeast host cell may be a *Candida*, *Hansenula*, *Kluyveromyces*, *Pichia*, *Saccharomyces*, *Schizosaccharomyces*, or *Yarrowia* cell such as a *Kluyveromyces lactis*, *Saccharomyces carlsbergensis*, *Saccharomyces cerevisiae*, *Saccharomyces diastaticus*, *Saccharomyces douglasii*, *Saccharomyces kluyveri*, *Saccharomyces norbensis*, *Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium*, *Aspergillus*, *Aureobasidium*, *Bjerkandera*, *Ceriporiopsis*, *Chrysosporium*, *Coprinus*, *Coriolus*, *Cryptococcus*, *Filibasidium*, *Fusarium*, *Humicola*, *Magnaporthe*, *Mucor*, *Myceliophthora*, *Neocallimastix*, *Neurospora*, *Paecilomyces*, *Penicillium*, *Phanerochaete*, *Phlebia*, *Piromyces*, *Pleurotus*, *Schizophyllum*, *Talaromyces*, *Thermoascus*, *Thielavia*, *Tolypocladium*, *Trametes*, or *Trichoderma* cell.

For example, the filamentous fungal host cell may be an *Aspergillus awamori*, *Aspergillus foetidus*, *Aspergillus fumigatus*, *Aspergillus japonicus*, *Aspergillus nidulans*, *Aspergillus niger*, *Aspergillus oryzae*, *Bjerkandera adusta*, *Ceriporiopsis aneirina*, *Ceriporiopsis caregiea*, *Ceriporiopsis gilvescens*, *Ceriporiopsis pannocinta*, *Ceriporiopsis rivulosa*, *Ceriporiopsis subrufa*, *Ceriporiopsis subvermispora*, *Chrysosporium inops*, *Chrysosporium keratinophilum*, *Chrysosporium lucknowense*, *Chrysosporium merdarium*, *Chrysosporium pannicola*, *Chrysosporium queenslandicum*, *Chrysosporium tropicum*, *Chrysosporium zonatum*, *Coprinus cinereus*, *Coriolus hirsutus*, *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium sulphureum*, *Fusarium torulosum*, *Fusarium trichothecioides*, *Fusarium venenatum*, *Humicola insolens*, *Humicola lanuginosa*, *Mucor miehei*, *Myceliophthora thermophila*, *Neurospora crassa*, *Penicillium purpurogenum*, *Phanerochaete chrysosporium*, *Phlebia radiata*, *Pleurotus eryngii*, *Talaromyces emersonii*, *Thielavia terrestris*, *Trametes villosa*, *Trametes versicolor*, *Trichoderma harzianum*, *Trichoderma koningii*, *Trichoderma longibrachiatum*, *Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a variant, comprising (a) cultivating a recombinant host cell of the present invention under conditions conducive for production of the variant; and optionally (b) recovering the variant.

The host cells are cultivated in a nutrient medium suitable for production of the variant using methods known in the art. For example, the cells may be cultivated by multi-well plates such as 24, 48, or 96 well plates, shake flask cultivation, or small-scale or large-scale fermentation (including continuous, batch, fed-batch, or solid state fermentations) in laboratory or industrial fermentors in a suitable medium and under conditions allowing the variant to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the variant is secreted into the nutrient medium, the variant can be recovered directly from the medium. If the variant is not secreted, it can be recovered from cell lysates.

The variants may be detected using methods known in the art that are specific for the variants. These detection methods include, but are not limited to, use of specific antibodies, formation of an enzyme product, or disappearance of an enzyme substrate. For example, an enzyme assay may be used to determine the activity of the variant.

The variant may be recovered using methods known in the art. For example, the variant may be recovered from the nutrient medium by conventional procedures including, but not limited to, collection, centrifugation, filtration, extraction, spray-drying, evaporation, or precipitation. In one aspect, the whole fermentation broth is recovered.

The variant may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, Janson and Ryden, editors, VCH Publishers, New York, 1989) to obtain substantially pure variants.

In an alternative aspect, the variant is not recovered, but rather a host cell of the present invention expressing the variant is used as a source of the variant.

Fermentation Broth Formulations or Cell Compositions

The present invention also relates to a fermentation broth formulation or a cell composition comprising a variant of the present invention. The fermentation broth product further comprises additional ingredients used in the fermentation process, such as, for example, cells (including, the host cells containing the gene encoding the variant of the present invention which are used to produce the variant), cell debris, biomass, fermentation media and/or fermentation products. In some embodiments, the composition is a cell-killed whole broth containing organic acid(s), killed cells and/or cell debris, and culture medium.

The term "fermentation broth" refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In an embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid(s), and optionally further contains killed cells and/or cell debris. In one embodiment, the killed cells and/or cell debris are removed from a cell-killed whole broth to provide a composition that is free of these components.

The fermentation broth formulations or cell compositions may further comprise a preservative and/or anti-microbial (e.g., bacteriostatic) agent, including, but not limited to, sorbitol, sodium chloride, potassium sorbate, and others known in the art.

The fermentation broth formulations or cell compositions may further comprise multiple enzymatic activities, such as one or more (e.g., several) enzymes selected from the group consisting of a cellulase, a hemicellulase, a cellulose induced protein (CIP), an esterase, an expansin, a laccase, a ligninolytic enzyme, a pectinase, a peroxidase, a protease, and a swollenin. The fermentation broth formulations or cell compositions may also comprise one or more (e.g., several) enzymes selected from the group consisting of a hydrolase, an isomerase, a ligase, a lyase, an oxidoreductase, or a transferase, e.g., an alpha-galactosidase, alpha-glucosidase, aminopeptidase, amylase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or xylanase.

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis (e.g., expression of cellulase and/or glucosidase enzyme(s)). In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

Examples are given below of uses of the compositions of the present invention. The dosage of the composition and other conditions under which the composition is used may be determined based on methods known in the art.

Enzyme Compositions

The present invention also relates to compositions comprising a variant of the present invention. Preferably, the compositions are enriched in such a variant. The term "enriched" indicates that the cellobiohydrolase activity of the composition has been increased, e.g., with an enrichment factor of at least 1.1.

The compositions may comprise a variant of the present invention as the major enzymatic component, e.g., a mono-component composition. Alternatively, the compositions may comprise multiple enzymatic activities, such as one or more (e.g., several) enzymes selected from the group consisting of a cellulase, a hemicellulase, an AA9 polypeptide, a CIP, an esterase, an expansin, a laccase, a ligninolytic enzyme, a pectinase, a peroxidase, a protease, and a swollenin. The compositions may also comprise one or more (e.g., several) enzymes selected from the group consisting of a hydrolase, an isomerase, a ligase, a lyase, an oxidoreductase, or a transferase, e.g., an alpha-galactosidase, alpha-glucosidase, aminopeptidase, amylase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or xylanase.

The compositions may be prepared in accordance with methods known in the art and may be in the form of a liquid or a dry composition. The compositions may be stabilized in accordance with methods known in the art.

Examples are given below of uses of the compositions of the present invention. The dosage of the composition and other conditions under which the composition is used may be determined based on methods known in the art.

Examples are given below of preferred uses of the compositions of the present invention. The dosage of the composition and other conditions under which the composition is used may be determined based on methods known in the art.

Uses

The present invention is also directed to the following processes for using the variants having cellobiohydrolase activity, or compositions thereof.

The present invention also relates to processes for degrading a cellulosic material, comprising: treating the cellulosic material with an enzyme composition comprising a variant having cellobiohydrolase activity of the present invention. In one aspect, the processes further comprise recovering the degraded cellulosic material. Soluble products from the degradation of the cellulosic material can be separated from insoluble cellulosic material using a method known in the art such as, for example, centrifugation, filtration, or gravity settling.

The present invention also relates to processes of producing a fermentation product, comprising: (a) saccharifying a cellulosic material with an enzyme composition comprising a variant having cellobiohydrolase activity of the present invention; (b) fermenting the saccharified cellulosic material with one or more (e.g., several) fermenting microorganisms to produce the fermentation product; and (c) recovering the fermentation product from the fermentation.

The present invention also relates to processes of fermenting a cellulosic material, comprising: fermenting the cellulosic material with one or more (e.g., several) fermenting microorganisms, wherein the cellulosic material is saccharified with an enzyme composition comprising a variant having cellobiohydrolase activity of the present invention. In one aspect, the fermenting of the cellulosic material produces a fermentation product. In another aspect, the processes further comprise recovering the fermentation product from the fermentation.

The processes of the present invention can be used to saccharify the cellulosic material to fermentable sugars and to convert the fermentable sugars to many useful fermentation products, e.g., fuel (ethanol, n-butanol, isobutanol, biodiesel, jet fuel) and/or platform chemicals (e.g., acids, alcohols, ketones, gases, oils, and the like). The production of a desired fermentation product from the cellulosic material typically involves pretreatment, enzymatic hydrolysis (saccharification), and fermentation.

The processing of the cellulosic material according to the present invention can be accomplished using methods conventional in the art. Moreover, the processes of the present invention can be implemented using any conventional biomass processing apparatus configured to operate in accordance with the invention.

Hydrolysis (saccharification) and fermentation, separate or simultaneous, include, but are not limited to, separate hydrolysis and fermentation (SHF); simultaneous saccharification and fermentation (SSF); simultaneous saccharification and co-fermentation (SSCF); hybrid hydrolysis and fermentation (HHF); separate hydrolysis and co-fermentation (SHCF); hybrid hydrolysis and co-fermentation (HHCF); and direct microbial conversion (DMC), also sometimes called consolidated bioprocessing (CBP). SHF uses separate process steps to first enzymatically hydrolyze the cellulosic material to fermentable sugars, e.g., glucose, cellobiose, and pentose monomers, and then ferment the fermentable sugars to ethanol. In SSF, the enzymatic hydrolysis of the cellulosic material and the fermentation of sugars to ethanol are combined in one step (Philippidis, G. P., 1996, Cellulose bioconversion technology, in *Handbook on Bioethanol: Production and Utilization*, Wyman, C. E., ed., Taylor & Francis, Washington, DC, 179-212). SSCF involves the co-fermentation of multiple sugars (Sheehan and Himmel, 1999, *Biotechnol. Prog.* 15: 817-827). HHF involves a separate hydrolysis step, and in addition a simultaneous saccharification and hydrolysis step, which can be carried out in the same reactor. The steps in an HHF process can be carried out at different temperatures, i.e., high temperature enzymatic saccharification followed by SSF at a lower temperature that the fermentation strain can tolerate. DMC combines all three processes (enzyme production, hydrolysis, and fermentation) in one or more (e.g., several) steps where the same organism is used to produce the enzymes for conversion of the cellulosic material to fermentable sugars and to convert the fermentable sugars into a final product (Lynd et al., 2002, *Microbiol. Mol. Biol. Reviews* 66: 506-577). It is understood herein that any method known in the art comprising pretreatment, enzymatic hydrolysis (saccharification), fermentation, or a combination thereof, can be used in the practicing the processes of the present invention.

A conventional apparatus can include a fed-batch stirred reactor, a batch stirred reactor, a continuous flow stirred reactor with ultrafiltration, and/or a continuous plug-flow column reactor (de Castilhos Corazza et al., 2003, *Acta Scientiarum. Technology* 25: 33-38; Gusakov and Sinitsyn, 1985, *Enz. Microb. Technol.* 7: 346-352), an attrition reactor (Ryu and Lee, 1983, *Biotechnol. Bioeng.* 25: 53-65). Additional reactor types include fluidized bed, upflow blanket, immobilized, and extruder type reactors for hydrolysis and/or fermentation.

Pretreatment.

In practicing the processes of the present invention, any pretreatment process known in the art can be used to disrupt plant cell wall components of the cellulosic material (Chandra et al., 2007, *Adv. Biochem. Engin./Biotechnol.* 108: 67-93; Galbe and Zacchi, 2007, *Adv. Biochem. Engin./Biotechnol.* 108: 41-65; Hendriks and Zeeman, 2009, *Bioresource Technology* 100: 10-18; Mosier et al., 2005, *Bioresource Technology* 96: 673-686; Taherzadeh and Karimi, 2008, *Int. J. Mol. Sci.* 9: 1621-1651; Yang and Wyman, 2008, *Biofuels Bioproducts and Biorefining-Biofpr.* 2: 26-40).

The cellulosic material can also be subjected to particle size reduction, sieving, pre-soaking, wetting, washing, and/or conditioning prior to pretreatment using methods known in the art.

Conventional pretreatments include, but are not limited to, steam pretreatment (with or without explosion), dilute acid pretreatment, hot water pretreatment, alkaline pretreatment, lime pretreatment, wet oxidation, wet explosion, ammonia fiber explosion, organosolv pretreatment, and biological pretreatment. Additional pretreatments include ammonia percolation, ultrasound, electroporation, microwave, supercritical $CO_2$, supercritical $H_2O$, ozone, ionic liquid, and gamma irradiation pretreatments.

The cellulosic material can be pretreated before hydrolysis and/or fermentation. Pretreatment is preferably performed prior to the hydrolysis. Alternatively, the pretreatment can be carried out simultaneously with enzyme hydrolysis to release fermentable sugars, such as glucose, xylose, and/or cellobiose. In most cases the pretreatment step itself results in some conversion of biomass to fermentable sugars (even in absence of enzymes).

Steam Pretreatment. In steam pretreatment, the cellulosic material is heated to disrupt the plant cell wall components, including lignin, hemicellulose, and cellulose to make the cellulose and other fractions, e.g., hemicellulose, accessible to enzymes. The cellulosic material is passed to or through a reaction vessel where steam is injected to increase the temperature to the required temperature and pressure and is retained therein for the desired reaction time. Steam pretreatment is preferably performed at 140-250° C., e.g., 160-200° C. or 170-190° C., where the optimal temperature range depends on optional addition of a chemical catalyst. Residence time for the steam pretreatment is preferably 1-60 minutes, e.g., 1-30 minutes, 1-20 minutes, 3-12 minutes, or 4-10 minutes, where the optimal residence time depends on the temperature and optional addition of a chemical catalyst. Steam pretreatment allows for relatively high solids loadings, so that the cellulosic material is generally only moist during the pretreatment. The steam pretreatment is often combined with an explosive discharge of the material after the pretreatment, which is known as steam explosion, that is, rapid flashing to atmospheric pressure and turbulent flow of the material to increase the accessible surface area by fragmentation (Duff and Murray, 1996, *Bioresource Technology* 855: 1-33; Galbe and Zacchi, 2002, *Appl. Microbiol. Biotechnol.* 59: 618-628; U.S. Patent Application No. 2002/0164730). During steam pretreatment, hemicellulose acetyl groups are cleaved and the resulting acid autocatalyzes partial hydrolysis of the hemicellulose to monosaccharides and oligosaccharides. Lignin is removed to only a limited extent.

Chemical Pretreatment. The term "chemical treatment" refers to any chemical pretreatment that promotes the separation and/or release of cellulose, hemicellulose, and/or lignin. Such a pretreatment can convert crystalline cellulose to amorphous cellulose. Examples of suitable chemical pretreatment processes include, for example, dilute acid pretreatment, lime pretreatment, wet oxidation, ammonia fiber/freeze expansion (AFEX), ammonia percolation (APR), ionic liquid, and organosolv pretreatments.

A chemical catalyst such as $H_2SO_4$ or $SO_2$ (typically 0.3 to 5% w/w) is sometimes added prior to steam pretreatment, which decreases the time and temperature, increases the recovery, and improves enzymatic hydrolysis (Ballesteros et al., 2006, *Appl. Biochem. Biotechnol.* 129-132: 496-508; Varga et al., 2004, *Appl. Biochem. Biotechnol.* 113-116: 509-523; Sassner et al., 2006, *Enzyme Microb. Technol.* 39: 756-762). In dilute acid pretreatment, the cellulosic material is mixed with dilute acid, typically $H_2SO_4$, and water to form a slurry, heated by steam to the desired temperature, and after a residence time flashed to atmospheric pressure. The dilute acid pretreatment can be performed with a number of reactor designs, e.g., plug-flow reactors, counter-current reactors, or continuous counter-current shrinking bed reactors (Duff and Murray, 1996, *Bioresource Technology* 855: 1-33; Schell et al., 2004, *Bioresource Technology* 91: 179-188; Lee et al., 1999, *Adv. Biochem. Eng. Biotechnol.* 65: 93-115).

Several methods of pretreatment under alkaline conditions can also be used. These alkaline pretreatments include, but are not limited to, sodium hydroxide, lime, wet oxidation, ammonia percolation (APR), and ammonia fiber/freeze expansion (AFEX) pretreatment.

Lime pretreatment is performed with calcium oxide or calcium hydroxide at temperatures of 85-150° C. and residence times from 1 hour to several days (Wyman et al., 2005, *Bioresource Technology* 96: 1959-1966; Mosier et al., 2005, *Bioresource Technology* 96: 673-686). WO 2006/110891, WO 2006/110899, WO 2006/110900, and WO 2006/110901 disclose pretreatment methods using ammonia.

Wet oxidation is a thermal pretreatment performed typically at 180-200° C. for 5-15 minutes with addition of an oxidative agent such as hydrogen peroxide or over-pressure of oxygen (Schmidt and Thomsen, 1998, *Bioresource Technology* 64: 139-151; Palonen et al., 2004, *Appl. Biochem. Biotechnol.* 117: 1-17; Varga et al., 2004, *Biotechnol. Bioeng.* 88: 567-574; Martin et al., 2006, *J. Chem. Technol. Biotechnol.* 81: 1669-1677). The pretreatment is performed preferably at 1-40% dry matter, e.g., 2-30% dry matter or 5-20% dry matter, and often the initial pH is increased by the addition of alkali such as sodium carbonate.

A modification of the wet oxidation pretreatment method, known as wet explosion (combination of wet oxidation and steam explosion) can handle dry matter up to 30%. In wet explosion, the oxidizing agent is introduced during pretreatment after a certain residence time. The pretreatment is then ended by flashing to atmospheric pressure (WO 2006/032282).

Ammonia fiber expansion (AFEX) involves treating the cellulosic material with liquid or gaseous ammonia at moderate temperatures such as 90-150° C. and high pressure such as 17-20 bar for 5-10 minutes, where the dry matter content can be as high as 60% (Gollapalli et al., 2002, *Appl. Biochem. Biotechnol.* 98: 23-35; Chundawat et al., 2007, *Biotechnol. Bioeng.* 96: 219-231; Alizadeh et al., 2005, *Appl. Biochem. Biotechnol.* 121: 1133-1141; Teymouri et al., 2005, *Bioresource Technology* 96: 2014-2018). During AFEX pretreatment cellulose and hemicelluloses remain relatively intact. Lignin-carbohydrate complexes are cleaved.

Organosolv pretreatment delignifies the cellulosic material by extraction using aqueous ethanol (40-60% ethanol) at 160-200° C. for 30-60 minutes (Pan et al., 2005, *Biotechnol. Bioeng.* 90: 473-481; Pan et al., 2006, *Biotechnol. Bioeng.*

94: 851-861; Kurabi et al., 2005, *Appl. Biochem. Biotechnol.* 121: 219-230). Sulphuric acid is usually added as a catalyst. In organosolv pretreatment, the majority of hemicellulose and lignin is removed.

Other examples of suitable pretreatment methods are described by Schell et al., 2003, *Appl. Biochem. Biotechnol.* 105-108: 69-85, and Mosier et al., 2005, *Bioresource Technology* 96: 673-686, and U.S. Published Application 2002/0164730.

In one aspect, the chemical pretreatment is preferably carried out as a dilute acid treatment, and more preferably as a continuous dilute acid treatment. The acid is typically sulfuric acid, but other acids can also be used, such as acetic acid, citric acid, nitric acid, phosphoric acid, tartaric acid, succinic acid, hydrogen chloride, or mixtures thereof. Mild acid treatment is conducted in the pH range of preferably 1-5, e.g., 1-4 or 1-2.5. In one aspect, the acid concentration is in the range from preferably 0.01 to 10 wt. % acid, e.g., 0.05 to 5 wt. % acid or 0.1 to 2 wt. % acid. The acid is contacted with the cellulosic material and held at a temperature in the range of preferably 140-200° C., e.g., 165-190° C., for periods ranging from 1 to 60 minutes.

In another aspect, pretreatment takes place in an aqueous slurry. In preferred aspects, the cellulosic material is present during pretreatment in amounts preferably between 10-80 wt. %, e.g., 20-70 wt. % or 30-60 wt. %, such as around 40 wt. %. The pretreated cellulosic material can be unwashed or washed using any method known in the art, e.g., washed with water.

Mechanical Pretreatment or Physical Pretreatment: The term "mechanical pretreatment" or "physical pretreatment" refers to any pretreatment that promotes size reduction of particles. For example, such pretreatment can involve various types of grinding or milling (e.g., dry milling, wet milling, or vibratory ball milling).

The cellulosic material can be pretreated both physically (mechanically) and chemically. Mechanical or physical pretreatment can be coupled with steaming/steam explosion, hydrothermolysis, dilute or mild acid treatment, high temperature, high pressure treatment, irradiation (e.g., microwave irradiation), or combinations thereof. In one aspect, high pressure means pressure in the range of preferably about 100 to about 400 psi, e.g., about 150 to about 250 psi. In another aspect, high temperature means temperature in the range of about 100 to about 300° C., e.g., about 140 to about 200° C. In a preferred aspect, mechanical or physical pretreatment is performed in a batch-process using a steam gun hydrolyzer system that uses high pressure and high temperature as defined above, e.g., a Sunds Hydrolyzer available from Sunds Defibrator AB, Sweden. The physical and chemical pretreatments can be carried out sequentially or simultaneously, as desired.

Accordingly, in a preferred aspect, the cellulosic material is subjected to physical (mechanical) or chemical pretreatment, or any combination thereof, to promote the separation and/or release of cellulose, hemicellulose, and/or lignin.

Biological Pretreatment. The term "biological pretreatment" refers to any biological pretreatment that promotes the separation and/or release of cellulose, hemicellulose, and/or lignin from the cellulosic material. Biological pretreatment techniques can involve applying lignin-solubilizing microorganisms and/or enzymes (see, for example, Hsu, T.-A., 1996, Pretreatment of biomass, in *Handbook on Bioethanol: Production and Utilization*, Wyman, C. E., ed., Taylor & Francis, Washington, DC, 179-212; Ghosh and Singh, 1993, *Adv. Appl. Microbiol.* 39: 295-333; McMillan, J. D., 1994, Pretreating lignocellulosic biomass: a review, in *Enzymatic Conversion of Biomass for Fuels Production*, Himmel, M. E., Baker, J. O., and Overend, R. P., eds., ACS Symposium Series 566, American Chemical Society, Washington, DC, chapter 15; Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Olsson and Hahn-Hagerdal, 1996, *Enz. Microb. Tech.* 18: 312-331; and Vallander and Eriksson, 1990, *Adv. Biochem. Eng./Biotechnol.* 42: 63-95).

Saccharification.

In the hydrolysis step, also known as saccharification, the cellulosic material, e.g., pretreated, is hydrolyzed to break down cellulose and/or hemicellulose to fermentable sugars, such as glucose, cellobiose, xylose, xylulose, arabinose, mannose, galactose, and/or soluble oligosaccharides. The hydrolysis is performed enzymatically by one or more enzyme compositions in one or more stages. The hydrolysis can be carried out as a batch process or series of batch processes. The hydrolysis can be carried out as a fed batch or continuous process, or series of fed batch or continuous processes, where the cellulosic material is fed gradually to, for example, a hydrolysis solution containing an enzyme composition. In an embodiment, the saccharification is a continuous saccharification in which a cellulosic material and a cellulolytic enzyme composition are added at different intervals throughout the saccharification and the hydrolysate is removed at different intervals throughout the saccharification. The removal of the hydrolysate may occur prior to, simultaneously with, or after the addition of the cellulosic material and the cellulolytic enzyme composition.

Enzymatic hydrolysis is preferably carried out in a suitable aqueous environment under conditions that can be readily determined by one skilled in the art. In one aspect, hydrolysis is performed under conditions suitable for the activity of the enzymes(s), i.e., optimal for the enzyme(s).

The saccharification is generally performed in stirred-tank reactors or fermentors under controlled pH, temperature, and mixing conditions. Suitable process time, temperature and pH conditions can readily be determined by one skilled in the art. For example, the total saccharification time can last up to 200 hours, but is typically performed for preferably about 4 to about 120 hours, e.g., about 12 to about 96 hours or about 24 to about 72 hours. The temperature is in the range of preferably about 25° C. to about 80° C., e.g., about 30° C. to about 70° C., about 40° C. to about 60° C., or about 50° C. to about 55° C. The pH is in the range of preferably about 3 to about 9, e.g., about 3.5 to about 8, about 4 to about 7, about 4.2 to about 6, or about 4.3 to about 5.5.

The dry solids content is in the range of preferably about 5 to about 50 wt. %, e.g., about 10 to about 40 wt. % or about 20 to about 30 wt. %.

In one aspect, the saccharification is performed in the presence of dissolved oxygen at a concentration of at least 0.5% of the saturation level.

In an embodiment of the invention the dissolved oxygen concentration during saccharification is in the range of at least 0.5% up to 30% of the saturation level, such as at least 1% up to 25%, at least 1% up to 20%, at least 1% up to 15%, at least 1% up to 10%, at least 1% up to 5%, and at least 1% up to 3% of the saturation level. In a preferred embodiment, the dissolved oxygen concentration is maintained at a concentration of at least 0.5% up to 30% of the saturation level, such as at least 1% up to 25%, at least 1% up to 20%, at least 1% up to 15%, at least 1% up to 10%, at least 1% up to 5%, and at least 1% up to 3% of the saturation level during at least 25% of the saccharification period, such as at least 50% or at least 75% of the saccharification period. When the enzyme composition comprises an oxidoreductase the dissolved oxygen concentration may be higher up to 70% of the saturation level.

Oxygen is added to the vessel to achieve the desired concentration of dissolved oxygen during saccharification. Maintaining the dissolved oxygen level within a desired range can be accomplished by aeration of the vessel, tank or the like by adding compressed air through a diffuser or sparger, or by other known methods of aeration. The aeration rate can be controlled on the basis of feedback from a dissolved oxygen sensor placed in the vessel/tank, or the system can run at a constant rate without feedback control. In the case of a hydrolysis train consisting of a plurality of vessels/tanks connected in series, aeration can be implemented in one or more or all of the vessels/tanks. Oxygen aeration systems are well known in the art. According to the invention any suitable aeration system may be used. Commercial aeration systems are designed by, e.g., Chemineer, Derby, England, and build by, e.g., Paul Mueller Company, MO, USA.

The enzyme compositions can comprise any protein useful in degrading the cellulosic material.

In one aspect, the enzyme composition comprises or further comprises one or more (e.g., several) proteins selected from the group consisting of a cellulase, an AA9 polypeptide, a hemicellulase, an esterase, an expansin, a ligninolytic enzyme, an oxidoreductase, a pectinase, a protease, and a swollenin. In another aspect, the cellulase is preferably one or more (e.g., several) enzymes selected from the group consisting of an endoglucanase, a cellobiohydrolase, and a beta-glucosidase. In another aspect, the hemicellulase is preferably one or more (e.g., several) enzymes selected from the group consisting of an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. In another aspect, the oxidoreductase is preferably one or more (e.g., several) enzymes selected from the group consisting of a catalase, a laccase, and a peroxidase.

In another aspect, the enzyme composition comprises one or more (e.g., several) cellulolytic enzymes. In another aspect, the enzyme composition comprises or further comprises one or more (e.g., several) hemicellulolytic enzymes. In another aspect, the enzyme composition comprises one or more (e.g., several) cellulolytic enzymes and one or more (e.g., several) hemicellulolytic enzymes. In another aspect, the enzyme composition comprises one or more (e.g., several) enzymes selected from the group of cellulolytic enzymes and hemicellulolytic enzymes. In another aspect, the enzyme composition comprises an endoglucanase. In another aspect, the enzyme composition comprises a cellobiohydrolase. In another aspect, the enzyme composition comprises a beta-glucosidase. In another aspect, the enzyme composition comprises an AA9 polypeptide. In another aspect, the enzyme composition comprises an endoglucanase and an AA9 polypeptide. In another aspect, the enzyme composition comprises a cellobiohydrolase and an AA9 polypeptide. In another aspect, the enzyme composition comprises a beta-glucosidase and an AA9 polypeptide. In another aspect, the enzyme composition comprises an endoglucanase and a cellobiohydrolase. In another aspect, the enzyme composition comprises an endoglucanase I, an endoglucanase II, or a combination of an endoglucanase I and an endoglucanase II, and a cellobiohydrolase I, a cellobiohydrolase II, or a combination of a cellobiohydrolase I and a cellobiohydrolase II. In another aspect, the enzyme composition comprises an endoglucanase and a beta-glucosidase. In another aspect, the enzyme composition comprises an endoglucanase I, an endoglucanase II, or a combination of an endoglucanase I and an endoglucanase II, and a beta-glucosidase. In another aspect, the enzyme composition comprises a beta-glucosidase and a cellobiohydrolase. In another aspect, the enzyme composition comprises a beta-glucosidase and a cellobiohydrolase I, a cellobiohydrolase II, or a combination of a cellobiohydrolase I and a cellobiohydrolase II. In another aspect, the enzyme composition comprises an endoglucanase, an AA9 polypeptide, and a cellobiohydrolase. In another aspect, the enzyme composition comprises an endoglucanase I, an endoglucanase II, or a combination of an endoglucanase I and an endoglucanase II, an AA9 polypeptide, and a cellobiohydrolase I, a cellobiohydrolase II, or a combination of a cellobiohydrolase I and a cellobiohydrolase II. In another aspect, the enzyme composition comprises an endoglucanase, a beta-glucosidase, and an AA9 polypeptide. In another aspect, the enzyme composition comprises a beta-glucosidase, an AA9 polypeptide, and a cellobiohydrolase. In another aspect, the enzyme composition comprises a beta-glucosidase, an AA9 polypeptide, and a cellobiohydrolase I, a cellobiohydrolase II, or a combination of a cellobiohydrolase I and a cellobiohydrolase II. In another aspect, the enzyme composition comprises an endoglucanase, a beta-glucosidase, and a cellobiohydrolase. In another aspect, the enzyme composition comprises an endoglucanase I, an endoglucanase II, or a combination of an endoglucanase I and an endoglucanase II, a beta-glucosidase, and a cellobiohydrolase I, a cellobiohydrolase II, or a combination of a cellobiohydrolase I and a cellobiohydrolase II. In another aspect, the enzyme composition comprises an endoglucanase, a cellobiohydrolase, a beta-glucosidase, and an AA9 polypeptide. In another aspect, the enzyme composition comprises an endoglucanase I, an endoglucanase II, or a combination of an endoglucanase I and an endoglucanase II, a beta-glucosidase, an AA9 polypeptide, and a cellobiohydrolase I, a cellobiohydrolase II, or a combination of a cellobiohydrolase I and a cellobiohydrolase II.

In another aspect, the enzyme composition comprises an acetylmannan esterase. In another aspect, the enzyme composition comprises an acetylxylan esterase. In another aspect, the enzyme composition comprises an arabinanase (e.g., alpha-L-arabinanase). In another aspect, the enzyme composition comprises an arabinofuranosidase (e.g., alpha-L-arabinofuranosidase). In another aspect, the enzyme composition comprises a coumaric acid esterase. In another aspect, the enzyme composition comprises a feruloyl esterase. In another aspect, the enzyme composition comprises a galactosidase (e.g., alpha-galactosidase and/or beta-galactosidase). In another aspect, the enzyme composition comprises a glucuronidase (e.g., alpha-D-glucuronidase). In another aspect, the enzyme composition comprises a glucuronoyl esterase. In another aspect, the enzyme composition comprises a mannanase. In another aspect, the enzyme composition comprises a mannosidase (e.g., beta-mannosidase). In another aspect, the enzyme composition comprises a xylanase. In an embodiment, the xylanase is a Family 10 xylanase. In another embodiment, the xylanase is a Family 11 xylanase. In another aspect, the enzyme composition comprises a xylosidase (e.g., beta-xylosidase).

In another aspect, the enzyme composition comprises an esterase. In another aspect, the enzyme composition comprises an expansin. In another aspect, the enzyme composition comprises a ligninolytic enzyme. In an embodiment, the ligninolytic enzyme is a manganese peroxidase. In another embodiment, the ligninolytic enzyme is a lignin peroxidase. In another embodiment, the ligninolytic enzyme is a $H_2O_2$-producing enzyme. In another aspect, the enzyme composition comprises a pectinase. In another aspect, the enzyme composition comprises an oxidoreductase. In an embodiment, the oxidoreductase is a catalase. In another embodiment, the oxidoreductase is a laccase. In another embodiment, the oxidoreductase is a peroxidase. In another aspect, the enzyme composition comprises a protease. In another aspect, the enzyme composition comprises a swollenin.

In the processes of the present invention, the enzyme(s) can be added prior to or during saccharification, saccharification and fermentation, or fermentation.

One or more (e.g., several) components of the enzyme composition may be native proteins, recombinant proteins, or a combination of native proteins and recombinant proteins. For example, one or more (e.g., several) components may be native proteins of a cell, which is used as a host cell to express recombinantly one or more (e.g., several) other components of the enzyme composition. It is understood herein that the recombinant proteins may be heterologous (e.g., foreign) and/or native to the host cell. One or more (e.g., several) components of the enzyme composition may be produced as monocomponents, which are then combined to form the enzyme composition. The enzyme composition may be a combination of multicomponent and monocomponent protein preparations.

The enzymes used in the processes of the present invention may be in any form suitable for use, such as, for example, a fermentation broth formulation or a cell composition, a cell lysate with or without cellular debris, a semi-purified or purified enzyme preparation, or a host cell as a source of the enzymes. The enzyme composition may be a dry powder or granulate, a non-dusting granulate, a liquid, a stabilized liquid, or a stabilized protected enzyme. Liquid enzyme preparations may, for instance, be stabilized by adding stabilizers such as a sugar, a sugar alcohol or another polyol, and/or lactic acid or another organic acid according to established processes.

The optimum amounts of the enzymes and variants having cellobiohydrolase activity depend on several factors including, but not limited to, the mixture of cellulolytic enzymes and/or hemicellulolytic enzymes, the cellulosic material, the concentration of cellulosic material, the pretreatment(s) of the cellulosic material, temperature, time, pH, and inclusion of a fermenting organism (e.g., for Simultaneous Saccharification and Fermentation).

In one aspect, an effective amount of cellulolytic or hemicellulolytic enzyme to the cellulosic material is about 0.5 to about 50 mg, e.g., about 0.5 to about 40 mg, about 0.5 to about 25 mg, about 0.75 to about 20 mg, about 0.75 to about 15 mg, about 0.5 to about 10 mg, or about 2.5 to about 10 mg per g of the cellulosic material.

In another aspect, an effective amount of a variant having cellobiohydrolase activity to the cellulosic or hemicellulosic material is about 0.01 to about 50.0 mg, e.g., about 0.01 to about 40 mg, about 0.01 to about 30 mg, about 0.01 to about 20 mg, about 0.01 to about 10 mg, about 0.01 to about 5 mg, about 0.025 to about 1.5 mg, about 0.05 to about 1.25 mg, about 0.075 to about 1.25 mg, about 0.1 to about 1.25 mg, about 0.15 to about 1.25 mg, or about 0.25 to about 1.0 mg per g of the cellulosic or hemicellulosic material.

In another aspect, an effective amount of a variant having cellobiohydrolase activity to cellulolytic or hemicellulolytic enzyme is about 0.005 to about 1.0 g, e.g., about 0.01 to about 1.0 g, about 0.15 to about 0.75 g, about 0.15 to about 0.5 g, about 0.1 to about 0.5 g, about 0.1 to about 0.25 g, or about 0.05 to about 0.2 g per g of cellulolytic or hemicellulolytic enzyme.

The polypeptides having cellulolytic enzyme activity or hemicellulolytic enzyme activity as well as other proteins/polypeptides useful in the degradation of the cellulosic or hemicellulosic material, e.g., AA9 polypeptides can be derived or obtained from any suitable origin, including, archaeal, bacterial, fungal, yeast, plant, or animal origin. The term "obtained" also means herein that the enzyme may have been produced recombinantly in a host organism employing methods described herein, wherein the recombinantly produced enzyme is either native or foreign to the host organism or has a modified amino acid sequence, e.g., having one or more (e.g., several) amino acids that are deleted, inserted and/or substituted, i.e., a recombinantly produced enzyme that is a mutant and/or a fragment of a native amino acid sequence or an enzyme produced by nucleic acid shuffling processes known in the art. Encompassed within the meaning of a native enzyme are natural variants and within the meaning of a foreign enzyme are variants obtained by, e.g., site-directed mutagenesis or shuffling.

Each polypeptide may be a bacterial polypeptide. For example, each polypeptide may be a Gram-positive bacterial polypeptide having enzyme activity, or a Gram-negative bacterial polypeptide having enzyme activity.

Each polypeptide may also be a fungal polypeptide, e.g., a yeast polypeptide or a filamentous fungal polypeptide.

Chemically modified or protein engineered mutants of polypeptides may also be used.

One or more (e.g., several) components of the enzyme composition may be a recombinant component, i.e., produced by cloning of a DNA sequence encoding the single component and subsequent cell transformed with the DNA sequence and expressed in a host (see, for example, WO 91/17243 and WO 91/17244). The host can be a heterologous host (enzyme is foreign to host), but the host may under certain conditions also be a homologous host (enzyme is native to host). Monocomponent cellulolytic proteins may also be prepared by purifying such a protein from a fermentation broth.

In one aspect, the one or more (e.g., several) cellulolytic enzymes comprise a commercial cellulolytic enzyme preparation. Examples of commercial cellulolytic enzyme preparations suitable for use in the present invention include, for example, CELLIC® CTec (Novozymes A/S), CELLIC® CTec2 (Novozymes A/S), CELLIC® CTec3 (Novozymes A/S), CELLIC® CTec4 (Novozymes A/S), CELLUCLAST™ (Novozymes A/S), NOVOZYM™ 188 (Novozymes A/S), SPEZYME™ CP (Genencor Int.), ACCELLERASE™ TRIO (DuPont), FILTRASE® NL (DSM); METHAPLUS® S/L 100 (DSM), ROHAMENT™ 7069 W (Röhm GmbH), or ALTERNAFUEL® CMAX3™ (Dyadic International, Inc.). The cellulolytic enzyme preparation is added in an amount effective from about 0.001 to about 5.0 wt. % of solids, e.g., about 0.025 to about 4.0 wt. % of solids or about 0.005 to about 2.0 wt. % of solids.

Examples of bacterial endoglucanases that can be used in the processes of the present invention, include, but are not limited to, *Acidothermus cellulolyticus* endoglucanase (WO 91/05039; WO 93/15186; U.S. Pat. No. 5,275,944; WO 96/02551; U.S. Pat. No. 5,536,655; WO 00/70031; WO 05/093050), *Erwinia carotovara* endoglucanase (Saarilahti et al., 1990, *Gene* 90: 9-14), *Thermobifida fusca* endoglucanase III (WO 05/093050), and *Thermobifida fusca* endoglucanase V (WO 05/093050).

Examples of fungal endoglucanases that can be used in the present invention, include, but are not limited to, *Trichoderma reesei* endoglucanase I (Penttila et al., 1986, *Gene* 45: 253-263, *Trichoderma reesei* Cel7B endoglucanase I (GenBank:M15665), *Trichoderma reesei* endoglucanase II (Saloheimo et al., 1988, *Gene* 63:11-22), *Trichoderma reesei* Cel5A endoglucanase II (GenBank:M19373), *Trichoderma reesei* endoglucanase III (Okada et al., 1988, *Appl. Environ. Microbiol.* 64: 555-563, GenBank:AB003694), *Trichoderma reesei* endoglucanase V (Saloheimo et al., 1994, *Molecular Microbiology* 13: 219-228, GenBank:Z33381), *Aspergillus aculeatus* endoglucanase (Ooi et al., 1990, *Nucleic Acids Research* 18: 5884), *Aspergillus kawachii* endoglucanase (Sakamoto et al., 1995, *Current Genetics* 27: 435-439), *Fusarium oxysporum* endoglucanase (GenBank: L29381), *Humicola grisea* var. *thermoidea* endoglucanase (GenBank:AB003107), *Melanocarpus albomyces* endoglucanase (GenBank:MAL515703), *Neurospora crassa* endoglucanase (GenBank:XM_324477), *Humicola insolens* endoglucanase V, *Myceliophthora thermophila* CBS 117.65 endoglucanase, *Thermoascus aurantiacus* endoglucanase I (GenBank:AF487830), *Trichoderma reesei* strain No. VTT-D-80133 endoglucanase (GenBank:M15665), and *Penicillium pinophilum* endoglucanase (WO 2012/062220).

Examples of cellobiohydrolases useful in the present invention include, but are not limited to, *Aspergillus aculeatus* cellobiohydrolase II (WO 2011/059740), *Aspergillus fumigatus* cellobiohydrolase I (WO 2013/028928), *Aspergillus fumigatus* cellobiohydrolase II (WO 2013/028928), *Chaetomium thermophilum* cellobiohydrolase I, *Chaetomium thermophilum* cellobiohydrolase II, *Humicola insolens* cellobiohydrolase I, *Myceliophthora thermophila* cellobiohydrolase II (WO 2009/042871), *Penicillium occitanis* cellobiohydrolase I (GenBank:AY690482), *Talaromyces emersonii* cellobiohydrolase I (GenBank:AF439936), *Thielavia hyrcanie* cellobiohydrolase II (WO 2010/141325), *Thielavia terrestris* cellobiohydrolase II (CEL6A, WO 2006/074435), *Trichoderma reesei* cellobiohydrolase I, *Trichoderma reesei* cellobiohydrolase II, and *Trichophaea saccata* cellobiohydrolase II (WO 2010/057086).

Examples of beta-glucosidases useful in the present invention include, but are not limited to, beta-glucosidases from *Aspergillus aculeatus* (Kawaguchi et al., 1996, *Gene* 173: 287-288), *Aspergillus fumigatus* (WO 2005/047499), *Aspergillus niger* (Dan et al., 2000, *J. Biol. Chem.* 275: 4973-4980), *Aspergillus oryzae* (WO 02/095014), *Penicillium brasilianum* I BT 20888 (WO 2007/019442 and WO 2010/088387), *Thielavia terrestris* (WO 2011/035029), and *Trichophaea saccata* (WO 2007/019442).

Other useful endoglucanases, cellobiohydrolases, and beta-glucosidases are disclosed in numerous Glycosyl Hydrolase families using the classification according to Henrissat, 1991, *Biochem. J.* 280: 309-316, and Henrissat and Bairoch, 1996, *Biochem. J.* 316: 695-696.

In the processes of the present invention, any AA9 polypeptide can be used as a component of the enzyme composition.

Examples of AA9 polypeptides useful in the processes of the present invention include, but are not limited to, AA9 polypeptides from *Thielavia terrestris* (WO 2005/074647, WO 2008/148131, and WO 2011/035027), *Thermoascus aurantiacus* (WO 2005/074656 and WO 2010/065830), *Trichoderma reesei* (WO 2007/089290 and WO 2012/149344), *Myceliophthora thermophila* (WO 2009/085935, WO 2009/085859, WO 2009/085864, WO 2009/085868, and WO 2009/033071), *Aspergillus fumigatus* (WO 2010/138754), *Penicillium pinophilum* (WO 2011/005867), *Thermoascus* sp. (WO 2011/039319), *Penicillium* sp. (*emersoni*0 (WO 2011/041397 and WO 2012/000892), *Thermoascus crustaceous* (WO 2011/041504), *Aspergillus aculeatus* (WO 2012/030799), *Thermomyces lanuginosus* (WO 2012/113340, WO 2012/129699, WO 2012/130964, and WO 2012/129699), *Aurantiporus alborubescens* (WO 2012/122477), *Trichophaea saccata* (WO 2012/122477), *Penicillium thomii* (WO 2012/122477), *Talaromyces stipitatus* (WO 2012/135659), *Humicola insolens* (WO 2012/146171), *Malbranchea cinnamomea* (WO 2012/101206), *Talaromyces leycettanus* (WO 2012/101206), *Chaetomium thermophilum* (WO 2012/101206), *Talaromyces thermophilus* (WO 2012/129697 and WO 2012/130950), *Acrophialophora fusispora* (WO 2013/043910), and *Corynascus sepedonium* (WO 2013/043910).

In one aspect, the AA9 polypeptide is used in the presence of a soluble activating divalent metal cation according to WO 2008/151043 or WO 2012/122518, e.g., manganese or copper.

In another aspect, the AA9 polypeptide is used in the presence of a dioxy compound, a bicylic compound, a heterocyclic compound, a nitrogen-containing compound, a quinone compound, a sulfur-containing compound, or a liquor obtained from a pretreated cellulosic material such as pretreated corn stover (WO 2012/021394, WO 2012/021395, WO 2012/021396, WO 2012/021399, WO 2012/021400, WO 2012/021401, WO 2012/021408, and WO 2012/021410).

In one aspect, such a compound is added at a molar ratio of the compound to glucosyl units of cellulose of about $10^{-6}$ to about 10, e.g., about $10^{-6}$ to about 7.5, about $10^{-6}$ to about 5, about $10^{-6}$ to about 2.5, about $10^{-6}$ to about 1, about $10^{-5}$ to about 1, about $10^{-5}$ to about $10^{-1}$, about $10^{-4}$ to about $10^{-1}$, about $10^{-3}$ to about $10^{-1}$, or about $10^{-3}$ to about $10^{-2}$. In another aspect, an effective amount of such a compound is about 0.1 µM to about 1 M, e.g., about 0.5 µM to about 0.75 M, about 0.75 µM to about 0.5 M, about 1 µM to about 0.25 M, about 1 µM to about 0.1 M, about 5 µM to about 50 mM, about 10 µM to about 25 mM, about 50 µM to about 25 mM, about 10 µM to about 10 mM, about 5 µM to about 5 mM, or about 0.1 mM to about 1 mM.

The term "liquor" means the solution phase, either aqueous, organic, or a combination thereof, arising from treatment of a lignocellulose and/or hemicellulose material in a slurry, or monosaccharides thereof, e.g., xylose, arabinose, mannose, etc., under conditions as described in WO 2012/021401, and the soluble contents thereof. A liquor for cellulolytic enhancement of an AA9 polypeptide can be produced by treating a lignocellulose or hemicellulose material (or feedstock) by applying heat and/or pressure, optionally in the presence of a catalyst, e.g., acid, optionally in the presence of an organic solvent, and optionally in combination with physical disruption of the material, and then separating the solution from the residual solids. Such conditions determine the degree of cellulolytic enhancement obtainable through the combination of liquor and an AA9 polypeptide during hydrolysis of a cellulosic substrate by a cellulolytic enzyme preparation. The liquor can be separated from the treated material using a method standard in the art, such as filtration, sedimentation, or centrifugation.

In one aspect, an effective amount of the liquor to cellulose is about $10^{-6}$ to about 10 g per g of cellulose, e.g., about $10^{-6}$ to about 7.5 g, about $10^{-6}$ to about 5 g, about $10^{-6}$ to about 2.5 g, about $10^{-6}$ to about 1 g, about $10^{-5}$ to about 1 g, about $10^{-5}$ to about $10^{-1}$ g, about $10^{-4}$ to about $10^{-1}$ g, about $10^{-3}$ to about $10^{-1}$ g, or about $10^{-3}$ to about $10^{-2}$ g per g of cellulose.

In one aspect, the one or more (e.g., several) hemicellulolytic enzymes comprise a commercial hemicellulolytic enzyme preparation. Examples of commercial hemicellulolytic enzyme preparations suitable for use in the present invention include, for example, SHEARZYME™ (Novozymes A/S), CELLIC® HTec (Novozymes A/S), CELLIC® HTec2 (Novozymes A/S), CELLIC® HTec3 (Novozymes A/S), VISCOZYME® (Novozymes A/S), ULTRAFLO® (Novozymes A/S), PULPZYME® HC (Novozymes A/S), MULTIFECT® Xylanase (Genencor), ACCELLERASE® XY (Genencor), ACCELLERASE® XC (Genencor), ECOPULP® TX-200A (AB Enzymes), HSP 6000 Xylanase (DSM), DEPOL™ 333P (Biocatalysts Limit, Wales, UK), DEPOL™ 740L. (Biocatalysts Limit, Wales, UK), and DEPOL™ 762P (Biocatalysts Limit, Wales, UK), ALTERNA FUEL 100P (Dyadic), and ALTERNA FUEL 200P (Dyadic).

Examples of xylanases useful in the processes of the present invention include, but are not limited to, xylanases from *Aspergillus aculeatus* (GeneSeqP:AAR63790; WO 94/21785), *Aspergillus fumigatus* (WO 2006/078256), *Penicillium pinophilum* (WO 2011/041405), *Penicillium* sp. (WO 2010/126772), *Thermomyces lanuginosus* (GeneSeqP: BAA22485), *Talaromyces thermophilus* (GeneSeqP: BAA22834), *Thielavia terrestris* NRRL 8126 (WO 2009/079210), and *Trichophaea saccata* (WO 2011/057083).

Examples of beta-xylosidases useful in the processes of the present invention include, but are not limited to, beta-xylosidases from *Neurospora crassa* (SwissProt:Q7SOW4), *Trichoderma reesei* (UniProtKB/TrEMBL:Q92458), *Talaromyces emersonii* (SwissProt:Q8X212), and *Talaromyces thermophilus* (GeneSeqP:BAA22816).

Examples of acetylxylan esterases useful in the processes of the present invention include, but are not limited to, acetylxylan esterases from *Aspergillus aculeatus* (WO 2010/108918), *Chaetomium globosum* (UniProt:Q2GWX4), *Chaetomium gracile* (GeneSeqP:AAB82124), *Humicola insolens* DSM 1800 (WO 2009/073709), *Hypocrea jecorina* (WO 2005/001036), *Myceliophtera thermophila* (WO 2010/014880), *Neurospora crassa* (UniProt:q7s259), *Phaeosphaeria nodorum* (UniProt:Q0UHJ1), and *Thielavia terrestris* NRRL 8126 (WO 2009/042846).

Examples of feruloyl esterases (ferulic acid esterases) useful in the processes of the present invention include, but are not limited to, feruloyl esterases form *Humicola insolens* DSM 1800 (WO 2009/076122), *Neosartorya fischeri* (UniProt:A1D9T4), *Neurospora crassa* (UniProt:Q9HGR3), *Penicillium aurantiogriseum* (WO 2009/127729), and *Thielavia terrestris* (WO 2010/053838 and WO 2010/065448).

Examples of arabinofuranosidases useful in the processes of the present invention include, but are not limited to, arabinofuranosidases from *Aspergillus niger* (GeneSeqP: AAR94170), *Humicola insolens* DSM 1800 (WO 2006/114094 and WO 2009/073383), and *M. giganteus* (WO 2006/114094).

Examples of alpha-glucuronidases useful in the processes of the present invention include, but are not limited to, alpha-glucuronidases from *Aspergillus clavatus* (UniProt: alcc12), *Aspergillus fumigatus* (SwissProt:Q4VWV45), *Aspergillus niger* (UniProt:Q96WX9), *Aspergillus terreus* (SwissProt:Q0CJP9), *Humicola insolens* (WO 2010/014706), *Penicillium aurantiogriseum* (WO 2009/068565), *Talaromyces emersonii* (UniProt:Q8X211), and *Trichoderma reesei* (UniProt:Q99024).

Examples of oxidoreductases useful in the processes of the present invention include, but are not limited to, *Aspergillus lentilus* catalase, *Aspergillus fumigatus* catalase, *Aspergillus niger* catalase, *Aspergillus oryzae* catalase, *Humicola insolens* catalase, *Neurospora crassa* catalase, *Penicillium emersonii* catalase, *Scytalidium thermophilum* catalase, *Talaromyces stipitatus* catalase, *Thermoascus aurantiacus* catalase, *Coprinus cinereus* laccase, *Myceliophthora thermophila* laccase, *Polyporus pinsitus* laccase, *Pycnoporus cinnabarinus* laccase, *Rhizoctonia solani* laccase, *Streptomyces coelicolor* laccase, *Coprinus cinereus* peroxidase, Soy peroxidase, Royal palm peroxidase.

The polypeptides having enzyme activity used in the processes of the present invention may be produced by fermentation of the above-noted microbial strains on a nutrient medium containing suitable carbon and nitrogen sources and inorganic salts, using procedures known in the art (see, e.g., Bennett, J. W. and LaSure, L. (eds.), *More Gene Manipulations in Fungi*, Academic Press, C A, 1991). Suitable media are available from commercial suppliers or may be prepared according to published compositions (e.g., in catalogues of the American Type Culture Collection). Temperature ranges and other conditions suitable for growth and enzyme production are known in the art (see, e.g., Bailey, J. E., and Ollis, D. F., *Biochemical Engineering Fundamentals*, McGraw-Hill Book Company, N Y, 1986).

The fermentation can be any method of cultivation of a cell resulting in the expression or isolation of an enzyme or protein. Fermentation may, therefore, be understood as comprising shake flask cultivation, or small- or large-scale fermentation (including continuous, batch, fed-batch, or solid state fermentations) in laboratory or industrial fermentors performed in a suitable medium and under conditions allowing the enzyme to be expressed or isolated. The resulting enzymes produced by the methods described above may be recovered from the fermentation medium and purified by conventional procedures.

Fermentation.

The fermentable sugars obtained from the hydrolyzed cellulosic material can be fermented by one or more (e.g., several) fermenting microorganisms capable of fermenting the sugars directly or indirectly into a desired fermentation product. "Fermentation" or "fermentation process" refers to any fermentation process or any process comprising a fermentation step. Fermentation processes also include fermentation processes used in the consumable alcohol industry (e.g., beer and wine), dairy industry (e.g., fermented dairy products), leather industry, and tobacco industry. The fermentation conditions depend on the desired fermentation product and fermenting organism and can easily be determined by one skilled in the art.

In the fermentation step, sugars, released from the cellulosic material as a result of the pretreatment and enzymatic hydrolysis steps, are fermented to a product, e.g., ethanol, by a fermenting organism, such as yeast. Hydrolysis (saccharification) and fermentation can be separate or simultaneous.

Any suitable hydrolyzed cellulosic material can be used in the fermentation step in practicing the present invention. The material is generally selected based on economics, i.e., costs per equivalent sugar potential, and recalcitrance to enzymatic conversion.

The term "fermentation medium" is understood herein to refer to a medium before the fermenting microorganism(s) is(are) added, such as, a medium resulting from a saccharification process, as well as a medium used in a simultaneous saccharification and fermentation process (SSF).

"Fermenting microorganism" refers to any microorganism, including bacterial and fungal organisms, suitable for use in a desired fermentation process to produce a fermentation product. The fermenting organism can be hexose and/or pentose fermenting organisms, or a combination thereof. Both hexose and pentose fermenting organisms are well known in the art. Suitable fermenting microorganisms can ferment, i.e., convert, sugars, such as glucose, xylose, xylulose, arabinose, maltose, mannose, galactose, and/or oligosaccharides, directly or indirectly into the desired fermentation product. Examples of bacterial and fungal fermenting organisms producing ethanol are described by Lin et al., 2006, *Appl. Microbiol. Biotechnol.* 69: 627-642.

Examples of fermenting microorganisms that can ferment hexose sugars include bacterial and fungal organisms, such as yeast. Yeast include strains of *Candida*, Kluyveromyces, and *Saccharomyces*, e.g., *Candida sonorensis*, *Kluyveromyces marxianus*, and *Saccharomyces cerevisiae*.

Examples of fermenting organisms that can ferment pentose sugars in their native state include bacterial and fungal organisms, such as some yeast. Xylose fermenting yeast include strains of *Candida*, preferably *C. sheatae* or *C. sonorensis*; and strains of *Pichia*, e.g., *P. stipitis*, such as *P. stipitis* CBS 5773. Pentose fermenting yeast include strains of *Pachysolen*, preferably *P. tannophilus*. Organisms not capable of fermenting pentose sugars, such as xylose and arabinose, may be genetically modified to do so by methods known in the art.

Examples of bacteria that can efficiently ferment hexose and pentose to ethanol include, for example, *Bacillus coagulans, Clostridium acetobutylicum, Clostridium thermocellum, Clostridium phytofermentans, Geobacillus* sp., *Thermoanaerobacter saccharolyticum*, and *Zymomonas mobilis* (Philippidis, G. P., 1996, Cellulose bioconversion technology, in *Handbook on Bioethanol: Production and Utilization*, Wyman, C. E., ed., Taylor & Francis, Washington, DC, 179-212).

Other fermenting organisms include strains of *Bacillus*, such as *Bacillus coagulans; Candida*, such as *C. sonorensis, C. methanosorbosa, C. diddensiae, C. parapsilosis, C. naedodendra, C. blankii, C. entomophilia, C. brassicae, C. pseudotropicalis, C. boidinii, C. utilis*, and *C. scehatae; Clostridium*, such as *C. acetobutylicum, C. thermocellum*, and *C. phytofermentans; E. coli*, especially *E. coli* strains that have been genetically modified to improve the yield of ethanol; *Geobacillus* sp.; *Hansenula*, such as *Hansenula anomala*; *Klebsiella*, such as *K. oxytoca*; *Kluyveromyces*, such as *K. marxianus, K. lactis, K. thermotolerans*, and *K. fragilis*; *Schizosaccharomyces*, such as *S. pombe*; *Thermoanaerobacter*, such as *Thermoanaerobacter saccharolyticum*; and *Zymomonas*, such as *Zymomonas mobilis*.

Commercially available yeast suitable for ethanol production include, e.g., BIO-FERM® AFT and XR (Lallemand Specialities, Inc., USA), ETHANOL REDO yeast (Lesaffre et Compagnie, France), FALI® (AB Mauri Food Inc., USA), FERMIOLO (Rymco International AG, Denmark), GERT STRAND™ (Gert Strand AB, Sweden), and SUPERSTART™ and THERMOSACC® fresh yeast (Lallemand Specialities, Inc., USA).

In an aspect, the fermenting microorganism has been genetically modified to provide the ability to ferment pentose sugars, such as xylose utilizing, arabinose utilizing, and xylose and arabinose co-utilizing microorganisms.

The cloning of heterologous genes into various fermenting microorganisms has led to the construction of organisms capable of converting hexoses and pentoses to ethanol (co-fermentation) (Chen and Ho, 1993, *Appl. Biochem. Biotechnol.* 39-40: 135-147; Ho et al., 1998, *Appl. Environ. Microbiol.* 64: 1852-1859; Kotter and Ciriacy, 1993, *Appl. Microbiol. Biotechnol.* 38: 776-783; Walfridsson et al., 1995, *Appl. Environ. Microbiol.* 61: 4184-4190; Kuyper et al., 2004, *FEMS Yeast Research* 4: 655-664; Beall et al., 1991, *Biotech. Bioeng.* 38: 296-303; Ingram et al., 1998, *Biotechnol. Bioeng.* 58: 204-214; Zhang et al., 1995, *Science* 267: 240-243; Deanda et al., 1996, *Appl. Environ. Microbiol.* 62: 4465-4470; WO 03/062430).

In one aspect, the fermenting organism comprises a polynucleotide encoding a polypeptide having cellobiohydrolase activity of the present invention.

In another aspect, the fermenting organism comprises one or more polynucleotides encoding one or more cellulolytic enzymes, hemicellulolytic enzymes, and accessory enzymes described herein.

It is well known in the art that the organisms described above can also be used to produce other substances, as described herein.

The fermenting microorganism is typically added to the degraded cellulosic material or hydrolysate and the fermentation is performed for about 8 to about 96 hours, e.g., about 24 to about 60 hours. The temperature is typically between about 26° C. to about 60° C., e.g., about 32° C. or 50° C., and about pH 3 to about pH 8, e.g., pH 4-5, 6, or 7.

In one aspect, the yeast and/or another microorganism are applied to the degraded cellulosic material and the fermentation is performed for about 12 to about 96 hours, such as typically 24-60 hours. In another aspect, the temperature is preferably between about 20° C. to about 60° C., e.g., about 25° C. to about 50° C., about 32° C. to about 50° C., or about 32° C. to about 50° C., and the pH is generally from about pH 3 to about pH 7, e.g., about pH 4 to about pH 7. However, some fermenting organisms, e.g., bacteria, have higher fermentation temperature optima. Yeast or another microorganism is preferably applied in amounts of approximately $10^5$ to $10^{12}$, preferably from approximately $10^7$ to $10^{10}$, especially approximately $2\times10^8$ viable cell count per ml of fermentation broth. Further guidance in respect of using yeast for fermentation can be found in, e.g., "The Alcohol Textbook" (Editors K. Jacques, T. P. Lyons and D. R. Kelsall, Nottingham University Press, United Kingdom 1999), which is hereby incorporated by reference.

A fermentation stimulator can be used in combination with any of the processes described herein to further improve the fermentation process, and, in particular, the performance of the fermenting microorganism, such as, rate enhancement and ethanol yield. A "fermentation stimulator" refers to stimulators for growth of the fermenting microorganisms, in particular, yeast. Preferred fermentation stimulators for growth include vitamins and minerals. Examples of vitamins include multivitamins, biotin, pantothenate, nicotinic acid, meso-inositol, thiamine, pyridoxine, para-aminobenzoic acid, folic acid, riboflavin, and Vitamins A, B, C, D, and E. See, for example, Alfenore et al., Improving ethanol production and viability of *Saccharomyces cerevisiae* by a vitamin feeding strategy during fed-batch process, Springer-Verlag (2002), which is hereby incorporated by reference. Examples of minerals include minerals and mineral salts that can supply nutrients comprising P, K, Mg, S, Ca, Fe, Zn, Mn, and Cu.

Fermentation Products:

A fermentation product can be any substance derived from the fermentation. The fermentation product can be, without limitation, an alcohol (e.g., arabinitol, n-butanol, isobutanol, ethanol, glycerol, methanol, ethylene glycol, 1,3-propanediol [propylene glycol], butanediol, glycerin, sorbitol, and xylitol); an alkane (e.g., pentane, hexane, heptane, octane, nonane, decane, undecane, and dodecane), a cycloalkane (e.g., cyclopentane, cyclohexane, cycloheptane, and cyclooctane), an alkene (e.g., pentene, hexene, heptene, and octene); an amino acid (e.g., aspartic acid, glutamic acid, glycine, lysine, serine, and threonine); a gas (e.g., methane, hydrogen ($H_2$), carbon dioxide ($CO_2$), and carbon monoxide (CO)); isoprene; a ketone (e.g., acetone); an organic acid (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, oxaloacetic acid, propionic acid, succinic acid, and xylonic acid); and polyketide.

In one aspect, the fermentation product is an alcohol. The term "alcohol" encompasses a substance that contains one or more hydroxyl moieties. The alcohol can be, but is not limited to, n-butanol, isobutanol, ethanol, methanol, arabinitol, butanediol, ethylene glycol, glycerin, glycerol, 1,3-propanediol, sorbitol, xylitol. See, for example, Gong et al., 1999, Ethanol production from renewable resources, in *Advances in Biochemical Engineering/Biotechnology*, Scheper, T., ed., Springer-Verlag Berlin Heidelberg, Germany, 65: 207-241; Silveira and Jonas, 2002, *Appl. Microbiol. Biotechnol.* 59: 400-408; Nigam and Singh, 1995, *Process Biochemistry* 30(2): 117-124; Ezeji et al., 2003, *World Journal of Microbiology and Biotechnology* 19(6): 595-603.

In another aspect, the fermentation product is an alkane. The alkane may be an unbranched or a branched alkane. The alkane can be, but is not limited to, pentane, hexane, heptane, octane, nonane, decane, undecane, or dodecane.

In another aspect, the fermentation product is a cycloalkane. The cycloalkane can be, but is not limited to, cyclopentane, cyclohexane, cycloheptane, or cyclooctane.

In another aspect, the fermentation product is an alkene. The alkene may be an unbranched or a branched alkene. The alkene can be, but is not limited to, pentene, hexene, heptene, or octene.

In another aspect, the fermentation product is an amino acid. The organic acid can be, but is not limited to, aspartic acid, glutamic acid, glycine, lysine, serine, or threonine. See, for example, Richard and Margaritis, 2004, *Biotechnology and Bioengineering* 87(4): 501-515.

In another aspect, the fermentation product is a gas. The gas can be, but is not limited to, methane, $H_2$, $CO_2$, or CO. See, for example, Kataoka et al., 1997, *Water Science and Technology* 36(6-7): 41-47; and Gunaseelan, 1997, *Biomass and Bioenergy* 13(1-2): 83-114.

In another aspect, the fermentation product is isoprene.

In another aspect, the fermentation product is a ketone. The term "ketone" encompasses a substance that contains one or more ketone moieties. The ketone can be, but is not limited to, acetone.

In another aspect, the fermentation product is an organic acid. The organic acid can be, but is not limited to, acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, propionic acid, succinic acid, or xylonic acid. See, for example, Chen and Lee, 1997, *Appl. Biochem. Biotechnol.* 63-65: 435-448.

In another aspect, the fermentation product is polyketide.

Recovery.

The fermentation product(s) can be optionally recovered from the fermentation medium using any method known in the art including, but not limited to, chromatography, electrophoretic procedures, differential solubility, distillation, or extraction. For example, alcohol is separated from the fermented cellulosic material and purified by conventional methods of distillation. Ethanol with a purity of up to about 96 vol. % can be obtained, which can be used as, for example, fuel ethanol, drinking ethanol, i.e., potable neutral spirits, or industrial ethanol.

Plants

The present invention also relates to isolated plants, e.g., a transgenic plant, plant part, or plant cell, comprising a polynucleotide of the present invention to express and produce the variant in recoverable quantities. The variant may be recovered from the plant or plant part. Alternatively, the plant or plant part containing the variant may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, Poa), forage grass such as *Festuca*, *Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilization of the invention are also considered plant parts, e.g., embryos, endosperms, aleurone and seed coats.

Also, included within the scope of the present invention are the progeny of such plants, plant parts, and plant cells.

The transgenic plant or plant cell expressing a variant may be constructed in accordance with methods known in the art. In short, the plant or plant cell is constructed by incorporating one or more expression constructs encoding a variant into the plant host genome or chloroplast genome and propagating the resulting modified plant or plant cell into a transgenic plant or plant cell.

The expression construct is conveniently a nucleic acid construct that comprises a polynucleotide encoding a variant operably linked with appropriate regulatory sequences required for expression of the polynucleotide in the plant or plant part of choice. Furthermore, the expression construct may comprise a selectable marker useful for identifying plant cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, based on when, where, and how the variant is desired to be expressed (Sticklen, 2008, *Nature Reviews* 9: 433-443). For instance, the expression of the gene encoding a variant may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, or the rice actin 1 promoter may be used (Franck et al., 1980, *Cell* 21: 285-294; Christensen et al., 1992, *Plant Mol. Biol.* 18: 675-689; Zhang et al., 1991, *Plant Cell* 3: 1155-1165). Organ-specific promoters may be, for example, a promoter from storage sink tissues such as seeds, roots, potato tubers, and fruits (Edwards and Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant Cell Physiol.* 39: 885-889), a *Vicia faba* promoter from the legumin B4 and the unknown seed protein gene from *Vicia faba* (Conrad et al., 1998, *J. Plant Physiol.* 152: 708-711), a promoter from a seed oil body protein (Chen et al., 1998, *Plant Cell Physiol.* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiol.* 102: 991-1000), the *chlorella* virus adenine methyltransferase gene promoter (Mitra and Higgins, 1994, *Plant Mol. Biol.* 26: 85-93), the aldP gene promoter from rice (Kagaya et al., 1995, *Mol. Gen. Genet.* 248: 668-674), or a wound inducible promoter such as the potato pin2 promoter (Xu et al., 1993, *Plant Mol. Biol.* 22: 573-588). Likewise, the promoter may be induced by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a variant in the plant. For instance, the promoter enhancer element may be an intron that is placed between the promoter and the polynucleotide encoding a variant. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

*Agrobacterium tumefaciens*-mediated gene transfer is a method for generating transgenic dicots (for a review, see Hooykas and Schilperoort, 1992, *Plant Mol. Biol.* 19: 15-38) and for transforming monocots, although other transformation methods may be used for these plants. A method for generating transgenic monocots is particle bombardment (microscopic gold or tungsten particles coated with the transforming DNA) of embryonic calli or developing embryos (Christou, 1992, *Plant J.* 2: 275-281; Shimamoto, 1994, *Curr. Opin. Biotechnol.* 5: 158-162; Vasil et al., 1992, *Bio/Technology* 10: 667-674). An alternative method for transformation of monocots is based on protoplast transformation as described by Omirulleh et al., 1993, *Plant Mol. Biol.* 21: 415-428. Additional transformation methods include those described in U.S. Pat. Nos. 6,395,966 and 7,151,204 (both of which are herein incorporated by reference in their entirety).

Following transformation, the transformants having incorporated the expression construct are selected and regenerated into whole plants according to methods well known in the art. Often the transformation procedure is designed for the selective elimination of selection genes either during regeneration or in the following generations by using, for example, co-transformation with two separate T-DNA constructs or site specific excision of the selection gene by a specific recombinase.

In addition to direct transformation of a particular plant genotype with a construct of the present invention, transgenic plants may be made by crossing a plant having the construct to a second plant lacking the construct. For example, a construct encoding a variant can be introduced into a particular plant variety by crossing, without the need for ever directly transforming a plant of that given variety. Therefore, the present invention encompasses not only a plant directly regenerated from cells which have been transformed in accordance with the present invention, but also the progeny of such plants. As used herein, progeny may refer to the offspring of any generation of a parent plant prepared in accordance with the present invention. Such progeny may include a DNA construct prepared in accordance with the present invention. Crossing results in the introduction of a transgene into a plant line by cross pollinating a starting line with a donor plant line. Non-limiting examples of such steps are described in U.S. Pat. No. 7,151,204.

Plants may be generated through a process of backcross conversion. For example, plants include plants referred to as a backcross converted genotype, line, inbred, or hybrid.

Genetic markers may be used to assist in the introgression of one or more transgenes of the invention from one genetic background into another. Marker assisted selection offers advantages relative to conventional breeding in that it can be used to avoid errors caused by phenotypic variations. Further, genetic markers may provide data regarding the relative degree of elite germplasm in the individual progeny of a particular cross. For example, when a plant with a desired trait which otherwise has a non-agronomically desirable genetic background is crossed to an elite parent, genetic markers may be used to select progeny which not only possess the trait of interest, but also have a relatively large proportion of the desired germplasm. In this way, the number of generations required to introgress one or more traits into a particular genetic background is minimized.

The present invention also relates to methods of producing a variant of the present invention comprising: (a) cultivating a transgenic plant, plant part, or a plant cell comprising a polynucleotide encoding the variant under conditions conducive for production of the variant; and optionally (b) recovering the variant.

The present invention is further described by the following examples that should not be construed as limiting the scope of the invention.

EXAMPLES

Media and Solutions

DOB+CSM-Leu plates were composed of 3.4 g of yeast nitrogen base without amino acids and ammonium sulfate, 0.68 g of CSM-Leu, 1 ml of 100 mM $CuSO_4.5H_2O$, 20 ml of 0.5 M K$_2$HPO$_4$, 20 g of Bacto agar, and 950 ml of deionized water. Forty ml of a 50% glucose solution were added after the autoclaved medium was tempered to 55° C.

M400 medium was composed per liter of 50 g of maltodextrin, 2 g of MgSO$_4$.7H$_2$O, 2 g of KH$_2$PO$_4$, 4 g of citric acid, 8 g of yeast extract, 2 g of urea, 0.5 g of CaCl$_2$, and 0.5 ml of AMG trace metals solution. AMG trace metals solution was composed per liter of 14.3 g of ZnSO$_4$.7H$_2$O, 2.5 g of CuSO$_4$.5H$_2$O, 0.5 g of NiCl$_2$.6H$_2$O, 13.8 g of FeSO$_4$.7H$_2$O, 8.5 g of MnSO$_4$. H$_2$O, 3 g of citric acid, and deionized water to 1 liter.

YPD medium was composed of 10 g of yeast extract, 20 g of Bacto peptone, 40 ml of 50% glucose, and deionized water to 1 liter.

TABLE 1

Primers used in the Examples below.

| Identifier | Sequence (5'-3') | Mutation |
| --- | --- | --- |
| 1214925 | TTGCAGCCAAGATCTCTGCACAGCAGGTCGGCACTT TGAC (SEQ ID NO: 7) | |
| 1214926 | TAAATCATATTAATTAAGCTCTACAGGCACTGGGAGT AAT (SEQ ID NO: 8) | |
| PvCBH1_27P_Fwd | ATCTCTGCACAGCAGGTCGGCACTTTGACGCCCGAG ACCCATCCATCG (SEQ ID NO: 9) | T8P |
| PvCBH1_27P_Rev | CGTCAAAGTGCCGACCTGCTGTGCAGAGAT (SEQ ID NO: 10) | T8P |
| PvCBHI_27A_Fwd | ATCTCTGCACAGCAGGTCGGCACTTTGACGGCCGAG ACCCATCCATCG (SEQ ID NO: 11) | T8A |
| PvCBHI_27A_Rev | CGTCAAAGTGCCGACCTGCTGTGCAGAGAT (SEQ ID NO: 12) | T8A |
| PvCBHI_36Q_Fwd | ACGACTGAGACCCATCCATCGTTGACCTGGCAGCAG TGTACCGCCGGC (SEQ ID NO: 13) | S17Q |
| PvCBHI_36Q_Rev | CCAGGTCAACGATGGATGGGTCTCAGTCGT (SEQ ID NO: 14) | S17Q |
| PvCBHI_132D_Fwd | AACATCGGTTCCCGTCTGTACTTGCTGGAGGACGAC ACCACCTACCAG (SEQ ID NO: 15) | N113D |
| PvCBHI_132D_Rev | CTCCAGCAAGTACAGACGGGAACCGATGTT (SEQ ID NO: 16) | N113D |
| PvCBHI_176R_Fwd | GTGGACATGGACGCAGATGGTGGCATGGCCCGCTA CTCCACCAACAAG (SEQ ID NO: 17) | K157R |
| PvCBHI_176R_Rev | GGCCATGCCACCATCTGCGTCCATGTCCAC (SEQ ID NO: 18) | K157R |
| PvCBHI_178P_Fwd | ATGGACGCAGATGGTGGCATGGCCAAATACCCCACC AACAAGGCCGGA (SEQ ID NO: 19) | S159P |
| PvCBHI_178P_Rev | GTATTTGGCCATGCCACCATCTGCGTCCAT (SEQ ID NO: 20) | S159P |
| PvCBHI_203N_Fwd | AGTCAATGCCCGCGGGATCTCAAGTTCATCAACGGC CAGGCCAACGTG (SEQ ID NO: 21) | D184N |
| PvCBHI_203N_Rev | GATGAACTTGAGATCCCGCGGGCATTGACT (SEQ ID NO: 22) | D184N |
| PvCBH1_218P_Fwd | GTGGAAGGCTGGACCCCCTCCACCAATGATCCCAAC TCCGGCATTGGC (SEQ ID NO: 23) | V199P |
| PvCBH1_218P_Rev | ATCATTGGTGGAGGGGGTCCAGCCTTCCAC (SEQ ID NO: 24) | V199P |
| PvCBHI_259G_Fwd | TGCGACACCCCCTCGCAAACCATGTGCACTGGCGAT GCCTGCGGTGGA (SEQ ID NO: 25) | E240G |
| PvCBHI_259G_Rev | AGTGCACATGGTTTGCGAGGGGGTGTCGCA (SEQ ID NO: 26) | E240G |
| PvCBHI_269D_Fwd | GAAGATGCCTGCGGTGGAACCTACAGCACTGACCG CTATGCCGGTACT (SEQ ID NO: 27) | S250D |
| PvCBHI_269D_Rev | AGTGCTGTAGGTTCCACCGCAGGCATCTTC (SEQ ID NO: 28) | S250D |

TABLE 1-continued

Primers used in the Examples below.

| Identifier | Sequence (5'-3') | Mutation |
|---|---|---|
| PvCBHI_293Y_Fwd | AACCCCTACCGTATGGGCGACACTTCTTTCTACGGT CCTGGCTTGACC (SEQ ID NO: 29) | F274Y |
| PvCBHI_293Y_Rev | GAAAGAAGTGTCGCCCATACGGTAGGGGTT (SEQ ID NO: 30) | F274Y |
| PvCBHI_337A_Fwd | CGCTTCTACGTCCAGAACGGCAAGGTCATCGCCCAG CCCCAGTCTACC (SEQ ID NO: 31) | G318A |
| PvCBHI_337A_Rev | GATGACCTTGCCGTTCTGGACGTAGAAGCG (SEQ ID NO: 32) | G318A |
| PvCBHI_337P_Fwd | CGCTTCTACGTCCAGAACGGCAAGGTCATCCCCCAG CCCCAGTCTACC (SEQ ID NO: 33) | G318A |
| PvCBHI_337P_Rev | GATGACCTTGCCGTTCTGGACGTAGAAGCG (SEQ ID NO: 34) | G318A |
| PvCBHI_337S_Fwd | CGCTTCTACGTCCAGAACGGCAAGGTCATCAGCCAG CCCCAGTCTACC (SEQ ID NO: 35) | G318A |
| PvCBHI_337S_Rev | GATGACCTTGCCGTTCTGGACGTAGAAGCG (SEQ ID NO: 36) | G318A |
| PvCBH1_344P_Fwd | AAGGTCATCGGTCAGCCCCAGTCTACCATCCCCGGC GTCACCGGTAAC (SEQ ID NO: 37) | T325P |
| PvCBH1_344P_Rev | GATGGTAGACTGGGGCTGACCGATGACCTT (SEQ ID NO: 38) | T325P |
| PvCBH1_347P_Fwd | GGTCAGCCCCAGTCTACCATCACTGGCGTCCCCGGT AACTCGATCACC (SEQ ID NO: 39) | T328P |
| PvCBH1_347P_Rev | GACGCCAGTGATGGTAGACTGGGGCTGACC (SEQ ID NO: 40) | T328P |
| PvCBH1_366P_Fwd | TGCAATGCGCAAAAGACCGCATTCGGCGACCCCAAT GACTTCACCAAG (SEQ ID NO: 41) | T347P |
| PvCBH1_366P_Rev | GTCGCCGAATGCGGTCTTTTGCGCATTGCA (SEQ ID NO: 42) | T347P |
| PvCBHI_368V_Fwd | GCGCAAAAGACCGCATTCGGCGACACCAATGTCTTC ACCAAGCACGGT (SEQ ID NO: 43) | D349V |
| PvCBHI_368V_Rev | ATTGGTGTCGCCGAATGCGGTCTTTTGCGC (SEQ ID NO: 44) | D349V |
| PvCBHI_377A_Fwd | AATGACTTCACCAAGCACGGTGGCATGGCAGCCATG GGTGCCGGTCTC (SEQ ID NO: 45) | G358A |
| PvCBHI_377A_Rev | TGCCATGCCACCGTGCTTGGTGAAGTCATT (SEQ ID NO: 46) | G358A |
| PvCBHI_379T_Fwd | TTCACCAAGCACGGTGGCATGGCAGGCATGACCGC CGGTCTCGCTGAT (SEQ ID NO: 47) | G360T |
| PvCBHI_379T_Rev | CATGCCTGCCATGCCACCGTGCTTGGTGAA (SEQ ID NO: 48) | G360T |
| PvCBHI_379S_Fwd | TTCACCAAGCACGGTGGCATGGCAGGCATGAGCGC CGGTCTCGCTGAT (SEQ ID NO: 49) | G360S |
| PvCBHI_379S_Rev | CATGCCTGCCATGCCACCGTGCTTGGTGAA (SEQ ID NO: 50) | G360S |
| PvCBHI_399N_Fwd | GTCATGAGTCTCTGGGATGACCATGCGGCCAACATG CTCTGGCTCGAC (SEQ ID NO: 51) | D380N |
| PvCBHI_399N_Rev | GGCCGCATGGTCATCCCAGAGACTCATGAC (SEQ ID NO: 52) | D380N |
| PvCBHI_412-3DP_Fwd | TGGCTCGACAGCACCTACCCTACCAACGCC~GACCC GACCACTCCCGGTGTC (SEQ ID NO: 53) | S393D + S394P |

TABLE 1-continued

Primers used in the Examples below.

| Identifier | Sequence (5'-3') | Mutation |
|---|---|---|
| PvCBHI_412-3DP_Rev | GGCGTTGGTAGGGTAGGTGCTGTCGAGCCA (SEQ ID NO: 54) | S393D + S394P |
| PvCBHI_410-2-3DDP_Fwd | ATGCTCTGGCTCGACAGCACCTACCCTACCGACGCC GACCCGACCACTCCCGGTGTC (SEQ ID NO: 55) | N391D + S393D + S394P |
| PvCBHI_410-2-3DDP_Rev | GGTAGGGTAGGTGCTGTCGAGCCAGAGCAT (SEQ ID NO: 56) | N391D + S393D + S394P |
| PvCBHI_412D_Fwd | TGGCTCGACAGCACCTACCCTACCAACGCCGACTCG ACCACTCCCGGT (SEQ ID NO: 57) | S393D |
| PvCBHI_412D_Rev | GGCGTTGGTAGGGTAGGTGCTGTCGAGCCA (SEQ ID NO: 58) | S393D |
| PvCBHI_413P_Fwd | CTCGACAGCACCTACCCTACCAACGCCTCCCCCACC ACTCCCGGTGTC (SEQ ID NO: 59) | S394P |
| PvCBHI_413P_Rev | GGAGGCGTTGGTAGGGTAGGTGCTGTCGAG (SEQ ID NO: 60) | S394P |
| PvCBHI_431A_Fwd | GGTACTTGCGATATCTCCTCTGGCGACCCAGCCACC GTCGAGTCTACC (SEQ ID NO: 61) | T412A |
| PvCBHI_431A_Rev | TGGGTCGCCAGAGGAGATATCGCAAGTACC (SEQ ID NO: 62) | T412A |
| PvCBHI_449V_Fwd | AACGCCTACGTCATCTACTCGAACATCAAGGTCGGT CCTCTCAACTCG (SEQ ID NO: 63) | T430V |
| PvCBHI_449V_Rev | CTTGATGTTCGAGTAGATGACGTAGGCGTT (SEQ ID NO: 64) | T430V |
| 1209353 | GCTATTTTCTAACAAAGCATCTTAGATTA (SEQ ID NO: 65) | T8P |
| 1209355 | GCTGATCCCCTCGTTTTCGGAAACGCTTTG (SEQ ID NO: 66) | T8P |

Example 1: Construction of Yeast Expression Plasmid pLSBF124

The coding sequence of the *Penicillium vasconiae* NN053742 GH7 cellobiohydrolase I (SEQ ID NO: 75) was amplified from genomic DNA using the primers shown below.

Forward primer:
(SEQ ID NO: 77)
5'-ACACAACTGGGGATCCaccatgaagggatcaatctoctatcaaatct
ac-3'

Reverse primer:
(SEQ ID NO: 78)
5'-CCCTCTAGATCTCGAGcaccacttttctcccaaatttgaag-3'

Lowercase characters of the forward primer represent a region of the coding sequence and lowercase characters of the reverse primer represent the flanking region of the coding sequence, while bold characters represent a region homologous to insertion sites of pCaHj505 (WO 2013/029496). The underlined characters in the forward primer represent 5'UTR that is not a part of the pCaHj505 vector.

The PCR was composed of 10 μmol each of the forward and reverse primers, 2 μl of *Penicillium vasconiae* genomic DNA, 10 μl of 5× PHUSION® HF Buffer (Finnzymes Oy), 1.5 μl of DMSO, 1.5 μl of 2.5 mM each of dATP, dTTP, dGTP, and dCTP, and 0.6 unit of PHUSION® High-Fidelity DNA Polymerase (Finnzymes Oy) in a final volume of 50 μl. The PCR was performed in a thermocycler programmed for denaturing at 94° C. for 3 minutes; 10 cycles of denaturing each at 94° C. for 40 seconds, annealing at 69° C. for 30 seconds, with a 1° C. decrease per cycle and elongation at 72° C. for 2 minutes; 25 cycles each at 94° C. for 40 seconds, 59° C. for 40 seconds, and 72° C. for 2 minutes; and a final extension at 72° C. for 7 minutes. The heat block then went to a 15° C. soak cycle.

A 1.8 kb PCR product was isolated by 1.0% agarose gel electrophoresis using 90 mM Tris-borate and 1 mM EDTA (TBE) buffer and then purified using an ILLUSTRA™ GFX™ PCR DNA and Gel Band Purification Kit (GE Healthcare).

Plasmid pCaHj505 was digested with BamH I and Xho I, isolated by 1.0% agarose gel electrophoresis using TBE buffer, and purified using an ILLUSTRA™ GFX™ PCR DNA and Gel Band Purification Kit.

The purified PCR fragment and the digested vector were ligated together using an IN-FUSION® HD Cloning Kit (Clontech Laboratories, Inc.) resulting in plasmid p505-GH7_Peva1, in which transcription of the *P. vasconiae* GH7 cellobiohydrolase I coding sequence was under control of an *Aspergillus oryzae* alpha-amylase gene promoter. The ligation reaction was transformed into *E. coli* TOP10 competent cells (TIANGEN Biotech Co. Ltd.) and positive transformants were detected by colony PCR by transferring a single colony to a premixed PCR solution including buffer, dNTPs, Taq DNA polymerase and primer pairs from which the PCR fragment was generated. After PCR, the reactions were analyzed by 1.0% agarose gel electrophoresis using TBE buffer. Plasmid DNA was prepared using a QIAPREP® Spin Miniprep Kit (QIAGEN GmbH) from one of the colonies showing an insert with the expected size. The plasmid was designated p505-GH7_Peva1.

Plasmid pLSBF124 was constructed for expression of the *P. vasconiae* cellobiohydrolase I (SEQ ID NO: 1) and generation of mutant gene libraries. The *P. vasconiae* cellobiohydrolase I coding sequence cDNA (nucleotides 76-1650 of SEQ ID NO: 75) was amplified from source plasmid p505-GH7-Peva1 using the primers shown in Table 1. Bold letters represent coding sequence. The remaining sequences are homologous to insertion sites of plasmid pLSBF101. Plasmid pLSBF101 was made by modifying plasmid pDB4081 (described in WO 2014/072481) to remove the sequence between the promoter and terminator and insert a *Saccharomyces cerevisiae* invertase leader sequence shown below followed by a Hind III restriction site. pLSBF101 was digested with Hind III to linearize the plasmid.

(SEQ ID NO: 79)
ATGCTTTTGCAAGCCTTCCTTTTCCTTTTGGCTGGTTTTGCAGCCAAGAT

CTCTGCA

The homologous ends of the PCR product and the digested pLSBF101 were joined together using an IN-FUSION™ Advantage PCR Cloning Kit (Clontech Laboratories, Inc.) and transformed into STELLAR™ competent *E. coli* cells (Clontech Laboratories, Inc.). Plasmid DNA was purified from transformed colonies using a QIAPREP® Spin Miniprep Kit (QIAGEN Inc.). DNA sequencing with a 3130XL Genetic Analyzer (Applied Biosystems, Inc.) confirmed the presence of the cellobiohydrolase I fragment in a final plasmid designated pLSBF124.

Example 2: Construction of *Penicillium vasconiae* Cellobiohydrolase I Variants

*Penicillium vasconiae* cellobiohydrolase I variants were constructed using a targeted mutagenesis approach. Mutagenic forward primers and complementary reverse primers were synthesized for each of the mutations of interest. Multiple PCR products were used in a yeast-assembly method to construct each mutant. Using pLSBF124 as a DNA template, mutations were introduced through PCR using the forward mutagenic primer for each mutation and a reverse primer downstream of the terminator (SEQ ID NO: 66—Primer 1209355). This reaction results in a PCR product containing a 3" fragment of the *P. vasconiae* cellobiohydrolase I gene containing the mutation of interest, a *Saccharomyces cerevisiae* alcohol dehydrogenase (ADH1) terminator, and a small amount of DNA necessary for yeast assembly during the transformation. A second PCR was performed using pLSBF124 as a DNA template with the non-mutagenic complementary reverse primer for each mutation and a forward primer upstream of the selectable marker (SEQ ID NO: 65—Primer 1209353). This reaction results in a PCR product containing a small amount of DNA necessary for yeast assembly during the transformation, a *Saccharomyces cerevisiae* 3-isopropylmalate dehydrogenase (LEU2) selectable marker gene, a *Saccharomyces cerevisiae* protease B (PRB1) promoter, a *Saccharomyces cerevisiae* invertase leader sequence, and a 5' fragment of the *P. vasconiae* cellobiohydrolase I gene. The two PCR fragments assemble when co-transformed alongside linearized pDB4164 to form a complete 2 micron expression plasmid containing the *P. vasconiae* cellobiohydrolase I gene mutant. Plasmid pDB4164 was constructed by modifying plasmid pDB3936 (WO 2010/092135). It has two additional bases (GC) next to the BamH I site to create a Not I restriction site GCGGCCGC (additional bases in bold) and contains a 1368 bp sequence between the Acc 65I and BamH I sites containing an apramycin resistance selectable marker.

A similar method was used to construct multi-mutation variants. Lysed yeast cells harboring a mutant of interest were used as template for a second round of mutagenic PCR. Different templates were used for the 3' end and 5' end PCRs. This way the 3' end PCR contains the mutation present in the template strain as well as a new mutation introduced with the mutagenic forward primer. The 5' end PCR contains the mutation present in the template strain. Using this method, variants containing multiple mutations can be constructed with two PCRs.

Example 3: Transformation and Expression of Variants in Yeast Host Strain

Plasmid pDB4164 DNA was prepared for transformation into *Saccharomyces cerevisiae* as described in WO 2015/036579, Method 4, except that a 9723 bp Acc 65I-BamH I fragment from pDB4164 was used as the gapped vector fragment instead of the 9721 bp fragment from pDB3936, which has two additional bases GC next to the BamH I site to create a Not I restriction site GCGGCCGC (additional bases in bold). Plasmid pDB4164 also differs from pDB3936 in containing a 1368 bp sequence between the Acc 65I and BamH I sites containing an apramycin resistance selectable marker which was excised by the Acc 65I and BamH I digestion and was not used in the gap-repair transformation. Digested pDB4164 was co-transformed with PCR products encoding either wild-type or mutated *Penicillium vasconiae* cellobiohydrolase I. A *Saccharomyces cerevisiae* strain (as described in WO 2014/072481) was used as an expression host for the *Penicillium vasconiae* cellobiohydrolase I variants. This strain was constructed from DYB7 (Payne et al., 2008, *Applied and Environmental Microbiology* 74(24): 7759-7766) with four copies of a protein disulfide isomerase integrated into the genome.

Transformed cells were plated to a selective medium (DOB+CSM-Leu plates) and allowed to grow at 30° C. for several days. Following the outgrowth, transformed cells were used to inoculate 96-well microtiter plates with 150 µl of YPD medium in each well. The plates were then incubated at 30° C. for 5-7 days with shaking at 250 rpm.

Example 4: Cloning and Expression of a Variant of Penicillium vasconiae Cellobiohydrolase I (SEQ ID NO: 1) with the Substitutions V199P+E240G+ F274Y+G318P+T347P+D349V+N391D+S393D+ S394P+Y493W in Aspergillus oryzae

| Identi-fier | Sequence (5'-3') |
|---|---|
| 1216766 | ACGTCTGTCCAGGCCCAGCAGGTCGGCACTTTG (SEQ ID NO: 67) |
| 1214691 | TCGCCACGGAGCTTAATTAACTACAGGCACTGGGAGTA (SEQ ID NO: 68) |
| 1216764 | CGCGGACTGCGCACCATGAAGGGATCAATCTCCTATCAAA TCTACAAAGGTGCCCTGCTCCTCTCGGCCCTTTTGACGTC TGTCCAGGCC (SEQ ID NO: 69) |
| 1216765 | GGCCTGGACAGACGTCAAAAGGGCCGAGAGGAGCAGGGCA CCTTTGTAGATTTGATAGGAGATTGATCCCTTCATGGTGC GCAGTCCGCG (SEQ ID NO: 70) |
| 1216927 | GTGCGCAGCACCGGTGGTGCTCGAGCCAGT (SEQ ID NO: 71) |
| 1216926 | ACTGGCTCGAGCACCACCGGTGCTGCGCACTGGGCCCAGT GTGGTGGA (SEQ ID NO: 72) |
| 1217484 | ATATACACAACTGGATTTACATGAAGGGATCAATCTCCTA (SEQ ID NO: 73) |
| 1217485 | GTGTCAGTCACCTCTAGTTACTACAGGCACTGGGAGTAAT (SEQ ID NO: 74) |

Underlined characters in primers 1216764 and 1216765 indicate vector overlap sequence for cloning. The underlined section of primer 1216926 indicates a sequence codon change for the Y493W substitution.

Expression plasmid pLSBF136 was constructed as follows. The mature polypeptide sequence of variant R23 (SEQ ID NO: 1 with the substitutions V199P+E240G+F274Y+ G318P+T347P+D349V+N391D+S393D+S394P) was PCR amplified from the yeast strain in which it was originally created using primers 1216766 and 1214691. Oligos 1216764 and 1216765 were annealed to create the native Penicillium vasconiae cellobiohydrolase I signal sequence (nucleotides 1-75 of SEQ ID NO: 75). These two fragments were then cloned into a linearized plasmid using an IN-FUSION® Kit. The resulting colonies were screened via colony PCR and Sanger sequencing to identify a colony with the expected sequence. The plasmid was designated pLSB136.

Plasmid pAJ302-2 was constructed to add an additional amino acid substitution, Y493W, in the carbohydrate binding module of the P. vasconiae cellobiohydrolase I variant of pLSBF136. It was constructed by generating and sub-cloning three DNA fragments into the expression vector pJyS165 (WO 2016/145084).

The first fragment (fragment 1) consisted of (5' to 3') 15 bp of 5' upstream untranslated homologous pJyS165 sequence for sub-cloning into pJyS165 (below underlined) and the P. vasconiae signal sequence, which was generated by annealing two single stranded oligos to form a single double stranded DNA fragment. The primers used were primer 1216764 and primer 1216765.

The primers were annealed by first dissolving each oligo in annealing buffer (10 mM Tris, pH 7.5, 50 mM NaCl) to make a 100 ng/μl stock solution. A 20 μl aliquot of each oligo stock was mixed and heated to 95° C. and then cooled to 20° C. for 15 minutes. Fragment 1 was also designed to contain 15 bp of 5' upstream sequence for sub-cloning into pJyS165.

Fragment 2 consisted of (5' to 3') 15 bp of the 3' end of homologous P. vasconiae cellobiohydrolase I signal sequence and the first 1476 bp of P. vasconiae cellobiohydrolase I mature sequence (SEQ ID NO: 75), which was generated by PCR amplifying P. vasconiae cellobiohydrolase I variant pLSBF136 using PCR primer 1216766 and primer 1216927.

Fragment 3 consisted of a portion of the P. vasconiae cellobiohydrolase I CDS starting at bp 1522 (relative to the methionine start codon), sequence to the transcriptional stop (TAG), and 20 bp of 3' downstream homologous sequence to pJyS165 for sub-cloning. Fragment 3 was amplified using the following PCR primers 1216926 and 1214691.

Fragments 1 and 2 were digested with 80 μl of Dpn I restriction endonuclease at 37° C. for 60 minutes. Each product was then purified using a NUCLEOSPIN® Clean-Up Kit (Clontech Laboratories, Inc.) according to the manufacturer's protocol. The final elution of each fragment from the NucleoSpin columns was performed using 50 μl of water each.

Fragments 1, 2 and 3 were sub-cloned into pJyS165 using an IN-FUSION® HD Cloning Kit (Clontech Laboratories, Inc.).

Sequence fidelity of several correct transformants was verified using Sanger sequencing and one plasmid was named pAJ302-2.

A. oryzae expression plasmid pLSBF140 (expressing the R23 variant plus the Y493W mutation) was constructed as follows. The Penicillium vasconiae cellobiohydrolase I variant coding sequence (including the native signal sequence) was PCR amplified from pAJ302-2 using primers 1217484 and 1217485. The amplified fragment was then cloned into linearized pALLO2 (U.S. Pat. No. 7,354,743) using an IN-FUSION® Kit. Sanger sequencing was used to identify a colony with the expected sequence. The plasmid was designated pLSBF140.

Plasmid pLSBF140 was subsequently transformed into competent cells of A. oryzae strain JAL250 (EP 1157095). Transformants were evaluated using 24 well microtiter cultures and transformants were then grown in larger volumes in 2.8 L baffled shake flasks for 3 days in M400 medium at 34° C. Shake flask broths were sterile filtered using a 0.22 μm filter.

Example 5: Purification of a Variant of Penicillium vasconiae Cellobiohydrolase I (SEQ ID NO: 1) with the Substitutions V199P+E240G+F274Y+ G318P+T347P+D349V+N391D+S393D+S394P+ Y493W Expressed in Aspergillus oryzae The Aspergillus oryzae broth was adjusted to pH 7.5 and a final concentration of 1.0 M ammonium sulfate, 20 mM Tris. The broth was then filtered using a 0.22 μm polyethersulfone membrane (Millipore) to remove particulates. The filtered sample was applied to a 75 mL Phenyl Sepharose HP column (GE Healthcare) equilibrated with 1.0 M ammonium sulfate in 20 mM Tris-HCl pH 7.5. Bound proteins were eluted with a decreasing salt gradient (10 column volumes) of 1.0 M ammonium sulfate to 0 M ammonium sulfate in 20 mM Tris-HCl pH 7.5 where 5 mL fractions were collected. Fractions were analyzed using 8-16% CRITERION™ TGX Stain-Free™ SDS-PAGE gels (Bio-Rad Laboratories, Inc.). Fractions 12-30 containing the cellobiohydrolase I variant were pooled and were greater than 90% pure as judged by SDS-PAGE. The pooled material was buffer exchanged into 50 mM sodium acetate pH 5, 100 mM NaCl using four HiPrep™ 26/10 desalting columns (GE Healthcare) linked in series. Protein concentration was determined by measuring the absorbance at 280 nm and using the calculated extinction coefficient of 1.52 (where a 1 mg/mL solution of the protein would have an absorbance at 280 nm of 1.52).

Example 6: Thermal Shift Assay for Tm Determination of Variants

Protein thermal unfolding of the *Penicillium vasconiae* variants was performed as described in Example 10 of WO 2013/163590. Measured melting temperatures for both the wild-type and variants are shown in Table 2.

TABLE 2

Tm Values of *P. vasconiae* Wild-Type and Variants

| Sample | Measured Tm (° C.) |
| --- | --- |
| *P. vasconiae* cellobiohydrolase I Wild-Type (SEQ ID NO: 1) | 64 |
| T8A | 64.3 |
| T8P | 64.5 |
| S17Q | 64.4 |
| N113D | 64.3 |
| K157R | 64.4 |
| S159P | 64.4 |
| D184N | 64.3 |
| V199P | 65.3 |
| E240G | 65.4 |
| S250D | 65.1 |
| F274Y | 65.7 |
| G318A | 65.4 |
| G318P | 65.4 |
| G318S | 64.7 |
| T325P | 65.4 |
| T328P | 64.3 |
| T347P | 65.1 |
| D349V | 65.9 |
| G358A | 64.4 |
| G360S | 64.3 |
| G360T | 64.6 |
| D380N | 64.9 |
| S393D | 64.7 |
| S394P | 65.4 |
| S393D + S394P | 66.8 |
| N391D + S393D + S394P | 67.2 |
| T412A | 64.7 |
| T430V | 64.5 |
| T347P + D349V + N391D + S393D + S394P | 70.4 |
| D349V + F274Y + N391D + S393D + S394P | 70.9 |
| V199P + E240G + F274Y + T347P + D349V | 71.6 |
| V199P + E240G + F274Y + G318P + T347P + D349V | 72.8 |
| V199P + E240G + F274Y + T325P + T347P + D349V | 72.8 |
| V199P + E240G + F274Y + G318P + T347P + D349V + N391D + S393D + S394P | 75.5 |
| V199P + E240G + F274Y + G318P + T347P + D349V + N391D + S393D + S394P + Y493W | 75.9 |

The results show that the variants have a higher Tm than the wild-type cellobiohydrolase I.

The present invention is further described by the following numbered paragraphs:

[Paragraph 1] A cellobiohydrolase variant, comprising a substitution at one or more positions corresponding to positions 8, 17, 113, 157, 159, 184, 199, 240, 250, 274, 318, 325, 328, 347, 349, 358, 360, 380, 391, 393, 394, 412, and 430 of SEQ ID NO: 1, wherein the variant has cellobiohydrolase activity, and wherein the variant has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to a parent cellobiohydrolase.

[Paragraph 2] The cellobiohydrolase variant of paragraph 1, wherein the parent cellobiohydrolase has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 1, 2, 3, 4, 5, or 6.

[Paragraph 3] The cellobiohydrolase variant of paragraph 1, wherein the parent cellobiohydrolase comprises or consists of SEQ ID NO: 1, 2, 3, 4, 5, or 6.

[Paragraph 4] The cellobiohydrolase variant of paragraph 1, wherein the parent cellobiohydrolase is a fragment of SEQ ID NO: 1, 2, 3, 4, 5, or 6, wherein the fragment has cellobiohydrolase activity.

[Paragraph 5] The cellobiohydrolase variant of paragraph 4, wherein the fragment consists of at least 85% of the amino acid residues, e.g., at least 90% of the amino acid residues or at least 95% of the amino acid residues of SEQ ID NO: 1, 2, 3, 4, 5, or 6.

[Paragraph 6] The cellobiohydrolase variant of any one of paragraphs 1-5, which has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity, but less than 100% sequence identity, to the polypeptide of SEQ ID NO: 1, 2, 3, 4, 5, or 6.

[Paragraph 7] The cellobiohydrolase variant of any one of paragraphs 1-6, which has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity, but less than 100% sequence identity, to the polypeptide of SEQ ID NO: 1.

[Paragraph 8] The cellobiohydrolase variant of any one of paragraphs 1-6, which has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity, but less than 100% sequence identity, to the polypeptide of SEQ ID NO: 2.

[Paragraph 9] The cellobiohydrolase variant of any one of paragraphs 1-6, which has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity, but less than 100% sequence identity, to the polypeptide of SEQ ID NO: 3.

[Paragraph 10] The cellobiohydrolase variant of any one of paragraphs 1-6, which has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity, but less than 100% sequence identity, to the polypeptide of SEQ ID NO: 4.

[Paragraph 11] The cellobiohydrolase variant of any one of paragraphs 1-6, which has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity, but less than 100% sequence identity, to the polypeptide of SEQ ID NO: 5.

[Paragraph 12] The cellobiohydrolase variant of any one of paragraphs 1-6, which has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity, but less than 100% sequence identity, to the polypeptide of SEQ ID NO: 6.

[Paragraph 13] The cellobiohydrolase variant of any one of paragraphs 1-12, wherein the variant consists of 400 to 525, e.g., 400 to 500, 425 to 490, 450 to 480, 460 to 485 amino acids.

[Paragraph 14] A cellobiohydrolase variant, comprising a variant catalytic domain, wherein the variant catalytic domain comprises a substitution at one or more positions corresponding to positions 8, 17, 113, 157, 159, 184, 199, 240, 250, 274, 318, 325, 328, 347, 349, 358, 360, 380, 391, 393, 394, 412, and 430 of SEQ ID NO: 1 and has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to the catalytic domain of a parent cellobiohydrolase.

[Paragraph 15] The cellobiohydrolase variant of paragraph 14, wherein the catalytic domain of the parent cellobiohydrolase has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the catalytic domain of SEQ ID NO: 1, 2, 3, 4, 5, or 6.

[Paragraph 16] The cellobiohydrolase variant of paragraph 14, wherein the catalytic domain of the parent cellobiohydrolase comprises or consists of the catalytic domain of SEQ ID NO: 1, 2, 3, 4, 5, or 6.

[Paragraph 17] The cellobiohydrolase variant of any one of paragraphs 14-16, wherein the variant catalytic domain has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to the catalytic domain of SEQ ID NO: 1.

[Paragraph 18] The cellobiohydrolase variant of any one of paragraphs 14-16, wherein the variant catalytic domain has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to the catalytic domain of SEQ ID NO: 2.

[Paragraph 19] The cellobiohydrolase variant of any one of paragraphs 14-16, wherein the variant catalytic domain has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to the catalytic domain of SEQ ID NO: 3.

[Paragraph 20] The cellobiohydrolase variant of any one of paragraphs 14-16, wherein the variant catalytic domain has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to the catalytic domain of SEQ ID NO: 4.

[Paragraph 21] The cellobiohydrolase variant of any one of paragraphs 14-16, wherein the variant catalytic domain has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to the catalytic domain of SEQ ID NO: 5.

[Paragraph 22] The cellobiohydrolase variant of any one of paragraphs 14-16, wherein the variant catalytic domain has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to the catalytic domain of SEQ ID NO: 6.

[Paragraph 23] The cellobiohydrolase variant of any one of paragraphs 14-22, which further comprises a linker.

[Paragraph 24] The cellobiohydrolase variant of paragraph 23, wherein the linker is a foreign linker.

[Paragraph 25] The cellobiohydrolase variant of any one of paragraphs 14-24, which further comprises a carbohydrate binding module.

[Paragraph 26] The cellobiohydrolase variant of paragraph 25, wherein the carbohydrate binding module is a foreign carbohydrate binding module.

[Paragraph 27] The cellobiohydrolase variant of any one of paragraphs 1-26, wherein the number of substitutions is 1-23, e.g., 1, 2, 3, 4, 5, 6, 7, 8, 9, 10, 11, 12, 13, 14, 15, 16, 17, 18, 19, 20, 21, 22, or 23 substitutions.

[Paragraph 28] The cellobiohydrolase variant of any one of paragraphs 1-27, which comprises a substitution at a position corresponding to position 8 of SEQ ID NO: 4 with Ala, Arg, Asn, Asp, Cys, Gln, Glu, Gly, His, Ile, Leu, Lys, Met, Phe, Pro, Ser, Trp, Tyr, or Val.

[Paragraph 29] The cellobiohydrolase variant of paragraph 28, wherein the substitution is with Ala or Pro.

[Paragraph 30] The cellobiohydrolase variant of paragraph 29, wherein the substitution is a Thr to Ala or Pro substitution.

[Paragraph 31] The cellobiohydrolase variant of any one of paragraphs 1-30, which comprises a substitution at a position corresponding to position 17 of SEQ ID NO: 1 with Ala, Arg, Asn, Asp, Cys, Gln, Glu, Gly, His, Ile, Leu, Lys, Met, Phe, Pro, Thr, Trp, Tyr, or Val.

[Paragraph 32] The cellobiohydrolase variant of paragraph 31, wherein the substitution is with Gln.

[Paragraph 33] The cellobiohydrolase variant of paragraph 32, wherein the substitution is a Ser to Gln substitution.

[Paragraph 34] The cellobiohydrolase variant of any one of paragraphs 1-33, which comprises a substitution at a position corresponding to position 113 of SEQ ID NO: 1 with Ala, Arg, Asp, Cys, Gln, Glu, Gly, His, Ile, Leu, Lys, Met, Phe, Pro, Ser, Thr, Trp, Tyr, or Val.

[Paragraph 35] The cellobiohydrolase variant of paragraph 34, wherein the substitution is with Asp.

[Paragraph 36] The cellobiohydrolase variant of paragraph 35, wherein the substitution is an Asn to Asp substitution.

[Paragraph 37] The cellobiohydrolase variant of any one of paragraphs 1-36, which comprises a substitution at a position corresponding to position 157 of SEQ ID NO: 1 with Ala, Arg, Asn, Asp, Cys, Gln, Glu, Gly, His, Ile, Leu, Met, Phe, Pro, Ser, Thr, Trp, Tyr, or Val.

[Paragraph 38] The cellobiohydrolase variant of paragraph 37, wherein the substitution is with Arg.

[Paragraph 39] The cellobiohydrolase variant of paragraph 38, wherein the substitution is a Lys to Arg substitution.

[Paragraph 40] The cellobiohydrolase variant of any one of paragraphs 1-39, which comprises a substitution at a position corresponding to position 159 of SEQ ID NO: 1 with Ala, Arg, Asn, Asp, Cys, Gln, Glu, Gly, His, Ile, Leu, Lys, Met, Phe, Pro, Thr, Trp, Tyr, or Val.

[Paragraph 41] The cellobiohydrolase variant of paragraph 40, wherein the substitution is with Pro.

[Paragraph 42] The cellobiohydrolase variant of paragraph 41, wherein the substitution is a Ser to Pro substitution.

[Paragraph 43] The cellobiohydrolase variant of any one of paragraphs 1-42, which comprises a substitution at a position corresponding to position 184 of SEQ ID NO: 1 with Ala, Arg, Asn, Asp, Cys, Gln, Glu, Gly, His, Ile, Leu, Lys, Met, Phe, Pro, Ser, Thr, Trp, Tyr, or Val.

[Paragraph 44] The cellobiohydrolase variant of paragraph 43, wherein the substitution is with Asn.

[Paragraph 45] The cellobiohydrolase variant of paragraph 44, wherein the substitution is an Asp to Asn substitution.

[Paragraph 46] The cellobiohydrolase variant of any one of paragraphs 1-45, which comprises a substitution at a position corresponding to position 199 of SEQ ID NO: 1 with Ala, Arg, Asn, Asp, Cys, Gln, Glu, Gly, His, Ile, Leu, Lys, Met, Phe, Pro, Ser, Thr, Trp, or Tyr.

[Paragraph 47] The cellobiohydrolase variant of paragraph 46, wherein the substitution is with Pro.

[Paragraph 48] The cellobiohydrolase variant of paragraph 47, wherein the substitution is a Val to Pro substitution.

[Paragraph 49] The cellobiohydrolase variant of any one of paragraphs 1-48, which comprises a substitution at a position corresponding to position 240 of SEQ ID NO: 1 with Ala, Arg, Asn, Asp, Cys, Gln, Gly, His, Ile, Leu, Lys, Met, Phe, Pro, Ser, Thr, Trp, Tyr, or Val.

[Paragraph 50] The cellobiohydrolase variant of paragraph 49, wherein the substitution is with Gly.

[Paragraph 51] The cellobiohydrolase variant of paragraph 50, wherein the substitution is a Glu to Gly substitution.

[Paragraph 52] The cellobiohydrolase variant of any one of paragraphs 1-51, which comprises a substitution at a position corresponding to position 250 of SEQ ID NO: 1 with Ala, Arg, Asn, Asp, Cys, Gln, Glu, Gly, His, Ile, Leu, Lys, Met, Phe, Pro, Thr, Trp, Tyr, or Val.

[Paragraph 53] The cellobiohydrolase variant of paragraph 52, wherein the substitution is with Asp.

[Paragraph 54] The cellobiohydrolase variant of paragraph 53, wherein the substitution is a Ser to Asp substitution.

[Paragraph 55] The cellobiohydrolase variant of any one of paragraphs 1-54, which comprises a substitution at a position corresponding to position 274 of SEQ ID NO: 1 with Ala, Arg, Asn, Asp, Cys, Gln, Glu, Gly, His, Ile, Leu, Lys, Met, Pro, Ser, Thr, Trp, Tyr, or Val.

[Paragraph 56] The cellobiohydrolase variant of paragraph 55, wherein the substitution is with Tyr.

[Paragraph 57] The cellobiohydrolase variant of paragraph 56, wherein the substitution is a Phe to Tyr substitution.

[Paragraph 58] The cellobiohydrolase variant of any one of paragraphs 1-57, which comprises a substitution at a position corresponding to position 318 of SEQ ID NO: 1 with Ala, Arg, Asn, Asp, Cys, Gln, Glu, His, Ile, Leu, Lys, Met, Phe, Pro, Ser, Thr, Trp, Tyr, or Val.

[Paragraph 59] The cellobiohydrolase variant of paragraph 58, wherein the substitution is with Ala, Pro, or Ser.

[Paragraph 60] The cellobiohydrolase variant of paragraph 59, wherein the substitution is a Gly to Ala, Pro, or Ser substitution.

[Paragraph 61] The cellobiohydrolase variant of any one of paragraphs 1-60, which comprises a substitution at a position corresponding to position 325 of SEQ ID NO: 1 with Ala, Arg, Asn, Asp, Cys, Gln, Glu, Gly, His, Ile, Leu, Lys, Met, Phe, Pro, Ser, Trp, Tyr, or Val.

[Paragraph 62] The cellobiohydrolase variant of paragraph 61, wherein the substitution is with Pro.

[Paragraph 63] The cellobiohydrolase variant of paragraph 62, wherein the substitution is a Thr to Pro substitution.

[Paragraph 64] The cellobiohydrolase variant of any one of paragraphs 1-63, which comprises a substitution at a position corresponding to position 328 of SEQ ID NO: 1 with Ala, Arg, Asn, Asp, Cys, Gln, Glu, Gly, His, Ile, Leu, Lys, Met, Phe, Pro, Ser, Trp, Tyr, or Val.

[Paragraph 65] The cellobiohydrolase variant of paragraph 64, wherein the substitution is with Pro.

[Paragraph 66] The cellobiohydrolase variant of paragraph 65, wherein the substitution is a Thr to Pro substitution.

[Paragraph 67] The cellobiohydrolase variant of any one of paragraphs 1-66, which comprises a substitution at a position corresponding to position 347 of SEQ ID NO: 1 with Ala, Arg, Asn, Asp, Cys, Gln, Glu, Gly, His, Ile, Leu, Lys, Met, Phe, Pro, Ser, Trp, Tyr, or Val.

[Paragraph 68] The cellobiohydrolase variant of paragraph 67, wherein the substitution is with Pro.

[Paragraph 69] The cellobiohydrolase variant of paragraph 68, wherein the substitution is a Thr to Pro substitution.

[Paragraph 70] The cellobiohydrolase variant of any one of paragraphs 1-69, which comprises a substitution at a position corresponding to position 349 of SEQ ID NO: 1 with Ala, Arg, Asn, Cys, Gln, Glu, Gly, His, Ile, Leu, Lys, Met, Phe, Pro, Ser, Thr, Trp, Tyr, or Val.

[Paragraph 71] The cellobiohydrolase variant of paragraph 70, wherein the substitution is with Val.

[Paragraph 72] The cellobiohydrolase variant of paragraph 71, wherein the substitution is an Asp to Val substitution.

[Paragraph 73] The cellobiohydrolase variant of any one of paragraphs 1-72, which comprises a substitution at a position corresponding to position 358 of SEQ ID NO: 1 with Ala, Arg, Asn, Asp, Cys, Gln, Glu, His, Ile, Leu, Lys, Met, Phe, Pro, Ser, Thr, Trp, Tyr, or Val.

[Paragraph 74] The cellobiohydrolase variant of paragraph 73, wherein the substitution is with Ala.

[Paragraph 75] The cellobiohydrolase variant of paragraph 74, wherein the substitution is a Gly to Ala substitution.

[Paragraph 76] The cellobiohydrolase variant of any one of paragraphs 1-75, which comprises a substitution at a position corresponding to position 360 of SEQ ID NO: 1 with Ala, Arg, Asn, Asp, Cys, Gln, Glu, His, Ile, Leu, Lys, Met, Phe, Pro, Ser, Thr, Trp, Tyr, or Val.

[Paragraph 77] The cellobiohydrolase variant of paragraph 76, wherein the substitution is with Ser or Thr.

[Paragraph 78] The cellobiohydrolase variant of paragraph 77, wherein the substitution is a Gly to Ser or Thr substitution.

[Paragraph 79] The cellobiohydrolase variant of any one of paragraphs 1-78, which comprises a substitution at a position corresponding to position 380 of SEQ ID NO: 1 with Ala, Arg, Asn, Cys, Gln, Glu, Gly, His, Ile, Leu, Lys, Met, Phe, Pro, Ser, Thr, Trp, Tyr, or Val.

[Paragraph 80] The cellobiohydrolase variant of paragraph 79, wherein the substitution is with Asn.

[Paragraph 81] The cellobiohydrolase variant of paragraph 80, wherein the substitution is an Asp to Asn substitution.

[Paragraph 82] The cellobiohydrolase variant of any one of paragraphs 1-81, which comprises a substitution at a position corresponding to position 391 of SEQ ID NO: 1 with Ala, Arg, Asp, Cys, Gln, Glu, Gly, His, Ile, Leu, Lys, Met, Phe, Pro, Ser, Thr, Trp, Tyr, or Val.

[Paragraph 83] The cellobiohydrolase variant of paragraph 82, wherein the substitution is with Asp.

[Paragraph 84] The cellobiohydrolase variant of paragraph 83, wherein the substitution is an Asn to Asp substitution.

[Paragraph 85] The cellobiohydrolase variant of any one of paragraphs 1-84, which comprises a substitution at a position corresponding to position 393 of SEQ ID NO: 1 with Ala, Arg, Asn, Asp, Cys, Gln, Glu, Gly, His, Ile, Leu, Lys, Met, Phe, Pro, Thr, Trp, Tyr, or Val.

[Paragraph 86] The cellobiohydrolase variant of paragraph 85, wherein the substitution is with Asp.

[Paragraph 87] The cellobiohydrolase variant of paragraph 86, wherein the substitution is a Ser to Asp substitution.

[Paragraph 88] The cellobiohydrolase variant of any one of paragraphs 1-87, which comprises a substitution at a position corresponding to position 394 of SEQ ID NO: 1 with Ala, Arg, Asn, Asp, Cys, Gln, Glu, Gly, His, Ile, Leu, Lys, Met, Phe, Pro, Thr, Trp, Tyr, or Val.

[Paragraph 89] The cellobiohydrolase variant of paragraph 88, wherein the substitution is with Pro.

[Paragraph 90] The cellobiohydrolase variant of paragraph 89, wherein the substitution is a Ser to Pro substitution.

[Paragraph 91] The cellobiohydrolase variant of any one of paragraphs 1-90, which comprises a substitution at a position corresponding to position 412 of SEQ ID NO: 1 with Ala, Arg, Asn, Asp, Cys, Gln, Glu, Gly, His, Ile, Leu, Lys, Met, Phe, Pro, Ser, Trp, Tyr, or Val.

[Paragraph 92] The cellobiohydrolase variant of paragraph 91, wherein the substitution is with Ala.

[Paragraph 93] The cellobiohydrolase variant of paragraph 92, wherein the substitution is a Thr to Ala substitution.

[Paragraph 94] The cellobiohydrolase variant of any one of paragraphs 1-93, which comprises a substitution at a position corresponding to position 430 of SEQ ID NO: 1 with Ala, Arg, Asn, Asp, Cys, Gln, Glu, Gly, His, Ile, Leu, Lys, Met, Phe, Pro, Ser, Trp, Tyr, or Val.

[Paragraph 95] The cellobiohydrolase variant of paragraph 94, wherein the substitution is with Val.

[Paragraph 96] The cellobiohydrolase variant of paragraph 95, wherein the substitution is a Thr to Val substitution.

[Paragraph 97] The cellobiohydrolase variant of any one of paragraphs 1-96, which further comprises an alteration at one or more positions corresponding to positions 4, 21, 26, 38, 39, 44, 45, 46, 51, 52, 53, 54, 72, 75, 87, 93, 94, 95, 100, 102, 108, 111, 114, 129, 130, 131, 137, 138, 139, 144, 150, 156, 157, 183, 184, 187, 194, 195, 196, 197, 198, 199, 200, 201, 205, 206, 209, 211, 219, 237, 241, 247, 253, 260, 264, 271, 280, 320, 322, 330, 332, 343, 345, 350, 357, 358, 360, 365, 371, 375, 379, 380, 381, 382, 385, 386, 389, 390, 392, 397, 400, 405, 407, 413, 426, 427, 430, 440, 444, 445, 446, 447, 450, 453, 455, 456, 458, 459, 462, 463, 464, 492, 493, 494, 496, 497, 498, 502, 503, 507, 510, 513, 515, 516, and 517 of SEQ ID NO: 1, e.g., G4C, A21P, S26A, W38A, R39L, T44I, T44M, T44N, T44K, S45D, S45N, G46A, G46I, G46L, G46T, Y51I, T52R, T52W, G53A, G53M, G53R, G53W, N54S, N54I, N54D, A72C, G75S, S87T, L93V, N94S, N94A, N94R, N94Q, F95L, F95Y, S100T, S100V, S100W, S100L, S100G, K102S, K102R, L108I, L111T, D114E, F129S, D130N, D130E, V131A, P137S, 0138S, G139E, G139M, G139Q, G139S, G139R, L144A, L144V, D150N, A156G, K157R, I183N, D184S, A187L, P194*, P194Q, S195*, T196*, N197A, N197*, D198A, D198*, V199*, N200A, N200G, N200W, N200F, N200C, N200*, S201*, N205R, H206Y, C209S, A211T, N219S, M237T, D241L, D241R, D241V, Y247C, A253D, A253R, G260D, N264Y, T271I, V280I, P320A, S322V, N330D, I332F, A343V, G345D, F350L, A357S, G358R, G360M, D365S, M371V, D375A, D375G, A379T, D380H, D380Y, M381V, L382A, D385E, S386C, S386E, P389L, P389Q, P389I, T390A, T390S, T390A, A392G, A392I, A392L, P397A, P397G, P397K, P397W, P397C, P397L, K400A, D405P, S407G, T413P, S426F, N427D, T430Y, T440L, T440R, T440G, T444S, T445D, S446T, S447L, T450D, S453D, T455A, T456S, S458E, K459E, K459S, S462I, T463I, T464A, T464A, H492L, Y493S, Y493W, A494D, A494S, C496S, C496Y, G497C, G498D, G498S, T502N, G503D, C507Y, P510V, P510S, C513R, C513W, K515D, Q516P, and N517D.

[Paragraph 98] The cellobiohydrolase variant of any one of paragraphs 1-97, which has an increased thermal activity or increased thermostability relative to the parent.

[Paragraph 99] The cellobiohydrolase variant of any one of paragraphs 1-98, which has cellobiohydrolase I activity.

[Paragraph 100] An enzyme composition comprising the cellobiohydrolase variant of any one of paragraphs 1-99.

[Paragraph 101] The enzyme composition of paragraph 100, further comprising one or more enzymes selected from the group consisting of a cellulase, an AA9 polypeptide, a hemicellulase, a CIP, an esterase, an expansin, a ligninolytic enzyme, an oxidoreductase, a pectinase, a protease, and a swollenin.

[Paragraph 102] The process of paragraph 101, wherein the cellulase is one or more enzymes selected from the group consisting of an endoglucanase, a cellobiohydrolase, and a beta-glucosidase.

[Paragraph 103] The process of paragraph 101, wherein the hemicellulase is one or more enzymes selected from the group consisting of a xylanase, an acetylxylan esterase, a feruloyl esterase, an arabinofuranosidase, a xylosidase, and a glucuronidase.

[Paragraph 104] The enzyme composition of any one of paragraphs 100-103, further comprising a catalase.

[Paragraph 105] An isolated polynucleotide encoding the cellobiohydrolase variant of any one of paragraphs 1-99, which is operably linked to one or more control sequences that direct the production of the polypeptide in an expression host.

[Paragraph 106] A nucleic acid construct comprising the polynucleotide of paragraph 105

[Paragraph 107] An expression vector comprising the polynucleotide of paragraph 105.

[Paragraph 108] A recombinant host cell comprising the polynucleotide of paragraph 105.

[Paragraph 109] A method of producing a cellobiohydrolase variant, comprising:
(a) cultivating the recombinant host cell of paragraph 108 under conditions suitable for expression of the variant; and optionally
(b) recovering the variant.

[Paragraph 110] A transgenic plant, plant part or plant cell transformed with the polynucleotide of paragraph 105.

[Paragraph 111] A method of producing a cellobiohydrolase variant, comprising:
(a) cultivating a transgenic plant, plant part or a plant cell of paragraph 110 under conditions conducive for production of the variant; and optionally
(b) recovering the variant.

[Paragraph 112] A method for obtaining a cellobiohydrolase variant, comprising introducing into a parent cellobiohydrolase a substitution at one or more positions corresponding to positions 8, 17, 113, 157, 159, 184, 199, 240, 250, 274, 318, 325, 328, 347, 349, 358, 360, 380, 391, 393, 394, 412, and 430 of the polypeptide of SEQ ID NO: 1, wherein the cellobiohydrolase variant has cellobiohydrolase activity; and recovering the variant.

[Paragraph 113] A whole broth formulation or cell culture composition comprising the cellobiohydrolase variant of any one of paragraphs 1-99.

[Paragraph 114] A process for degrading a cellulosic material, comprising: treating the cellulosic material with an enzyme composition comprising the cellobiohydrolase variant of any one of paragraphs 1-99.

[Paragraph 115] The process of paragraph 114, wherein the cellulosic material is pretreated.

[Paragraph 116] The process of paragraph 114 or 115, wherein the enzyme composition further comprises one or more enzymes selected from the group consisting of a cellulase, an AA9 polypeptide, a hemicellulase, a CIP, an esterase, an expansin, a ligninolytic enzyme, an oxidoreductase, a pectinase, a protease, and a swollenin.

[Paragraph 117] The process of paragraph 116, wherein the cellulase is one or more enzymes selected from the group consisting of an endoglucanase, a cellobiohydrolase, and a beta-glucosidase.

[Paragraph 118] The process of paragraph 116, wherein the hemicellulase is one or more enzymes selected from the group consisting of a xylanase, an acetylxylan esterase, a feruloyl esterase, an arabinofuranosidase, a xylosidase, and a glucuronidase.

[Paragraph 119] The process of any one of paragraphs 114-118, further comprising recovering the degraded cellulosic material.

[Paragraph 120] The process of paragraph 119, wherein the degraded cellulosic material is a sugar.

[Paragraph 121] The process of paragraph 120, wherein the sugar is selected from the group consisting of glucose, xylose, mannose, galactose, and arabinose.

[Paragraph 122] A process for producing a fermentation product, comprising:
(a) saccharifying a cellulosic material with an enzyme composition comprising a cellobiohydrolase variant of any one of paragraphs 1-99;
(b) fermenting the saccharified cellulosic material with one or more fermenting microorganisms to produce the fermentation product; and
(c) recovering the fermentation product from the fermentation.

[Paragraph 123] The process of paragraph 122, wherein the cellulosic material is pretreated.

[Paragraph 124] The process of paragraph 122 or 123, wherein the enzyme composition further comprises one or more enzymes selected from the group consisting of a cellulase, an AA9 polypeptide, a hemicellulase, a CIP, an esterase, an expansin, a ligninolytic enzyme, an oxidoreductase, a pectinase, a protease, and a swollenin.

[Paragraph 125] The process of paragraph 124, wherein the cellulase is one or more enzymes selected from the group consisting of an endoglucanase, a cellobiohydrolase, and a beta-glucosidase.

[Paragraph 126] The process of paragraph 124, wherein the hemicellulase is one or more enzymes selected from the group consisting of a xylanase, an acetylxylan esterase, a feruloyl esterase, an arabinofuranosidase, a xylosidase, and a glucuronidase.

[Paragraph 127] The process of any one of paragraphs 122-126, wherein steps (a) and (b) are performed simultaneously in a simultaneous saccharification and fermentation.

[Paragraph 128] The process of any one of paragraphs 122-127, wherein the fermentation product is an alcohol, an alkane, a cycloalkane, an alkene, an amino acid, a gas, isoprene, a ketone, an organic acid, or polyketide.

[Paragraph 129] A process of fermenting a cellulosic material, comprising: fermenting the cellulosic material with one or more fermenting microorganisms, wherein the cellulosic material is saccharified with an enzyme composition comprising a cellobiohydrolase variant of any one of paragraphs 1-99.

[Paragraph 130] The process of paragraph 129, wherein the fermenting of the cellulosic material produces a fermentation product.

[Paragraph 131] The process of paragraph 130, further comprising recovering the fermentation product from the fermentation.

[Paragraph 132] The process of paragraph 130 or 131, wherein the fermentation product is an alcohol, an alkane, a cycloalkane, an alkene, an amino acid, a gas, isoprene, a ketone, an organic acid, or polyketide.

[Paragraph 133] The process of any one of paragraphs 129-132, wherein the cellulosic material is pretreated before saccharification.

[Paragraph 134] The process of any one of paragraphs 129-133, wherein the enzyme composition further comprises one or more enzymes selected from the group consisting of a cellulase, an AA9 polypeptide, a hemicellulase, a CIP, an esterase, an expansin, a ligninolytic enzyme, an oxidoreductase, a pectinase, a protease, and a swollenin.

[Paragraph 135] The process of paragraph 134, wherein the cellulase is one or more enzymes selected from the group consisting of an endoglucanase, a cellobiohydrolase, and a beta-glucosidase.

[Paragraph 136] The process of paragraph 134, wherein the hemicellulase is one or more enzymes selected from the group consisting of a xylanase, an acetylxylan esterase, a feruloyl esterase, an arabinofuranosidase, a xylosidase, and a glucuronidase.

[Paragraph 137] The process of any one of paragraphs 114-136, wherein oxygen is added during saccharification to maintain a concentration of dissolved oxygen of at least 0.5% of the saturation level.

[Paragraph 138] The process of paragraph 137, wherein the dissolved oxygen concentration during saccharification is in the range of 0.5-10% of the saturation level, such as 0.5-7%, such as 0.5-5%, such as 0.5-4%, such as 0.5-3%, such as 0.5-2%, such as 1-5%, such as 1-4%, such as 1-3%, such as 1-2%.

[Paragraph 139] The process of any one of paragraphs 114-138, wherein the enzyme composition further comprises a catalase.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

What is claimed is:

1. A cellobiohydrolase variant, comprising a substitution relative to SEQ ID NO: 1 at one or more of positions 113, 157, 199, 240, 250, 274, 318, 325, 328, 347, 349, 358, 360, 391, 393, 394, 412, and 430 of SEQ ID NO: 1, wherein the variant has: (1) cellobiohydrolase activity, (2) at least 90%, but less than 100%, sequence identity to SEQ ID NO: 1, and (3) an increased thermal activity or increased thermostability relative to the cellobiohydrolase of SEQ ID NO: 1.

2. The cellobiohydrolase variant of claim 1, which comprises one or more substitutions selected from the group consisting of: N113D; K157R; V199P; S250D; F274Y; G318A,P,S; T325P; T328P; T347P; D349V; G358A; G360S,T; N391D; S393D; S394P; T412A; and T430V.

3. The cellobiohydrolase variant of claim 1, which further comprises an alteration at one or more positions corresponding to positions 4, 8, 17, 21, 26, 38, 39, 44, 45, 46, 51, 52, 53, 54, 72, 75, 87, 93, 94, 95, 100, 102, 108, 111, 114, 129, 130, 131, 137, 138, 139, 144, 150, 156, 157, 159, 183, 184, 187, 194, 195, 196, 197, 198, 199, 200, 201, 205, 206, 209, 211, 219, 237, 240, 241, 247, 253, 260, 264, 271, 280, 320, 322, 330, 332, 343, 345, 350, 357, 358, 360, 365, 371, 375, 379, 380, 381, 382, 385, 386, 389, 390, 392, 397, 400, 405, 407, 413, 426, 427, 430, 440, 444, 445, 446, 447, 450, 453, 455, 456, 458, 459, 462, 463, 464, 492, 493, 494, 496, 497, 498, 502, 503, 507, 510, 513, 515, 516, and 517 of SEQ ID NO: 1.

4. The cellobiohydrolase variant of claim 3, wherein the alteration is selected from the group consisting of G4C, A21P, S26A, W38A, R39L, T44I, T44M, T44N, T44K, S45D, S45N, G46A, G46I, G46L, G46T, Y51I, T52R, T52W, G53A, G53M, G53R, G53W, N54S, N54I, N54D, A72C, G75S, S87T, L93V, N94S, N94A, N94R, N94Q, F95L, F95Y, S100T, S100V, S100W, S100L, S100G, K102S, K102R, L108I, L111T, D114E, F129S, D130N, D130E, V131A, P137S, C138S, G139E, G139M, G139Q, G139S, G139R, L144A, L144V, D150N, A156G, K157R, S159P, I183N, D184S, A187L, P194*, P194Q, S195*, T196*, N197A, N197*, D198A, D198*, V199*, N200A, N200G, N200W, N200F, N200O, N200*, S201*, N205R, H206Y, C209S, A211T, N219S, M237T, D241L, D241R, D241V, Y247C, A253D, A253R, G260D, N264Y, T271I, V280I, P320A, S322V, N330D, I332F, A343V, G345D, F350L, A357S, G358R, G360M, D365S, M371V, D375A, D375G, A379T, D380H, D380Y, D380N, M381V, L382A, D385E, S386C, S386P, P389L, P389Q, P389I, T390A, T390S, T390A, A392G, A392I, A392L, P397A, P397G, P397K, P397W, P397G, P397L, K400A, D405P, S407G, T413P, S426F, N427D, T430Y, T440L, T440R, T440G, T444S, T445D, S446T, S447L, T450D, S453D, T455A, T456S, S458E, K459E, K459S, S462I, T463I, T464A, T464A, H492L, Y493S, Y493W, A494D, A494S, C496S, C496Y, G497C, G498D, G498S, T502N, G503D, O507Y, P510V, P510S, O513R, O513W, K515D, Q516P, and N517D.

5. The cellobiohydrolase variant of claim 3, which has at least 95%, but less than 100% sequence identity, to the polypeptide of SEQ ID NO: 1.

6. The cellobiohydrolase variant of claim 1, which has at least 95%, but less than 100% sequence identity, to the polypeptide of SEQ ID NO: 1.

7. The cellobiohydrolase variant of claim 6, which comprises one or more substitutions selected from the group consisting of: N113D; K157R; V199P; S250D; F274Y; G318A,P,S; T325P; T328P; T347P; D349V; G358A; G360S,T; N391D; S393D; S394P; T412A; and T430V.

8. The cellobiohydrolase variant of claim 7, which further comprises an alteration at one or more positions corresponding to positions 4, 8, 17, 21, 26, 38, 39, 44, 45, 46, 51, 52, 53, 54, 72, 75, 87, 93, 94, 95, 100, 102, 108, 111, 114, 129, 130, 131, 137, 138, 139, 144, 150, 156, 157, 159, 183, 184, 187, 194, 195, 196, 197, 198, 199, 200, 201, 205, 206, 209, 211, 219, 237, 240, 241, 247, 253, 260, 264, 271, 280, 320, 322, 330, 332, 343, 345, 350, 357, 358, 360, 365, 371, 375, 379, 380, 381, 382, 385, 386, 389, 390, 392, 397, 400, 405, 407, 413, 426, 427, 430, 440, 444, 445, 446, 447, 450, 453, 455, 456, 458, 459, 462, 463, 464, 492, 493, 494, 496, 497, 498, 502, 503, 507, 510, 513, 515, 516, and 517 of SEQ ID NO: 1.

9. The cellobiohydrolase variant of claim 8, wherein the alteration is selected from the group consisting of G4C, A21P, S26A, W38A, R39L, T44I, T44M, T44N, T44K, S45D, S45N, G46A, G46I, G46L, G46T, Y51I, T52R, T52W, G53A, G53M, G53R, G53W, N54S, N54I, N54D, A72C, G75S, S87T, L93V, N94S, N94A, N94R, N94Q, F95L, F95Y, S100T, S100V, S100W, S100L, S100G, K102S, K102R, L108I, L111T, D114E, F129S, D130N, D130E, V131A, P137S, 0138S, G139E, G139M, G139Q, G139S, G139R, L144A, L144V, D150N, A156G, K157R, S159P, 1183N, D184S, A187L, P194*, P194Q, S195*, T196*, N197A, N197*, D198A, D198*, V199*, N200A, N200G, N200W, N200F, N200Q, N200*, S201*, N205R, H206Y, C209S, A211T, N219S, M237T, D241L, D241R, D241V, Y247C, A253D, A253R, G260D, N264Y, T271I, V280I, P320A, S322V, N330D, 1332F, A343V, G345D, F350L, A357S, G358R, G360M, D365S, M371V, D375A, D375G, A379T, D380H, D380Y, D380N, M381V, L382A, D385E, S386C, S386E, P389L, P389Q, P389I, T390A, T390S, T390A, A392G, A392I, A392L, P397A, P397G, P397K, P397W, P397G, P397L, K400A, D405P, S407G, T413P, S426F, N427D, T430Y, T440L, T440R, T440G, T444S, T445D, S446T, S447L, T450D, S453D, T455A, T456S, S458E, K459E, K459S, S462I, T463I, T464A, T464A, H492L, Y493S, Y493W, A494D, A494S, C496S, C496Y, G497C, G498D, G498S, T502N, G503D, C507Y, P510V, P510S, C513R, C513W, K515D, Q516P, and N517D.

10. The cellobiohydrolase variant of claim 1, which comprises a N113D substitution.

11. The cellobiohydrolase variant of claim 1, which comprises a K157R substitution.

12. The cellobiohydrolase variant of claim 11, which has at least 95%, but less than 100% sequence identity, to the polypeptide of SEQ ID NO: 1.

13. The cellobiohydrolase variant of claim 1, which comprises a V199P substitution.

14. The cellobiohydrolase variant of claim 13, which has at least 95%, but less than 100% sequence identity, to the polypeptide of SEQ ID NO: 1.

15. The cellobiohydrolase variant of claim 1, which comprises a S250D substitution.

16. The cellobiohydrolase variant of claim 15, which has at least 95%, but less than 100% sequence identity, to the polypeptide of SEQ ID NO: 1.

17. The cellobiohydrolase variant of claim 1, which comprises a F274Y substitution.

18. The cellobiohydrolase variant of claim 17, which has at least 95%, but less than 100% sequence identity, to the polypeptide of SEQ ID NO: 1.

19. The cellobiohydrolase variant of claim 1, which comprises a G318A, P, or S substitution.

20. The cellobiohydrolase variant of claim 19, which has at least 95%, but less than 100% sequence identity, to the polypeptide of SEQ ID NO: 1.

21. The cellobiohydrolase variant of claim 1, which comprises a T325P substitution.

22. The cellobiohydrolase variant of claim 21, which has at least 95%, but less than 100% sequence identity, to the polypeptide of SEQ ID NO: 1.

23. The cellobiohydrolase variant of claim 1, which comprises a T328P substitution.

24. The cellobiohydrolase variant of claim 23, which has at least 95%, but less than 100% sequence identity, to the polypeptide of SEQ ID NO: 1.

25. The cellobiohydrolase variant of claim 1, which comprises a T347P substitution.

26. The cellobiohydrolase variant of claim 25, which has at least 95%, but less than 100% sequence identity, to the polypeptide of SEQ ID NO: 1.

27. The cellobiohydrolase variant of claim 1, which comprises a D349V substitution.

28. The cellobiohydrolase variant of claim 27, which has at least 95%, but less than 100% sequence identity, to the polypeptide of SEQ ID NO: 1.

29. The cellobiohydrolase variant of claim 1, which comprises a G358A substitution.

30. The cellobiohydrolase variant of claim 29, which has at least 95%, but less than 100% sequence identity, to the polypeptide of SEQ ID NO: 1.

31. The cellobiohydrolase variant of claim 1, which comprises a G360S or T substitution.

32. The cellobiohydrolase variant of claim 31, which has at least 95%, but less than 100% sequence identity, to the polypeptide of SEQ ID NO: 1.

33. The cellobiohydrolase variant of claim 1, which comprises a N391D substitution.

34. The cellobiohydrolase variant of claim 33, which has at least 95%, but less than 100% sequence identity, to the polypeptide of SEQ ID NO: 1.

35. The cellobiohydrolase variant of claim 1, which comprises a S393D substitution.

36. The cellobiohydrolase variant of claim 35, which has at least 95%, but less than 100% sequence identity, to the polypeptide of SEQ ID NO: 1.

37. The cellobiohydrolase variant of claim 1, which comprises a S394P substitution.

38. The cellobiohydrolase variant of claim 37, which has at least 95%, but less than 100% sequence identity, to the polypeptide of SEQ ID NO: 1.

39. The cellobiohydrolase variant of claim 1, which comprises a T412A substitution.

40. The cellobiohydrolase variant of claim 39, which has at least 95%, but less than 100% sequence identity, to the polypeptide of SEQ ID NO: 1.

41. The cellobiohydrolase variant of claim 1, which comprises a T430V substitution.

42. The cellobiohydrolase variant of claim 41, which has at least 95%, but less than 100% sequence identity, to the polypeptide of SEQ ID NO: 1.

43. A method for obtaining a cellobiohydrolase variant, comprising introducing into a parent cellobiohydrolase a substitution at one or more positions corresponding to positions 113, 157, 159, 199, 250, 274, 318, 325, 328, 347, 349, 358, 360, 380, 391, 393, 394, 412, and 430 of the polypeptide of SEQ ID NO: 1, wherein the variant has: (1) cellobiohydrolase activity, (2) at least 90%, but less than 100%, sequence identity to SEQ ID NO: 1, and (3) an increased thermal activity or increased thermostability relative to the cellobiohydrolase of SEQ ID NO: 1.

44. The method of claim 43, wherein the substitution is selected from the group consisting of: N113D; K157R; V199P; S250D; F274Y; G318A,P,S; T325P; T328P; T347P; D349V; G358A; G360S,T; N391D; S393D; S394P; T412A; and T430V.

45. The method of claim 44, wherein the variant has at least 95%, but less than 100% sequence identity, to the polypeptide of SEQ ID NO: 1.

* * * * *

UNITED STATES PATENT AND TRADEMARK OFFICE
CERTIFICATE OF CORRECTION

PATENT NO. : 11,965,189 B2
APPLICATION NO. : 16/088038
DATED : April 23, 2024
INVENTOR(S) : Wogulis et al.

It is certified that error appears in the above-identified patent and that said Letters Patent is hereby corrected as shown below:

In the Claims

Please amend Claim 4 (Column 125, Line 56 – Column 126, Line 43) as follows:
4. The cellobiohydrolase variant of claim 3, wherein the alteration is selected from the group consisting of G4C, A21P, S26A, W38A, R39L, T44I, T44M, T44N, T44K, S45D, S45N, G46A, G46I, G46L, G46T, Y51I, T52R, T52W, G53A, G53M, G53R, G53W, N54S, N54I, N54D, A72C, G75S, S87T, L93V, N94S, N94A, N94R, N94Q, F95L, F95Y, S100T, S100V, S100W, S100L, S100G, K102S, K102R, L108I, L111T, D114E, F129S, D130N, D130E, V131A, P137S, C138S, G139E, G139M, G139Q, G139S, G139R, L144A, L144V, D150N, A156G, K157R, S159P, I183N, D184S, A187L, P194*, P194Q, S195*, T196*, N197A, N197*, D198A, D198*, V199*, N200A, N200G, N200W, N200F, N200C, N200*, S201*, N205R, H206Y, C209S, A211T, N219S, M237T, D241L, D241R, D241V, Y247C, A253D, A253R, G260D, N264Y, T271I, V280I, P320A, S322V, N330D, I332F, A343V, G345D, F350L, A357S, G358R, G360M, D365S, M371V, D375A, D375G, A379T, D380H, D380Y, D380N, M381V, L382A, D385E, S386C, S386E, P389L, P389Q, P389I, T390A, T390S, T390A, A392G, A392I, A392L, P397A, P397G, P397K, P397W, P397C, P397L, K400A, D405P, S407G, T413P, S426F, N427D, T430Y, T440L, T440R, T440G, T444S, T445D, S446T, S447L, T450D, S453D, T455A, T456S, S458E, K459E, K459S, S462I, T463I, T464A, T464A, H492L, Y493S, Y493W, A494D, A494S, C496S, C496Y, G497C, G498D, G498S, T502N, G503D, C507Y, P510V, P510S, C513R, C513W, K515D, Q516P, and N517D.

Please amend Claim 9 (Column 127, Lines 1-28) as follows:
9. The cellobiohydrolase variant of claim 8, wherein the alteration is selected from the group consisting of G4C, A21P, S26A, W38A, R39L, T44I, T44M, T44N, T44K, S45D, S45N, G46A, G46I, G46L, G46T, Y51I, T52R, T52W, G53A, G53M, G53R, G53W, N54S, N54I, N54D, A72C, G75S, S87T, L93V, N94S, N94A, N94R, N94Q, F95L, F95Y, S100T, S100V, S100W, S100L, S100G, K102S, K102R, L108I, L111T, D114E, F129S, D130N, D130E, V131A, P137S, C138S, G139E, G139M, G139Q, G139S, G139R, L144A, L144V, D150N, A156G, K157R, S159P, I183N, D184S, A187L, P194*, P194Q, S195*, T196*, N197A, N197*, D198A, D198*, V199*, N200A, N200G, N200W, N200F, N200C, N200*, S201*, N205R, H206Y, C209S, A211T, N219S, M237T, D241L, D241R, D241V, Y247C, A253D, A253R, G260D, N264Y, T271I, V280I, P320A, S322V, N330D, Signed and Sealed this
Twentieth Day of August, 2024

Katherine Kelly Vidal
*Director of the United States Patent and Trademark Office*

I332F, A343V, G345D, F350L, A357S, G358R, G360M, D365S, M371V, D375A, D375G, A379T, D380H, D380Y, D380N, M381V, L382A, D385E, S386C, S386E, P389L, P389Q, P389I, T390A, T390S, T390A, A392G, A392I, A392L, P397A, P397G, P397K, P397W, P397C, P397L, K400A, D405P, S407G, T413P, S426F, N427D, T430Y, T440L, T440R, T440G, T444S, T445D, S446T, S447L, T450D, S453D, T455A, T456S, S458E, K459E, K459S, S462I, T463I, T464A, T464A, H492L, Y493S, Y493W, A494D, A494S, C496S, C496Y, G497C, G498D, G498S, T502N, G503D, C507Y, P510V, P510S, C513R, C513W, K515D, Q516P, and N517D.